(12) United States Patent
Roberts et al.

(10) Patent No.: US 7,192,657 B2
(45) Date of Patent: Mar. 20, 2007

(54) ETHYNYL CONTAINING ELECTRON TRANSPORT DYES AND COMPOSITIONS

(75) Inventors: Ralph R. Roberts, Cottage Grove, MN (US); Yingbo Li, Woodbury, MN (US); Sergey A. Lamansky, Apple Valley, MN (US)

(73) Assignee: 3M Innovative Properties Company, St. Paul, MN (US)

(*) Notice: Subject to any disclaimer, the term of this patent is extended or adjusted under 35 U.S.C. 154(b) by 157 days.

(21) Appl. No.: 10/414,073

(22) Filed: Apr. 15, 2003

(65) Prior Publication Data

US 2004/0214037 A1 Oct. 28, 2004

(51) Int. Cl.
*H05B 33/14* (2006.01)
*C09K 11/06* (2006.01)
*H01B 1/12* (2006.01)

(52) U.S. Cl. .................. 428/690; 428/917; 252/301.16; 252/301.35; 252/500; 257/40; 313/504; 313/506; 548/148; 548/262.2

(58) Field of Classification Search .............. 428/690, 428/917; 313/504, 506; 257/40; 252/301.35, 252/500; 528/101; 548/145, 262.2
See application file for complete search history.

(56) References Cited

U.S. PATENT DOCUMENTS

| 4,252,671 | A | 2/1981 | Smith |
| 5,061,569 | A | 10/1991 | VanSlyke et al. |
| 5,166,024 | A | 11/1992 | Bugner et al. |
| 5,256,506 | A | 10/1993 | Ellis et al. |
| 5,351,617 | A | 10/1994 | Williams et al. |
| 5,408,109 | A | 4/1995 | Heeger et al. |
| 5,508,136 | A | 4/1996 | Shirota et al. |
| 5,536,588 | A | 7/1996 | Naito |

(Continued)

FOREIGN PATENT DOCUMENTS

| DE | 3610649 | 10/1987 |
| EP | 0 553 950 A2 | 8/1993 |
| EP | 0650955 | 5/1995 |
| EP | 0827367 | 3/1998 |
| EP | 0879868 | 11/1998 |
| EP | 0891121 | 1/1999 |

(Continued)

OTHER PUBLICATIONS

Ayabe et al., "*Construction of Monomeric and Polymeric Porphyrin Compartments by a Pd(II)–Pyridine Interaction and Their Chiral Twisting by a BINAP Ligand*", Journal of Organic Chemistry, vol. 68, No. 3, pp. 1059–1066 (2003).
Ikeda et al., "*A Novel Self–Assembled Porphyrin Polymer Constructed by a Pd(II)– Pyridine Interaction*", Chemical Letters, vol. 11, pp. 1138–1139 (2001).
Tomizaki et al., "*Practical Synthesis of Perylene–Monoimide Building Blocks That Possess Features Appropriate For Use In Porphyrin–Based Light–Harvesting Arrays*", Tetrahedron, vol. 59, No. 8, pp. 1191–1207 (2003).

(Continued)

*Primary Examiner*—Rena Dye
*Assistant Examiner*—Camie S Thompson
(74) *Attorney, Agent, or Firm*—Jean A. Lown

(57) ABSTRACT

Compounds, compositions, organic electronic devices, and methods for preparing organic electronic devices are described. The compounds of the invention contain at least two carbon-carbon triple bonds and a heteroaromatic ring having at least one —C=N— unit. The compounds can be used as electron transport agents in organic electronic devices such as organic electroluminescent devices.

42 Claims, 4 Drawing Sheets

U.S. PATENT DOCUMENTS

| | | | |
|---|---|---|---|
| 5,550,290 A | 8/1996 | Mizuta et al. | |
| 5,621,131 A | 4/1997 | Kreuder et al. | |
| 5,681,664 A | 10/1997 | Tamano et al. | |
| 5,693,446 A | 12/1997 | Staral et al. | |
| 5,695,907 A | 12/1997 | Chang | |
| 5,707,745 A | 1/1998 | Forrest et al. | |
| 5,708,130 A | 1/1998 | Woo et al. | |
| 5,710,097 A | 1/1998 | Staral et al. | |
| 5,725,989 A | 3/1998 | Chang et al. | |
| 5,728,801 A | 3/1998 | Wu et al. | |
| 5,792,557 A | 8/1998 | Nakaya et al. | |
| 5,840,217 A | 11/1998 | Lupo et al. | |
| 5,869,350 A | 2/1999 | Heeger et al. | |
| 5,900,327 A | 5/1999 | Pei et al. | |
| 5,929,194 A | 7/1999 | Woo et al. | |
| 5,945,502 A * | 8/1999 | Hsieh et al. | 528/101 |
| 5,998,085 A | 12/1999 | Isberg et al. | |
| 6,030,715 A | 2/2000 | Thompson et al. | |
| 6,074,734 A | 6/2000 | Kawamura et al. | |
| 6,114,088 A | 9/2000 | Wolk et al. | |
| 6,132,641 A | 10/2000 | Rietz et al. | |
| 6,150,043 A | 11/2000 | Thompson et al. | |
| 6,169,163 B1 | 1/2001 | Woo et al. | |
| 6,194,119 B1 | 2/2001 | Wolk et al. | |
| 6,203,933 B1 | 3/2001 | Nakaya et al. | |
| 6,214,520 B1 | 4/2001 | Wolk et al. | |
| 6,221,543 B1 | 4/2001 | Guehler et al. | |
| 6,221,553 B1 | 4/2001 | Wolk et al. | |
| 6,228,543 B1 | 5/2001 | Mizuno et al. | |
| 6,228,555 B1 | 5/2001 | Hoffend, Jr. et al. | |
| 6,242,115 B1 | 6/2001 | Thomson et al. | |
| 6,242,152 B1 | 6/2001 | Staral et al. | |
| 6,284,425 B1 | 9/2001 | Staral et al. | |
| 6,329,082 B1 | 12/2001 | Kreuder et al. | |
| 6,358,664 B1 | 3/2002 | Nirmal et al. | |
| 6,485,884 B2 | 11/2002 | Wolk et al. | |
| 6,521,324 B1 | 2/2003 | Debe et al. | |
| 6,664,111 B2 | 12/2003 | Bentsen et al. | |
| 2002/0158574 A1 | 10/2002 | Wolk et al. | |
| 2003/0068525 A1 | 4/2003 | Bellmann et al. | |
| 2003/0124265 A1 | 7/2003 | Bellmann et al. | |
| 2006/0051611 A1 | 3/2006 | Brunner et al. | |

FOREIGN PATENT DOCUMENTS

| | | |
|---|---|---|
| EP | 0953624 | 11/1999 |
| EP | 0968175 B | 1/2000 |
| EP | 1 170 273 A1 | 1/2002 |
| EP | 1170273 | 1/2002 |
| JP | 295695/1988 | 2/1988 |
| JP | 191694/1990 | 7/1990 |
| JP | 000792/1991 | 1/1991 |
| JP | 5-152072 | 6/1993 |
| JP | 5-202011 | 8/1993 |
| JP | 6-096860 | 4/1994 |
| JP | 10-195063 | 7/1998 |
| JP | 2000-195673 | 7/2000 |
| WO | WO 98/06773 | 2/1998 |
| WO | WO 98/55561 | 12/1998 |
| WO | WO 99/32537 | 7/1999 |
| WO | WO 99/40655 | 8/1999 |
| WO | WO 00/18851 | 4/2000 |
| WO | WO 00/70655 | 11/2000 |
| WO | WO 01/39234 | 5/2001 |
| WO | WO 01/41512 | 6/2001 |
| WO | WO 02/22374 | 3/2002 |
| WO | WO 03/019179 | 3/2003 |

Tomizaki et al., "Synthesis and Photophysical Properties of Light–Harvesting Arrays Comprised of a Porphyrin Bearing Multiple Perylene–Monoimide Accessory Pigments", Journal of Organic Chemistry, vol. 67, pp. 6519–6534 (2002).

Cha et al., "Synthesis and Luminescence Properties of Four–Armed Conjugated Structures Containing 1,3,4–oxadiazole Moieties", Journal of Materials Chemistry, vol. 13, No. 8, pp 1900–1904 (2003).

Nam et al., "Photoluminescence and Electroluminescence Properties of Poly(9–vinylcarbarzole) Doped With Anthracene Derivatives Containing bis(ethynylphenyl oxadiazole) or bis(vinylphenyl oxadiazole) Substituents", Synthetic Metals, vol. 130, No. 3, pp. 271–277 (2002).

Amashukeli et al., J. Phys. Chem. A., 106(33) 7593–7598 (2002).

Bailey, T.R., Tetrahedron Lett., 27, 4407–4410 (1986).

Barton et al., Tetrahedron Lett., 24 (15) 1601–1604 (1983).

Bettenhausen et al., Synthetic Metals, 91, 223–228 (1997).

Bokova et al., J. Org. Chem. USSR (Engl. Transl), 5, 1103–1106 (1969).

Brownstein, S.K., et al., J. Org. Chem., 67, 663 (2002).

Bumagin, N.A. et al., J. Organomet. Chem., 364 231–234 (1989).

Chen, C.H., et al., "Recent Developments in Molecular Organic Electroluminescent Materials," Macromolecular Symposia, 125, 1–48 (1997).

Clayden, J., et al., J. Chem. Soc., Perkin Trans, 1, 7 (1995).

Creason, S.C., et al., J. Org. Chem. 37, 4440–4446 (1972).

Fischer, Chem Ber., 25, 2826–2846 (1892).

Friend, R.H., et al., "Electroluminescence in Conjugated Polymers", Nature, 121, 397 (1999).

Fritsch, et al., Chem Ber., 125, 849–855 (1992).

Fujikawa, et al., Synthetic Metals, 91, 161–162 (1997).

Gautun et al., Acta Chem. Scand., 45(6), 609–615 (1991).

Goodbrand et al., J. Org. Chem. 64, 670–674 (1999).

Grazulevicius, J.V. et al., "Charge–Transporting Polymers and Molecular Glasses", Handbook of Advanced Electronic and Photonic Materials and Devices, H.S. Nalwa (ed.), 10, 233–274 (2001).

Grekov et al., J. Gen. Chem. USSR (Engl. Transl) 30, 3763–3766 (1960).

Halls, J.J.M., et al., "Light–emitting and Photoconductive Diodes Fabricated with Conjugated Polymers," Thin Solid Films, 276, 13–20 (1996).

Huntress et al., J. Am. Chem. Soc., 55, 4262–4270 (1933).

Ishiyama et al., J. Org. Chem., 60, 7508–7510 (1995).

Kajino et al., Chem. Pharm. Bull, 39 (11), 2888–2895 (1991).

Kido, J., "Organic Electroluminescent Devices Based on Polymeric Materials," Trends in Polymer Science, 2, 350–355 (1994).

Klingsberg, E. J. Org. Chem., 23, 1086–1087 (1958).

Koene, B.E., et al., Chem. Mater., 10, 2235–2250 (1998).

Kraft, et al., Angew. Chem. Int. Ed., 37, 402–428 (1998).

Kreger, K. et al., Synthetic Metals, 119, 163 (2001).

Kristensen et al., Org. Lett., 10, 1435–1438 (2001).

Meng, et al., J. Am. Chem. Soc., 123(37), 9214–9215 (2001).

Miyaura, N., et al., Chemical Reviews, 95, 2457–2483 (1995).

Moss, et al., J. Chem. Soc. Perkin Trans, 1(9), 1999–2006 (1982).

Myznikov et al., J. Gen. Chem. USSR (Engl. Transl.), 62(6), 1125–1128 (1992).

Namkung et al., J. Med. Chem. Soc., 8, 551–554 (1965).

Otera, J., et al., *Bull. Chem. Soc. Jpn*, 54, 2964–2967 (1981).
Park, M., et al., *Tetrahedron*, 42, 12707–12714 (1998).
Pei, et al., *J. Org. Chem.*, 67, 4924–4936 (2002).
Pei, Q., et al., "Polymer Light–Emitting Electrochemical Cells: In Situ Formation of Light–Emitting p–n Junction," *Journal of the American Chemical Society*, 118, 3922–3929 (1996).
Pilgram, K., et al., *J. Heterocycl. Chem*, 7, 629–633 (1970).
Prudchenko, A.T., et al., *J. Gen. Chem. USSR* (Engl. Transl.), 37,2082–2084 (1967).
Ranger, M., et al., *Can. J. Chem.*, 76, 1571–1577, 1998.
Ranger, M., et al., *Chem. Commun.*, 1597–1598 (1997).
Rule et al., *J. Chem. Soc.*, 1096–1101 (1937).
Salbeck et al., Low Molecular Organic Glasses for Blue Electroluminescence, *Synthetic Metals*, 91, 209–215 (1997).
Sanechika et al., *Bull. Chem. Soc. Jpn.*, 57, 752–755 (1984).
Schidio et al., *Chem Ber.*, 96, 2595–2600 (1963).
Shen, Z., et al., Three–Color, Tunable, Organic Light–Emitting Devices, *Science*, 276, 2009–2011 (1997).
Strohriegl, P., "Charge Transporting Molecular Glasses," *Adv. Mat.*, 14, 1439 (2002).

Strukelj et al., *Science*, 267,1969 (1995).
Takahashi et al., *Synthesis*, 627 (1980).
Takeda et al., *J. Org. Chem.*, 52 (18), 4137–4139 (1987).
Tamoto, et al., *Chem. Mater.*, 1077–1085 (1997).
Tanaka et al., *Chem. Commun.*, 2175–2176 (1996).
Tokito et al., *Appl. Phys. Lett.*, 70(15), 1929–1931 (1997).
Tokito et al., *Polym. Prep.* (Am. Chem. Soc. Div. Polym. Chem.) 38(1), 388–389 (1997).
Tokito et al., *Synthetic Metals*, 111–112, 393–396 (2000).
Weber, E, et al., *J. Chem. Soc. Perkin Trans*, 2, 1251–1258 (1988).
Weil et al., *J. Amer. Chem. Soc.*, 123(33), 8101–8108 (2001).
Widdowson, D.A., et al., *Tetrahedron*, 42, 2111 (1986).
Yoon et al., *J. Chem. Soc., Chem. Commun.*, 13, 1013–1014 (1987).
Zinke, A., et al., *Chem. Ber.*, 74, 107–112 (1941).

\* cited by examiner

ETHYNYL CONTAINING ELECTRON TRANSPORT DYES AND COMPOSITIONS

TECHNICAL FIELD

This invention relates to compounds, compositions, organic electronic devices, and methods for preparing organic electronic devices. More particularly, the invention relates to compounds and compositions that can be used as electron transport agents in organic electronic devices such as organic electroluminescent devices.

BACKGROUND

Organic electroluminescent (OEL) devices such as organic light emitting diodes (OLEDs) are desirable for use in electronic media because of their thin profile, low weight, capability of obtaining a wide variety of emission colors, and low driving voltage. OLEDs have potential use in applications such as backlighting of graphics, pixelated displays, and large emissive graphics.

There is continuing research and development of electroluminescent materials, electroactive materials, and charge transporting materials suitable for such devices and methods for making the devices. In some instances, materials can be selected or developed which facilitate one or more of these device preparation methods. Pattern-wise thermal transfer of materials from donor sheets to receptor substrates has been proposed as one method for forming OEL devices. Selective thermal transfer of organic light emitters for formation of organic electroluminescent devices has been shown to be particularly useful.

Molecular oxadiazole and triazole derivatives have been used as electron transport/hole blocking materials in OLED devices. One oxadiazole derivative commonly used is 2-(4-biphenyl)-5-(4-t-butylphenyl)-1,3,4-oxadiazole (PBD). One triazole derivative commonly used is 3-(4-biphenylyl)-4-phenyl-5-(4-tert-butylphenyl)1,2,4-triazole (TAZ). However, OLED devices employing PBD or TAZ often exhibit short operating lifetimes due to recrystallization of or aggregate formation by the PBD or TAZ, leading to phase separation and formation of charge carrier traps that inhibit emission.

In an effort to mitigate these problems in blended polymer systems, several groups have reported bonding an electron transporting structure such as PBD to a flexible polymer chain, resulting in amorphous materials. For example, polymethylmethacrylates bearing oxadiazole side chains have been reported. However, operating lifetimes for devices based on these materials were found to be extremely short due to PBD aggregation (e.g., see Strukelj et al., *Science*, 267, 1969, (1995)).

SUMMARY OF THE INVENTION

The present invention discloses compounds, compositions, organic electronic devices, and methods for preparing organic electronic devices. More particularly, compounds and compositions are disclosed that contain at least two carbon-carbon triple bonds and a heteroaromatic ring having at least one —C=N— unit. The compounds can be used as electron transport agents in organic electronic devices such as organic electroluminescent devices.

One aspect of the invention provides a compound of Formula I:

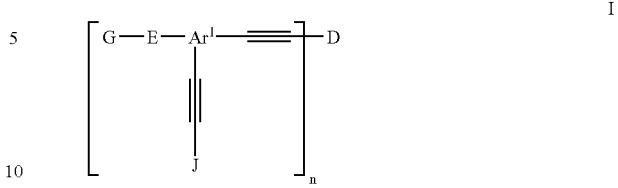

wherein
D is a core that is a monovalent, divalent, trivalent, or tetravalent radical of a $C_{3-30}$ alkane, $C_{3-30}$ heteroalkane, conjugated or unconjugated $C_{6-60}$ carbocyclic aromatic compound, $C_{3-60}$ heteroaromatic compound, $C_{18-60}$ tertiary aromatic amino compound, or a compound of Formula II or Formula III

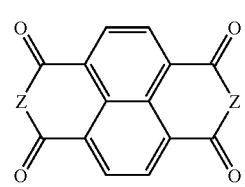

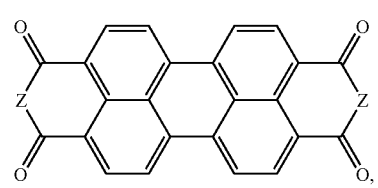

that is unsubstituted or substituted with one or more alkyl, alkenyl, alkoxy, aryl, aryloxy, fluoro, fluoroalkyl, perfluoroalkyl, heteroalkyl, heteroaryl, or combinations thereof, wherein
$Ar^1$ is trivalent radical of a conjugated $C_{6-30}$ carbocyclic aromatic compound that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;
E is a $C_{3-60}$ heteroarylene having a —C=N— unit, said heteroarylene being unsubstituted or substituted with one or more alkyl, alkenyl, alkoxy, aryl, aryloxy, fluoro, fluoroalkyl, perfluoroalkyl, heteroalkyl, heteroaryl, or combinations thereof;
G is a monovalent radical selected from hydrogen, $C_{1-30}$ alkyl, $C_{1-30}$ heteroalkyl, $C_{3-60}$ heteroaryl, $C_{6-60}$ aryl, or $C_{18-60}$ tertiary aromatic amino aryl that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;
J is a monovalent radical selected from $C_{1-30}$ alkyl, $C_{1-30}$ heteroalkyl, $C_{3-60}$ heteroaryl, $C_{6-60}$ aryl, or $C_{18-60}$ tertiary aromatic amino aryl that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;
Z is NH or $CH_2$ and
n is an integer of 1 to 4, wherein no more than one of D and J is an unsubstituted phenyl when n is equal to 1.
Another aspect provides a composition that includes a compound according to Formula I in combination with at least one other compound that is a charge transporting material, charge blocking material, light emitting material, color conversion material, polymeric binder, or combination thereof.

Yet another aspect provides an organic electronic device that includes a compound according to Formula I or a composition of the invention. In some embodiments, the organic electronic device is an organic electroluminescent device.

Additionally, a method of making an organic electroluminescent device is disclosed. The method includes (1) preparing a donor sheet that includes a transfer layer containing a compound according to Formula I or a composition of the invention and (2) transferring the transfer layer to a surface of a receptor substrate.

The above summary of the present invention is not intended to describe each disclosed embodiment or every implementation of the present invention. The Figures and the detailed description that follow more particularly exemplify these embodiments.

BRIEF DESCRIPTION OF THE DRAWINGS

The above aspects may be more completely understood in consideration of the following detailed description of various embodiments in connection with the accompanying drawings, in which.

Figure 1:
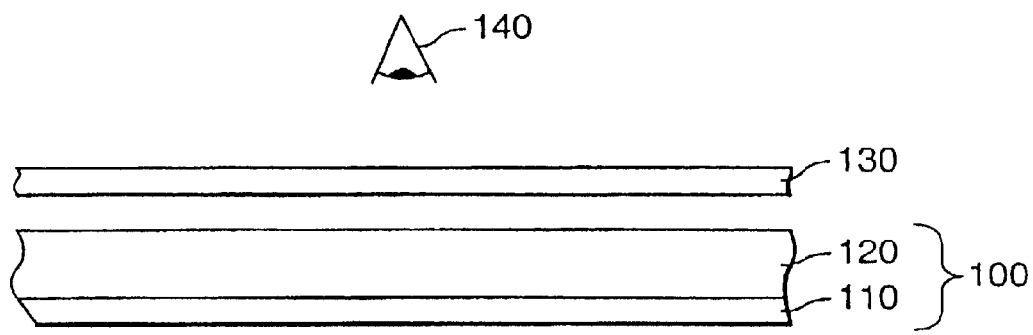
FIG. 1 is a schematic side view of an organic electroluminescent display construction.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the present disclosure.

DETAILED DESCRIPTION OF THE INVENTION

Definitions

As used herein, the terms "a", "an", and "the" are used interchangeably with "at least one" to mean one or more of the elements being described.

As used herein, the term "active" when used to refer to a compound means that the compound can transport holes, transport electrons, participate in electron/hole recombination, emit light, or a combination thereof.

As used herein, the term "amorphous" refers to a compound or composition that is not crystalline and that does not crystallize when removed from a solvent.

As used herein, the term "alkane" refers to a saturated hydrocarbon that can be straight chained, branched, or cyclic. The alkane can be unsubstituted or substituted and typically includes 1 to about 20 or 1 to about 10 carbon atoms. Examples of alkanes include, but are not limited to, n-propane, n-butane, n-pentane, tert-butane, iso-propane, iso-butane, cyclopentane, cyclohexane, adamantane, n-octane, n-heptane, ethylhexane, decane, dodcecane, hexadecane, octadecane, and icosane.

As used herein, the term "alkyl" includes both straight-chained, branched, and cyclic alkyl groups that are unsubstituted or substituted. An alkyl is a monovalent radical of an alkane. The alkyl group typically has 1 to about 30 carbon atoms. In some embodiments, the alkyl group contains 1 to about 20 or 1 to about 10 carbon atoms. Examples of alkyl groups include, but are not limited to methyl, ethyl, n-propyl, n-butyl, n-pentyl, tert-butyl, isopropyl, isobutyl, n-octyl, n-heptyl, and ethylhexyl.

As used herein, the term "alkenyl" refers to a monovalent radical of a straight-chained, branched, or cyclic alkene having one or more aliphatic carbon-carbon double bond and includes both unsubstituted and substituted alkenyl groups. The alkenyl groups typically include 2 to about 30 carbon atoms. In some embodiments, the alkenyl groups contain 2 to about 20 or 2 to about 10 carbon atoms. Examples of alkenyl groups include, but are not limited to, n-oct-3-enyl and n-hept-6-enyl. The alkenyl groups can have alternating double and single carbon-carbon bonds. For example, the alkenyl groups can be a diene or a triene with a single carbon-carbon bond between each carbon-carbon double bond.

As used herein, the term "alkoxy" refers to a group having an oxygen atom attached to an alkyl group. The alkoxy group typically has 1 to about 30 carbon atoms. In some embodiments, the alkoxy group contains 1 to about 20 or 1 to about 10 carbon atoms. Examples include methoxy, ethoxy, propoxy, butoxy, and the like. An alkoxy is a subset of a heteroalkyl group. Alkoxy groups can be unsubstituted or substituted.

As used herein, the term "aromatic" refers to both carbocyclic aromatic compound or groups and heteroaromatic compound or groups. A carbocyclic aromatic compound is a compound that contains only carbon atoms in an aromatic ring structure. A heteroaromatic compound is a compound that contains at least one heteroatom selected from S, O, N and P in ring in an aromatic ring structure.

As used herein, the term "aryl" refers to monovalent unsaturated aromatic carbocyclic radicals having one to ten rings, multiple fused rings, or combinations thereof. That is, an aryl is a monovalent radical of a carbocyclic aromatic compound. In some embodiments, the aryl group has up to 10 rings, up to 8 rings, up to 6 rings, up to 4 rings, up to 3 rings, up to 2 rings, or one aromatic ring. The aryl group can contain, for example, up to about 60, up to about 50, up to about 40, up to about 30, or up to about 20 carbon atoms. Examples of aryl groups include, but are not limited to, phenyl, biphenyl, terphenyl, anthryl, naphthyl, acenaphthyl, phenanthryl, dihydrophenathrenyl, anthracenyl, fluorenyl, 9-silafluorenyl, tetrahydropyrenyl, perylenyl, spirobisfluorenyl, fluoranthenyl, pyrenyl, dihydropyrenyl, tetrahydropyrenyl, rubrenyl, chrysenyl, 5,6,12,13-tetrahydrodibenzo[a,h]anthracenyl, 6,12-dihydroindeno[1,2-b]fluorenyl, 5,12-dihydro-6H-indeno[1,2-b]phenathrenyl, dihydrophenathrenyl, and benzo[g,h,i]perylenyl.

As used herein, the term "arylene" refers to divalent unsaturated aromatic carbocyclic radicals having one to ten rings, multiple fused rings, or combinations thereof. That is, an arylene is a divalent radical of a carbocyclic aromatic compound. In some embodiments, the arylene group has up to 8 rings, up to 6 rings, up to 4 rings, up to 3 rings, up to 2 rings, or one aromatic ring. In some examples, the arylene group contains up to 60 carbon atoms, up to 50 carbon atoms, up to 40 carbon atoms, up to 30 carbon atoms, or up to 20 carbon atoms. Examples of arylene groups include, but are not limited to, divalent radicals of benzene, naphthalene, acenaphthene, phenanthrene, anthracene, fluorene, 9-silafluorene, fluoranthene, benzopyrene, corene, dihyrophenanthrene, tetrahydropyrene, perylene, spirobisfluorene, pyrene, rubrene, and chrysene. Specific examples of arylene groups include benzene-1,3-diyl, benzene-1,4-diyl, naphthalene-2,7-diyl, naphthalene-2,6-diyl, naphthalene-1,4-diyl, naphthalene-1,5-diyl, acenaphthene-diyl, phenanthren-3,8-diyl, 5,6-dihydrophenathren-3,8-diyl, 4,5,9,10-tetrahydropyren-2,7-diyl, pyren-2,7-diyl, fluoren-2,7-diyl, 9-silafluoren-2,7-diyl, anthracene-9,10-diyl, perylene-3,9-diyl, perylene-3,10-diyl, spirobisfluorene-diyl, 5,6,12,13-tetrahydrodibenzo[a,h] anthracene-3,10-diyl, fluoranthene-diyl, rubrene-diyl, chrysene-diyl, benzo[g,h,i]perylene-diyl, and the like.

As used herein, the term "aryloxy" refers to a group having an oxygen atom attached to an aryl group. An example includes, but is not limited to, phenoxy.

An asterisk (-*) in any formula infra indicates the location of a bond to another group in a molecule.

As used herein, the term "carbocyclic" refers to a ring formed of carbon atoms. There are no heteroatoms in the ring structure.

As used herein, the term "conjugated" refers to unsaturated compounds having at least two carbon-carbon double or triple bonds with alternating carbon-carbon single bonds and carbon-carbon double or triple bonds. Likewise, the term "unconjugated" refers to unsaturated compounds that are not conjugated. For example, an unconjugated aromatic group can have two or more carbon-carbon single bonds interrupting alternating carbon-carbon single bonds and carbon-carbon double or triple bonds.

As used herein, the term "electroactive" refers a compound that transports holes, transports electrons, or participates in an electron/hole recombination.

As used herein, "electrochemically stable" is meant stable to electrochemical degradation such that any oxidation and/or reduction reactions entered into are reversible.

As used herein, the term "fluoroalkyl" refers to an alkyl group that has at least one hydrogen atom replaced with a fluorine atom.

As used herein, the term "heteroalkane" refers to an alkane in which at least one of the carbon atoms is replaced with a heteroatom selected from S, O, N, P, or Si. In some embodiments, heteroalkanes are ethers or thioethers. In other embodiments, the heteroalkanes contain poly (oxyalkylene) groups or poly(dialkylsiloxane) groups.

As used herein, the term "heteroalkyl" includes both straight-chained, branched, and cyclic alkyl groups with one or more heteroatoms independently selected from S, O, N, P, or Si and includes both unsubstituted and substituted alkyl groups. A heteroalkyl is a monovalent radical of a heteroalkane. The heteroalkyl group typically contains 1 to about 30 carbon atoms and can have up to 10 heteroatoms. In some embodiments, the heteroalkyl group contains 1 to about 20 or 1 to about 10 carbon atoms. An alkoxy group is a subset of a heteroalkyl group. Examples of heteroalkyl groups include, but are not limited to, methoxy, ethoxy, propoxy, 3,6-dioxaheptyl, 3-(trimethylsilyl)-propyl, poly (oxyalkylene) groups having a segment of formula —O($C_mH_{2m}$O)$_y$— where m is an integer of 1 to 6 and y is an integer of 2 to 20, and poly(dialkylsiloxane) groups having a segment of formula —[Si($C_wH_{2w+1}$)$_2$O]$_y$— where w is an integer of 1 to 10 and y is an integer of 2 to 20.

As used herein, the term "heteroaryl" refers to a monovalent radical of a five to seven member aromatic ring that includes one or more heteroatoms independently selected from S, O, N and P in the ring. That is, a heteroaryl is a monovalent radical of a heteroaromatic compound. Such a heteroaryl ring can be fused to one or more rings and can contain one to about 10 other rings selected from another heterocyclic ring(s), heteroaryl ring(s), aryl ring(s), cycloalkenyl ring(s), cycloalkyl rings, and combinations thereof. In some embodiments, the heteroaryl ring has up to 8 other rings, up to 6 other rings, up to 4 other rings, up to 3 other rings, up to 2 other rings, or one other ring. The heteroaryl typically contains up to about 60 carbon atoms. In some embodiments, the heteroaryl contains up to about 50 carbon atoms, up to about 40 carbon atoms, up to about 30 carbon atoms, or up to about 20 carbon atoms. Examples of heteroaryl groups include, but are not limited to, furanyl, thiophenyl, pyrrolyl, imidazolyl, pyrazolyl, triazolyl, tetrazolyl, thiazolyl, oxazolyl, isoxazolyl, oxadiazolyl, thiadiazolyl, isothiazolyl, pyridinyl, pyridazinyl, pyrazinyl, pyrimidinyl, quinolinyl, isoquinolinyl, benzofuranyl, benzothiophenyl, indolyl, carbazoyl, benzoxazolyl, benzothiazolyl, benzimidazolyl, cinnolinyl, quinazolinyl, quinoxalinyl, phthalazinyl, benzothiadiazolyl, benzotriazinyl, phenazinyl, phenanthridinyl, acridinyl, and indazolyl, siloles, and the like.

As used herein, "heteroaryls having a —C═N— unit" is a subset of the heteroaryls and refers to heteroaryls that have a —C═N— unit in at least one heteroaromatic ring. The —C═N— unit tends to be polarized and hence electron deficient in comparison to a —C═C— unit. Suitable examples include, but are not limited to, oxadiazolyls, N-substituted-triazolyls, N-substituted imidazolyls, N-substituted pyrazolyls, oxazolyls, isooxazolyls, thiazolyls, isothiazolyls, pyridinyls, pyridazinyls, pyrimidinyls, pyrazinyls, triazinyls, tetrazenyls, benzoxazolyls, benzothiazolyls, benzothiadiazolyls, quinolinyls, isoquinolinyls, cinnolinyls, quinazolinyls, quinoxalinyls, phthalazinyls, benzotriazinyls, phenazinyls, phenanthridinyls, acridinyls, and the like.

As used herein, "heteroaryls that are electron rich" is a subset of the heteroaryls and refers to heteroaryls that can donate electron density from the heteroatom into a pi bonding system. Examples include, but are not limited to, monovalent radicals of diarylsilanolyls, thiophenyls, bithiophenyls, furanyls, N-alkyl carbazolyl, N-aryl carbazolyl, N-alkyl pyrrolyl, N-aryl pyrrolyl, and the like.

As used herein, the term "heteroarylene" refers to an aromatic divalent radical of a five to seven member aromatic ring that includes one or more heteroatoms independently selected from S, O, N, and P. That is, a heteroarylene is divalent radical of a heteroaromatic compound. Such a heteroaromatic ring can be fused to one or more rings and can contain 1 to about 10 other rings selected from another heterocyclic ring(s), heteroaryl ring(s), aryl ring(s), cycloalkenyl ring(s), cycloalkyl rings, and combinations thereof. In some embodiments, the heteroaromatic ring is fused to up to 8 other rings, up to 4 other rings, up to 3 other rings, up to 2 other rings, or one other ring. The heteroarylene typically contains up to about 60 carbon atoms. In some embodiments, the heteroarylene contains up to about 50 carbon atoms, up to about 40 carbon atoms, up to about 30 carbon atoms, or up to about 20 carbon atoms.

Examples of heterarylene groups include, but are not limited to, divalent radicals of furan, thiophene, pyrrole, imidazole, pyrazole, triazole, tetrazole, thiazole, oxazole, isoxazole, oxadiazole, thiadiazole, isothiazole, pyridine, pyridazine, pyrazine, pyrimidine, quinoline, isoquinoline, benzofuran, benzothiophene, indole, carbazole, benzoaxazole, benzothizole, benzimidiazole, cinnoline, quinazoline, quinoxaline, phthalazine, benzothiadiazole, benzotriazine, phenazine, phenanthridine, acridine, indazole, and silones. Specific examples of heteroarylenes include, but are not limited to, furan-2,5-diyl, thiophene-2,4-diyl, 1,3,4-oxadiazole-2,5-diyl, 1,3,4-thiadiazole-2,5-diyl, 1,3-thiazole-2,4-diyl, benzo[1,2,5]thiadiazole-4,7-diyl, 1,3-thiazole-2,5-diyl, pyridine-2,4-diyl, pyridine-2,3-diyl, pyridine-2,5-diyl, pyrimidine-2,4-diyl, quinoline-2,3-diyl, 1,1-dialkyl-1H-silole-2,5-diyl, and the like.

As used herein, "heteroarylenes having at least one —C=N— unit" is a subset of heteroarylenes and refers to heteroarylenes having at least one —C=N— unit in at least one heteroaromatic ring. The —C=N— unit tends to be polarized and hence more electron deficient in comparison to a —C=C— unit. Examples of heteroarylenes having at least one —C=N— unit include, but are not limited to, divalent radicals of oxadiazoles, N-substituted-triazoles, N-substituted imidazoles, N-substituted pyrazoles, oxazoles, isoxazole, thiazoles, isothiazoles, pyridines, pyridazines, pyrimidines, pyrazines, triazines, tetrazenes, benzoxazoles, benzothiazoles, benzothiadiazoles, quinolines, isoquinolines, cinnolines, quinazolines, quinoxalines, phthalazines, benzotriazines, phenazines, phenanthridines, acridines, and the like.

As used herein, "heteroarylenes that are electron rich" is a subset of heteroarylenes and refers to heteroarylenes that can donate electron density from the heteroatom into a π system. Suitable examples include divalent radicals of diarylsilanoles, thiophenes, bithiophenes, furans, N-alkyl carbazoles, N-aryl carbazoles, N-alkyl pyrroles, N-aryl pyrroles, and the like.

As used herein, the term "inactive" when used to refer to a compound means that the compound is not electroactive, not electroluminescent, or a combination thereof.

As used herein, the term "perfluoroalkyl" refers to an alkyl group that has all the hydrogen atoms replaced with fluorine atoms. A perfluoroalkyl is a subset of a fluoroalkyl.

As used herein the term "solution processible" refers to a compound or composition that can be dissolved in a solution. In some embodiments, a compound or composition that is solution processible can be coated from a solution as a thin film. In other embodiments, a solution of the compound of composition can be applied to a substrate. For example, the solution can be printed or coated onto a substrate.

As used herein, the term "small molecule" refers to a compound that is non-polymeric (e.g., less than three repeating units when there are repeating units).

As used herein, the term "substituent" refers to a group such as an alkyl, alkenyl, alkoxy, aryl, aryloxy, heteroalkyl, heteroaryl, fluoro, fluoroalkyl, perfluoroalkyl, and the like. The various groups in Formula I can be substituted, for example, with one or more groups selected from $C_{1-30}$ alkyl, $C_{2-30}$ alkenyl, $C_{1-30}$ alkoxy, $C_{6-20}$ aryl, $C_{6-20}$ aryloxy, $C_{1-30}$ heteroalkyl, $C_{3-20}$ heteroaryl, fluoro, $C_{1-30}$ fluoroalkyl, $C_{1-30}$ perfluoroalkyl, and the like.

As used herein, the term "tertiary aromatic amine" refers to a class of molecular compounds having one or more tertiary nitrogen centers and each nitrogen center is bonded to three aromatic carbon centers. Examples of tertiary aromatic amines include diarylanilines; alkyl carbazole; aryl carbazole; and tetraaryldiamines such as, for example, N,N,N'N'-tetraarylbenzidines, N,N,N',N'tetraaryl-1,4-phenylenediamines, N,N,N'N'tetraaryl-2,7-diaminofluorene derivatives such as those taught in patent applications EP 0 953 624 A1 and EP 0 879 868 A2, N,N'-bis(3-methylphenyl)-N,N'-bis(phenyl)benzidine (also known as TPD), N,N'-bis(3-naphthalen-2-yl)-N,N'-bis(phenyl) benzidine (also known as NPB), 1,4-bis(carbazolyl)biphenyl (also known as CBP), and other tetraaryldiamine derivatives such as those described in B. E. Koene et al., *Chem. Mater.*, 10, 2235–2250 (1998), U.S. Pat. No. 5,792,557, U.S. Pat. Nos. 5,792,557, 5,550,290 and patent application EP 0 891 121 A1; peraryltriamine derivatives such as those described in U.S. Pat. No. 6,074,734 and patent application EP 0 827 367 A1; starburst amine derivatives such as 4,4',4"-tris(N,N-diarylamino)triphenylamines and 1,3,5-tris(4-diarylaminophenyl)benzenes, 4,4',4"-tris(N,N-diphenylamino)triphenylamine (also known as TDATA), 4,4',4"-tris(N-3-methylphenyl-N-phenylamino) triphenylamine (also known as mTDATA); 1,3,5-Tris(4-diphenylaminophenyl)benzenes (TDAPBs); and other dendridic and spiro amine derivatives as taught in patent application EP 0 650 955 A1, Tokito et al., *Polym. Prep.* (Am. Chem. Soc. Div. Polym. Chem.) 38(1), 388–389 (1997), Tanaka et al., *Chem. Commun.*, 2175–2176 (1996), and Tokito et al., *Appl. Inst. Phys.*, 70(15), 1929–1931 (1997).

As used herein, the term "tertiary aromatic amino aryl" refers to a monovalent aromatic ring radical of a tertiary aromatic amine as defined above.

As used herein, the term "tertiary aromatic amino arylene" refers to a divalent unsaturated aromatic carbocyclic radical of a tertiary aromatic amine as defined above.

Compounds

Compounds are disclosed that contain at least two ethynyl groups and a heteroaromatic ring having at least one —C=N— unit. The compounds can be used in organic electronic devices. For example, the compounds can be used as an electron transport material in organic electronic devices such as organic electroluminescent devices.

The compounds are of Formula I:

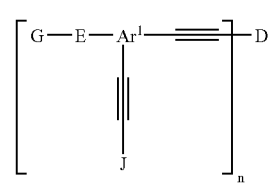

wherein

D is a core that is a monovalent, divalent, trivalent, or tetravalent radical of a $C_{3-30}$ alkane, $C_{3-30}$ heteroalkane, conjugated or unconjugated $C_{6-60}$ carbocyclic aromatic compound, $C_{3-60}$ heteroaromatic compound, $C_{18-60}$ tertiary aromatic amino compound, or a compound of Formula II or Formula III

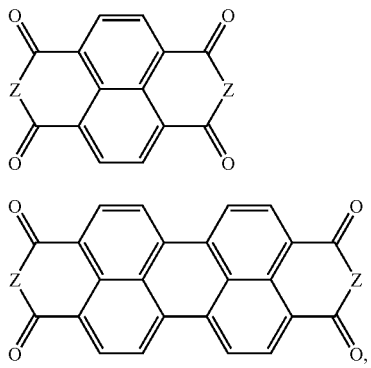

that is unsubstituted or substituted with one or more alkyl, alkenyl, alkoxy, aryl, aryloxy, fluoro, fluoroalkyl, perfluoroalkyl, heteroalkyl, heteroaryl, or combinations thereof, wherein $Ar^1$ is trivalent radical of a conjugated $C_{6-30}$ carbocyclic aromatic compound that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

E is an $C_{3-60}$ heteroarylene having a —C=N— unit, said heteroarylene being unsubstituted or substituted with one or more alkyl, alkenyl, alkoxy, aryl, aryloxy, fluoro, fluoroalkyl, perfluoroalkyl, heteroalkyl, heteroaryl, or combinations thereof;

G is a monovalent radical selected from hydrogen, $C_{1-30}$ alkyl, $C_{1-30}$ heteroalkyl, $C_{3-60}$ heteroaryl, $C_{6-60}$ aryl, or $C_{18-60}$ tertiary aromatic amino aryl that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

J is a monovalent radical selected from $C_{1-30}$ alkyl, $C_{1-30}$ heteroalkyl, $C_{3-60}$ heteroaryl, $C_{6-60}$ aryl, or $Cl_{18-60}$ tertiary aromatic amino aryl that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

Z is selected from $NH$ or $CH_2$; and n is an integer of 1 to 4, wherein no more than one of J and D is an unsubstituted phenyl when n is equal to 1.

The compounds of Formula I have a core (i.e., D in Formula I) and one to four end capping groups. The end capping groups are of Formula IV:

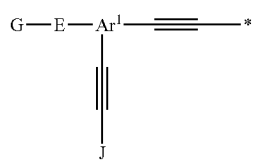

where the -* indicates where the end capping group is attached to the core D. When there are more than one end capping groups, the end capping groups can be the same or different. In some embodiments when there are more than one end capping groups, the end capping groups are the same.

The end capping groups contain at least two ethynyl groups. The end capping group also contains a group E that is a heteroarylene having at least one —C=N— unit. The —C=N— unit tends to be polarized and hence more electron deficient in comparison to a carbon-carbon double bond. The presence of both of the ethynyl groups and at least one —C=N— unit in the end capping group tend to provide the compounds according to Formula I with electron transport capabilities.

The remaining structures in the end capping group and in the core can be chosen to provide additional functions to the compounds. For example, in some embodiments, the compounds can be used as electron transporting agents as well as hole transporting materials. In other embodiments, the compounds can be used as electron transporting agents as well as light emitting materials. In still other embodiments, the compounds can be used as electron transport agents as well as hole blocking materials. The compounds can be solution processible and formed into thin film for use in organic electronic devices. In some embodiments, the end capping groups and the core can be chosen to provide a compound that is amorphous.

The number of carbon atoms specified for the various groups in Formula I (i.e., $Ar^1$, G, E, D, and J) does not include the carbon atoms that may be present in a substituent. For example, in some embodiments G can be a $C_{6-60}$ carbocyclic aryl. If G is a phenyl ring, G would be classified as having six carbon atoms. Likewise, if G is a phenyl ring substituted with a butyl group, G would still be classified as having six carbon atoms even though the total number of carbons would be ten. Thus, when G is a carbocyclic aryl, the total number of carbon atoms in G could be greater than 60.

Substituent groups can be on the core, the end capping groups, or a combination thereof. The substituents can be selected from alkyl, alkenyl, alkoxy, aryl, aryloxy, fluoro, fluoroalkyl, perfluoroalkyl, heteroalkyl, heteroaryl, and combinations thereof. In some embodiments, the compounds are substituted with a $C_{1-30}$ alkyl, $C_{2-30}$ alkenyl, $C_{1-30}$ alkoxy, $C_{6-30}$ aryl, $C_{6-20}$ aryloxy, fluoro, $C_{1-30}$ fluoroalkyl, $C_{1-30}$ perfluoroalkyl, $C_{1-30}$ heteroalkyl, $C_{3-30}$ heteroaryl, and combinations thereof. For example, the compounds can be substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, a $C_{3-20}$ heteroaryl, and combinations thereof.

The substituent groups can enhance, for example, the solubility of the compounds in organic solvents, the compatibility of the compounds with other materials in a composition, the solution processibility of the compounds, or a combination thereof. The substituents can modify the solubility parameter of the compound, modify the ionization potential, modify the electron affinity, reduce intramolecular or intermolecular interactions that can produce undesirable emissions, or any combination of these. For example, substituent groups can help suppress aggregation and phase separation of the compounds when the compounds are formed into thin films.

In some embodiments of the compounds of the invention, a substituent can include a divalent poly(oxyalkylene) soft segment of Formula V

or a divalent poly(dialkylsiloxane) soft segment of Formula VI

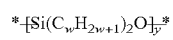

where m is an integer of 1 to 6, y is an integer of 2 to 20, and w is an integer of 1 to 10. In some embodiments, the poly(oxyalkylene) or poly(dialkylsiloxane) soft segment can be connected to an alkyl, aryl, or heteroaryl group. The substituent can, for example, have Formula VII

  VII where SS is a poly(oxyalkylene) or poly(dialkylsiloxane) soft segment, Ar is an arylene group, v is an integer of 0 or 1, and R″ is an aryl, heteroaryl, or a alkyl. In some examples, R″ is a sterically hindered group. Groups according to Formula VII can reduce the formation of intermolecular or intramolecular configurations that produce undesirable excimer or exciplex emission.

In other embodiments, the compounds of the invention can be substituted with one or more groups selected from fluoro, $C_{1-30}$ fluoroalkyl, $C_{1-30}$ perfluoroalkyl, and combinations thereof. These substituents can improve the solubility and the film forming properties of the compounds, can increase the ionization potential and electron affinity of the compounds, and a combination thereof. Compounds having an increased ionization potential and electron affinity can more easily inject electrons and block holes when used in organic electroluminescent devices. Fluoro, fluoroalkyl, or perfluoroalkyl substituents can also lower the vapor pressure of the compounds and make them easier to vapor deposit.

In some embodiments, substituents that are known to be photoluminescent quenchers, such as aryl carbonyls and nitro groups, may be undesirable because such groups can degrade the electroluminescent efficiency of organic electroluminescent devices. In some embodiments, substituents that are known to undergo electrochemical elimination reactions, such as alkyl amines, may be undesirable because such groups can degrade the operating lifetimes of organic electroluminescent devices. In some embodiments, substituents that contain titratable protons that can undergo electrochemical reactions, such as primary or secondary amines, phenols, alcohols, and the like, may be undesirable because such groups can be reduced to hydrogen during operation of an organic electroluminescent device. The generation of hydrogen can lead to delamination of the cathode and ultimate failure of the organic electroluminescent device. Chlorine, bromine, iodine, boronic acid, and boronic ester substituents can cause electrochemical instability in some embodiments. Such groups, if present in the compounds of the invention as impurities, should be present in amounts less than about 1000 parts per million (ppm) by weight. Additionally, groups such as parafluorophenyl may not be desirable in some applications because such groups are susceptible to irreversible electrochemical degradation. However, any of these groups can be included if other desirable characteristics can be obtained.

The core D can be a monovalent, divalent, trivalent, or tetravalent radical of a $C_{3-30}$ alkane, $C_{3-30}$ heteroalkane, conjugated or unconjugated $C_{6-60}$ carbocyclic aromatic compound, $C_{3-60}$ heteroaromatic compound, or $C_{18-60}$ tertiary aromatic amino compound that is unsubstituted or substituted with one or more alkyl, alkenyl, alkoxy, aryl, aryloxy, fluoro, fluoroalkyl, perfluoroalkyl, heteroalkyl, heteroaryl, or combinations thereof.

The core D can be, for example, a monovalent, divalent, trivalent, or tetravalent radical of an alkane or heteroalkane. The alkanes can be straight, branched, or cyclic. Suitable $C_{3-30}$ alkanes can include, but are not limited to, n-propane, n-butane, n-pentane, tert-butane, iso-propane, iso-butane, cyclopentane, cyclohexane, adamantane, n-octane, n-heptane, ethylhexane, decane, dodecane, hexadecane, octadecane, and icosane. Suitable $C_{3-30}$ heteroalkanes include one or more heteroatoms selected from S, O, N, P, and Si. The heteroalkanes, for example, can be ethers or thioethers. In some embodiments, the heteroalkane includes a poly(oxyalkylene) segment of formula —O($C_mH_{2m}$O)$_y$— or a poly(dialkylsiloxane) segment of formula —[Si($C_wH_{2w+1}$)$_2$O]$_y$— where w is an integer of 1 to 10, y is an integer of 2 to 20, and m is an integer of 1 to 6. The alkane or heteroalkane can be unsubstituted or substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, a $C_{3-20}$ heteroaryl, and combinations thereof.

In other examples of compounds according to Formula I, the core D can be a monovalent, divalent, trivalent, or tetravalent radical of a conjugated or unconjugated $C_{6-60}$ carbocyclic aromatic compound. The presence of such groups can impart, at least in some disclosed compounds, light emitting characteristics. The core D can be a radical of a $C_{6-60}$ carbocyclic aromatic compound selected from

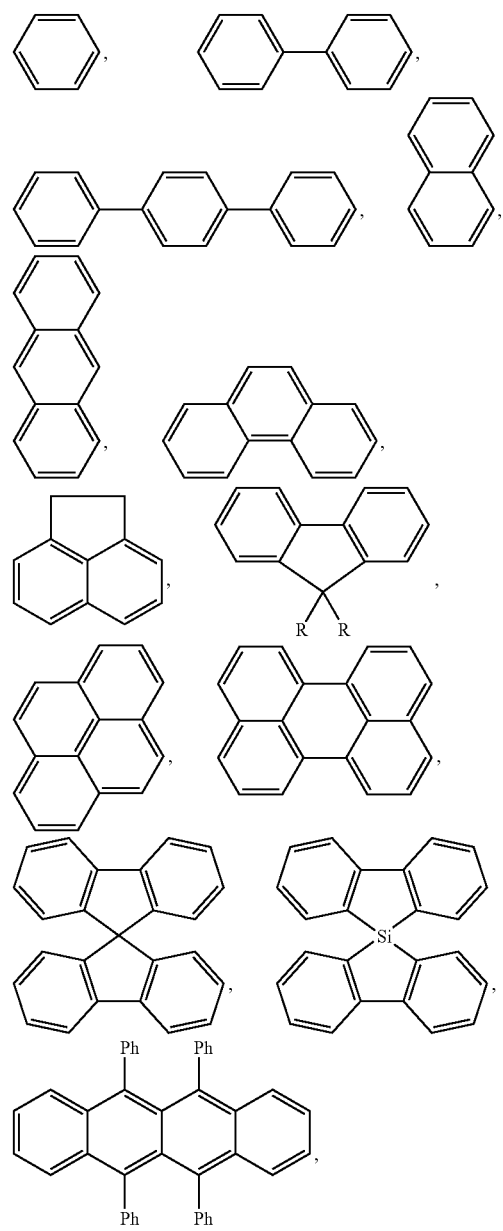

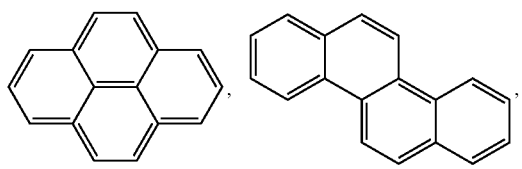

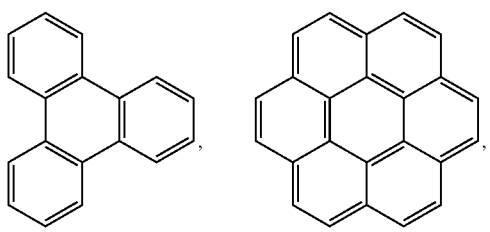

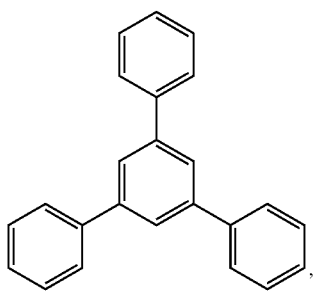

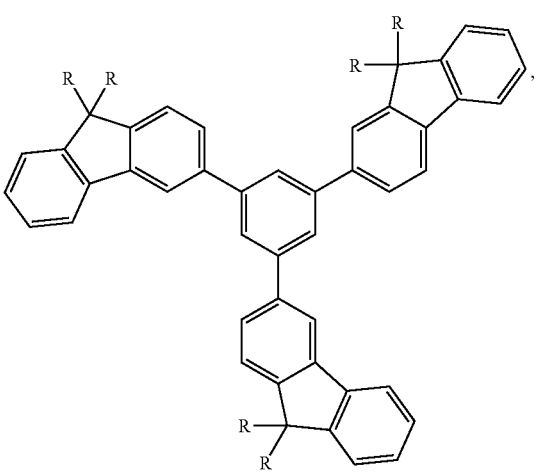

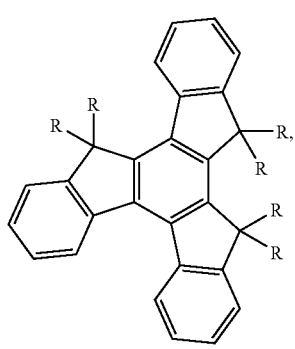

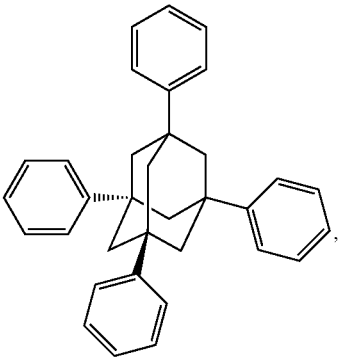

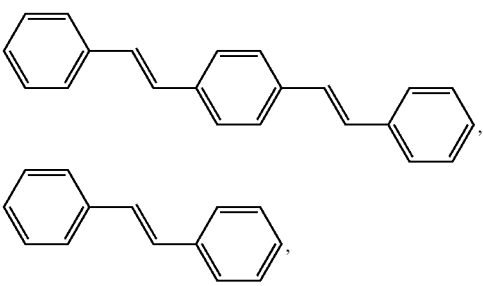

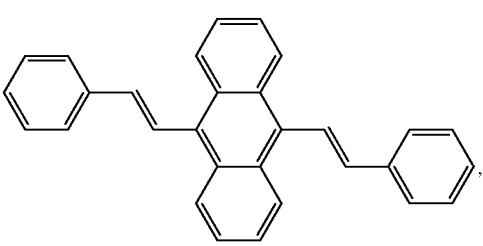

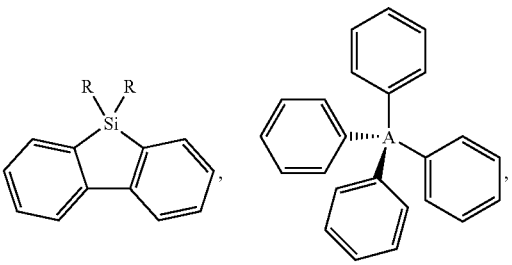

and the like that are unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof. Each A is C, Si, Ge, Pb, or Sn. Ph refers to a phenyl group.

When D is a non-conjugated carbocyclic aromatic group and there are more than one end capping group, the end capping groups can be connected such that they are all in the same conjugated portion of D, all in conjugated portions of D that are separated from each other by a non-conjugated portion, or a combination thereof. For example, if D is a divalent, trivalent, or tetravalent radical of

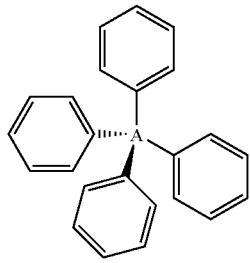

the end capping groups could all be attached to the same phenyl ring, to separate phenyl rings, or to a combination thereof. In some embodiments, A is Si or C.

The core D can be a monovalent, divalent, trivalent, or tetravalent radical of a $C_{3-60}$ heteroaromatic compound. In some examples, the $C_{3-60}$ heteroaromatic compound contains at least one —C=N— unit. The —C=N— unit tends to be more electron deficient compared to a carbon-carbon double bond and can enhance the electron transporting capabilities of the disclosed compounds. The core D can be a radical of a heteroaromatic compound selected from

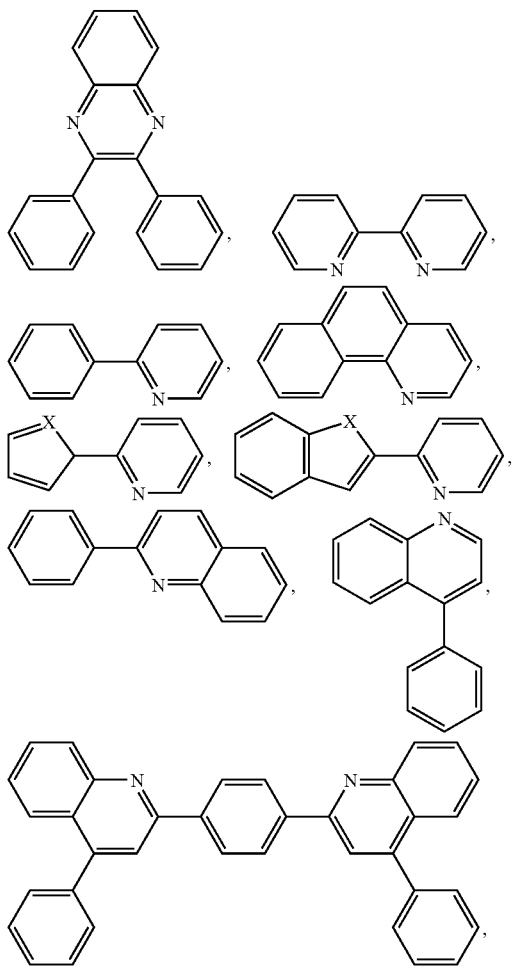

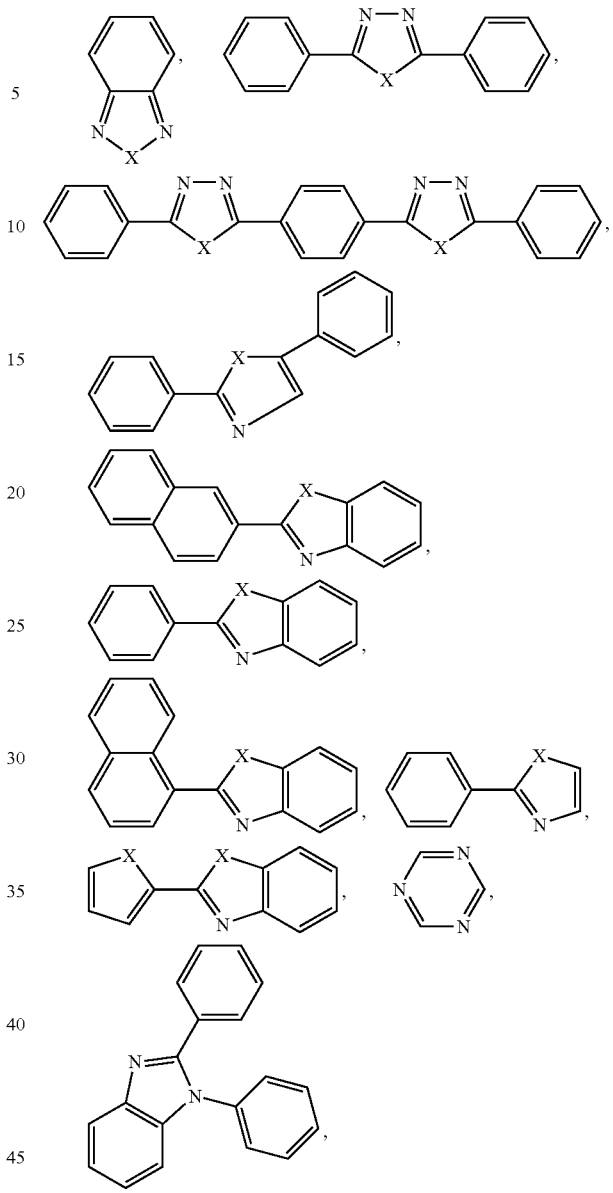

and the like that are unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each X is O, S, or $NR^2$ where $R^2$ is a $C_{1-30}$ alkyl, $C_{1-30}$ heteroalkyl, $C_{6-20}$ aryl, $C_{3-20}$ heteroaryl, or combinations thereof.

Some compounds of Formula I include a core D that is a monovalent, divalent, trivalent, or tetravalent radical of a $C_{3-60}$ heteroaromatic compound that are electron rich or a $C_{18-60}$ tertiary aromatic amino compound. In some instances, the presence of such D groups can impart hole transporting characteristics to the disclosed compounds. The core D can be a radical of a $C_{3-60}$ heteroaromatic or $C_{18-60}$ tertiary aromatic amino compound selected from

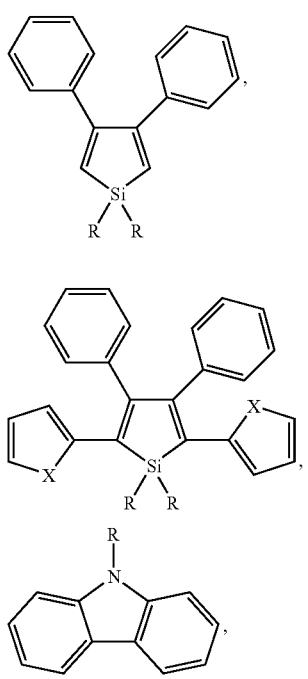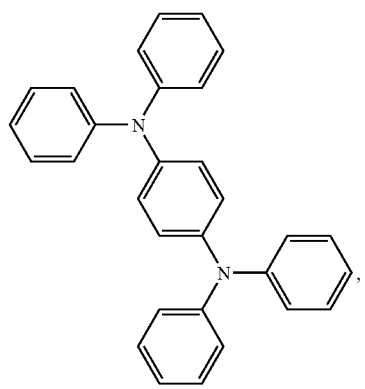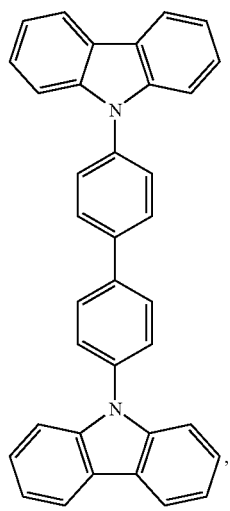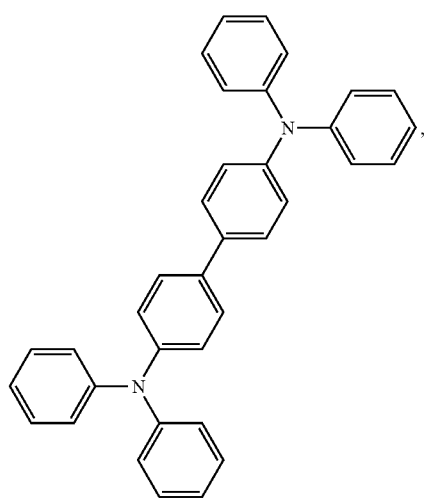

-continued

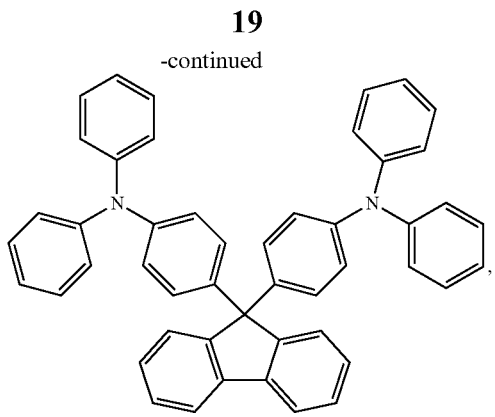

and the like that are unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each t is an integer of 0 to 4. Each R is independently a $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof. Each X is O, S, or $NR^2$ where $R^2$ is a $C_{1-30}$ alkyl, $C_{1-30}$ heteroalkyl, $C_{6-20}$ aryl, $C_{3-20}$ heteroaryl, or combinations thereof.

Other compounds according to Formula I have a core D that includes a monovalent, divalent, trivalent, or tetravalent radical of a compound of Formula II or Formula III

II

III

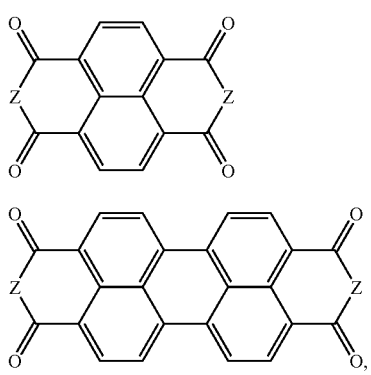

that is unsubstituted or substituted with one or more alkyl, alkenyl, alkoxy, aryl, aryloxy, fluoro, fluoroalkyl, perfluoroalkyl, heteroalkyl, heteroaryl, or combinations thereof. Each Z is NH or $CH_2$. The end capping groups can be attached to compounds of Formula II or III, for example, by abstraction of a hydrogen from Z.

Exemplary structures for D where n is equal to 2 include, but are not limited to,

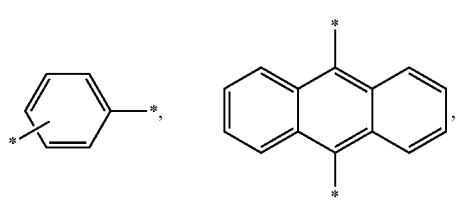

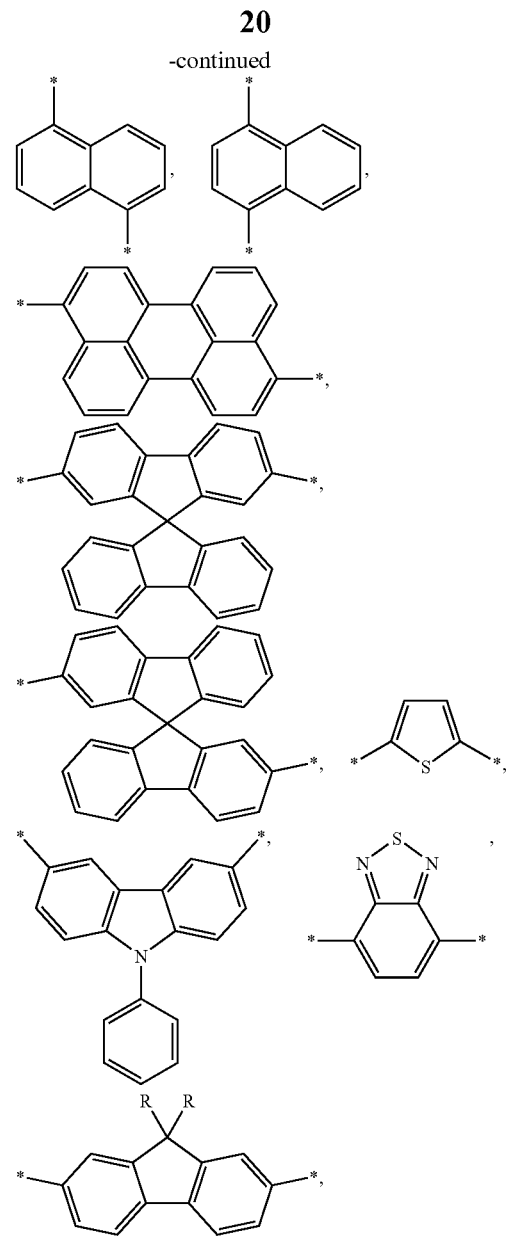

or the like that are unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently a $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof.

Exemplary structures for D where n is equal to 3 include, but are not limited to,

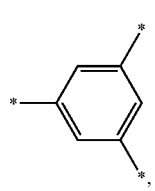

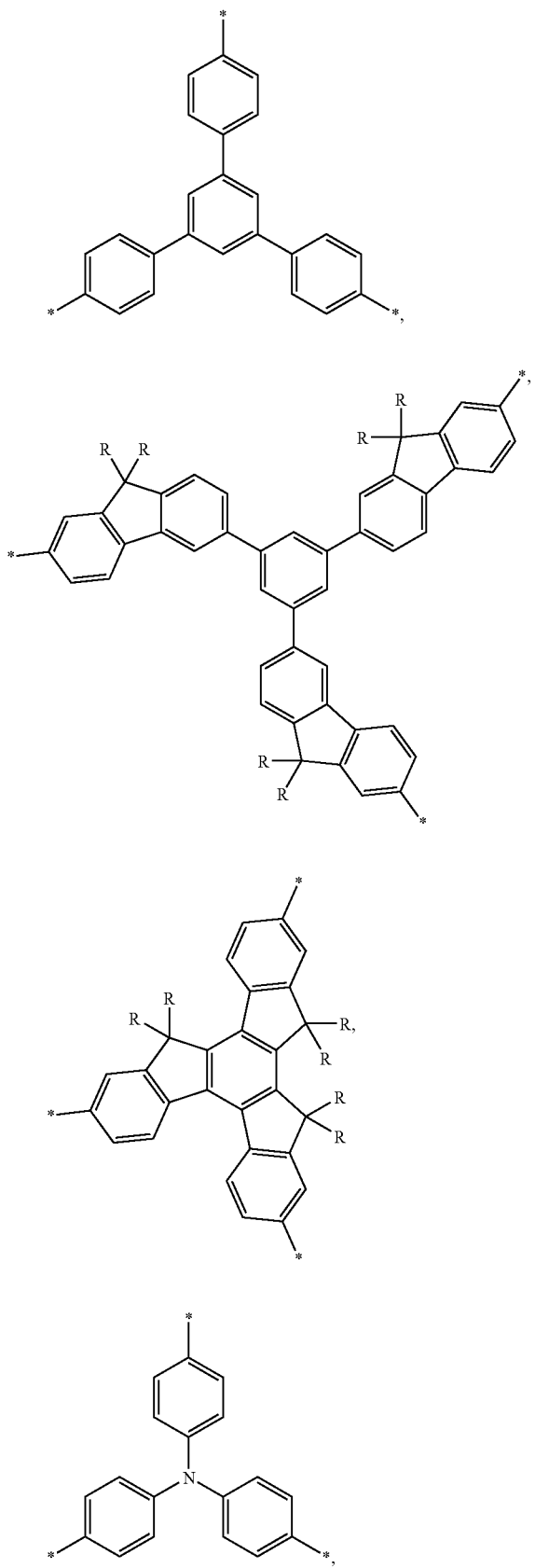

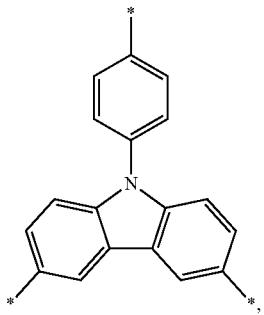

or the like that are unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently a $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof.

Exemplary structures for D where n is equal to 4 include, but are not limited to,

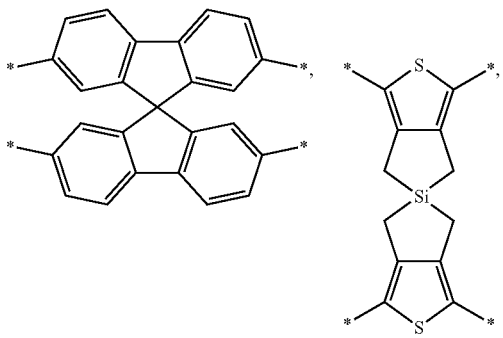

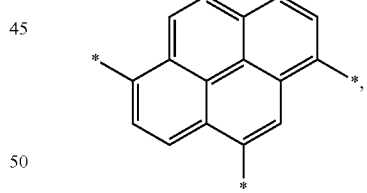

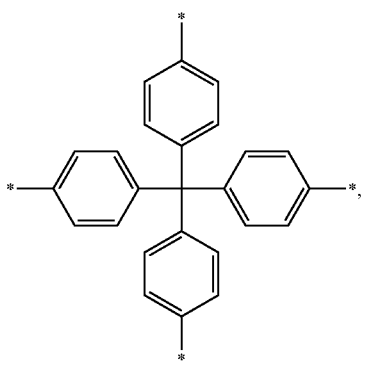

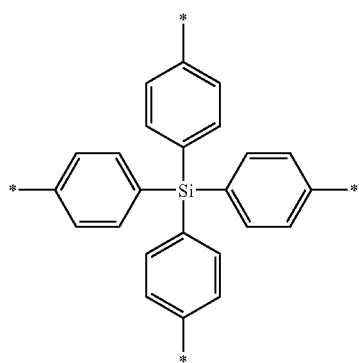

or the like that is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof.

In Formula I, $Ar^1$ is a trivalent radical of a conjugated $C_{6-30}$ carbocyclic aromatic compound that is unsubstituted or substituted with one or more alkyl, alkenyl, alkoxy, aryl, aryloxy, fluoro, fluoroalkyl, perfluoroalkyl, heteroalkyl, heteroaryl, or combinations thereof. Three moieties are attached to $Ar^1$ (i.e., two ethynyl groups and group E). The three moieties can be attached to the same carbocyclic ring of $Ar^1$ or to different carbocyclic rings of $Ar^1$ that are conjugated to each other.

In some embodiments, $Ar^1$ is a trivalent radical of

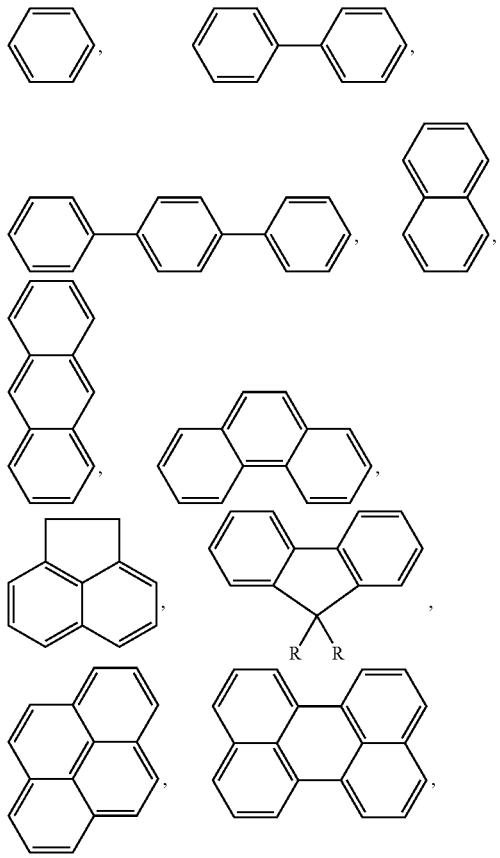

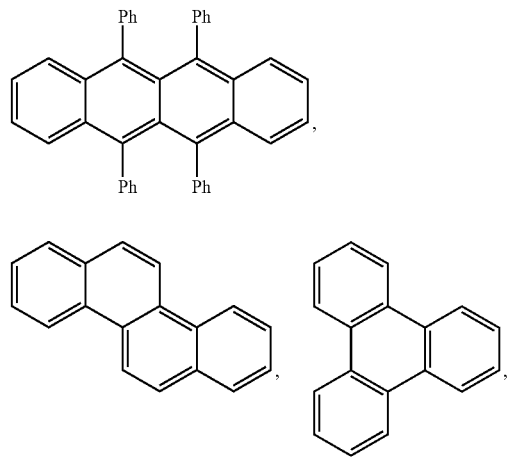

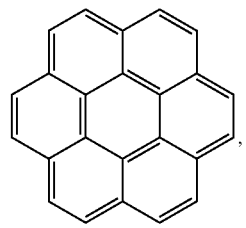

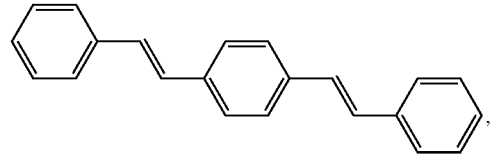

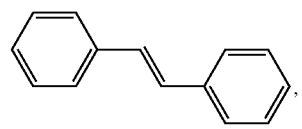

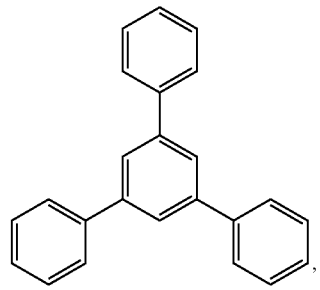

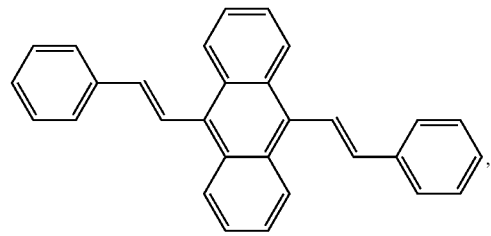

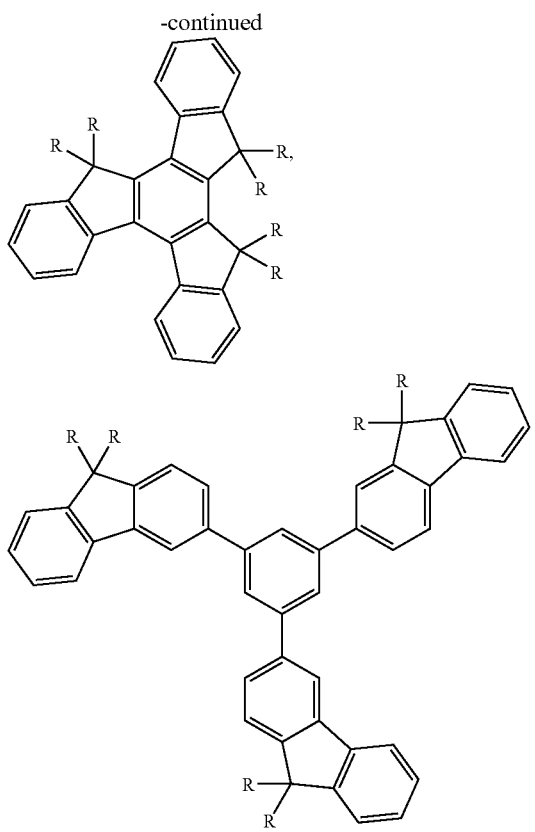

or the like that is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof.

In some embodiments, $Ar^1$ is a trivalent radical of benzene.

The compounds according to Formula I contain a divalent radical E that is a $C_{3-60}$ heteroarylene having at least one —C═N— unit. The heteroarylene can be unsubstituted or substituted with one or more alkyl, alkenyl, alkoxy, aryl, aryloxy, fluoro, fluoroalkyl, perfluoroalkyl, heteroalkyl, heteroaryl, or combinations thereof. The —C═N— unit tends to be more electron deficient compared to a carbon-carbon double bond and tends to enhance the capabilities of the disclosed compounds to function as electron transport agents.

Suitable E groups can include, for example, a radical of oxadiazole, N-substituted triazole, N-substituted imidazole, benzoimidazole, N-substituted pyrazole, oxazole, isoxazole, thiazole, thiadiazole, benzothiadiazole, isothiazole, pyridine, pyridazine, pyrimidine, pyrazine, triazine, tetrazine, benzoxazole, benzothiazole, quinoline, isoquinoline, cinnoline, quinazoline, quinoxaline, phthalazine, benzotriazine, phenazine, phenanthridine, acridine, or the like.

In some embodiments, E includes a radical of benzoimidazole, oxadiazole, thiadiazole, or triazole. In some embodiments, E includes a radical of oxadiazole.

In Formula I, G is a monovalent radical selected from hydrogen, $C_{1-30}$ alkyl, $C_{1-30}$ heteroalkyl, $C_{3-60}$ heteroaryl, $C_{6-60}$ carbocyclic aryl, or $C_{18-60}$ tertiary aromatic amino aryl that is unsubstituted or substituted with one or more alkyl, alkenyl, alkoxy, aryl, aryloxy, fluoro, fluoroalkyl, perfluoroalkyl, heteroalkyl, heteroaryl, or combinations thereof.

In some of the disclosed compounds, the group G can be hydrogen or a monovalent radical of an alkane or heteroalkane. The alkanes can be straight, branched, or cyclic. Suitable $C_{3-30}$ alkanes include, but are not limited to, n-propane, n-butane, n-pentane, tert-butane, iso-propane, iso-butane, n-octane, n-heptane, cyclopentane, cyclohexane, adamantane, ethylhexane, decane, dodecane, hexadecane, octadecane, and icosane. Suitable $C_{3-30}$ heteroalkanes include one or more heteroatoms selected from S, O, N, P, and Si. The heteroalkanes, for example, can be ethers or thioethers. In some embodiments, the heteroalkane includes a poly(oxyalkylene) segment of formula —O($C_mH_{2m}$O)$_y$— or a poly(dialkylsiloxane) segment of formula —[Si($C_wH_{2w+1}$)$_2$O]$_y$— where w is an integer of 1 to 10, y is an integer of 2 to 20, and m is an integer of 1 to 6. The alkane or heteroalkane can be unsubstituted or substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, a $C_{3-20}$ heteroaryl, and combinations thereof.

The group G can be, in some compounds, a $C_{6-60}$ carbocyclic aryl that is a monovalent radical of

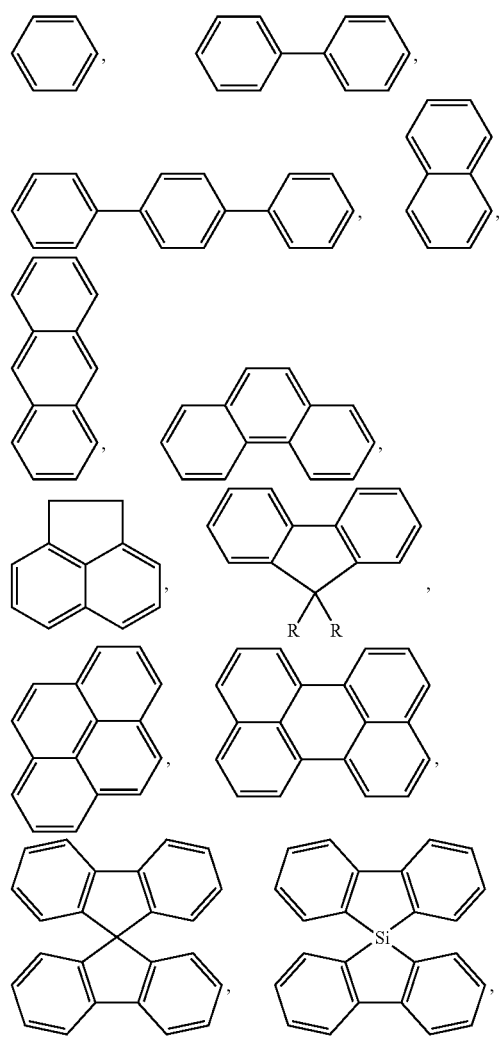

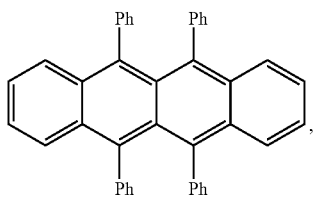

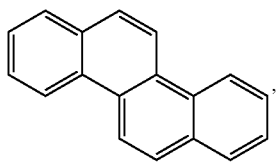

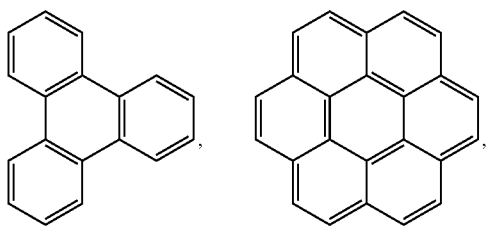

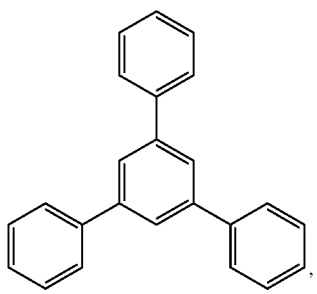

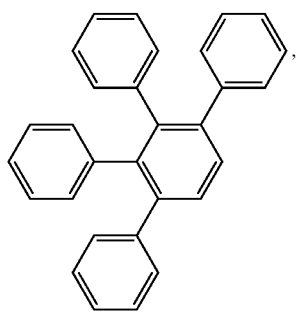

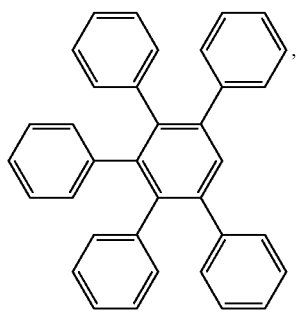

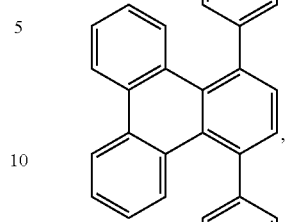

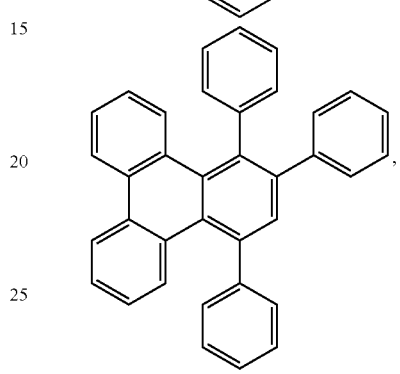

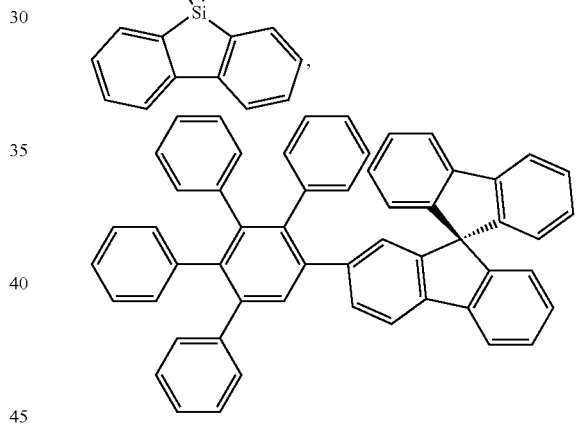

or the like that is unsubstituted or substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, a $C_{3-20}$ heteroaryl, and combinations thereof. In some compounds of the invention, the presence of such a group for D can impart light emitting characteristics to the compounds.

The group G can be a $C_{3-60}$ heteroaryl. In some embodiments, the heteroaryl contains at least one —C=N— unit. A —C=N— unit is typically more electron deficient compared to a carbon-carbon double bond. The presence of such a group tends to further enhance the electron transport capabilities of the compounds of Formula I. Suitable $C_{3-60}$ heteroaryls that contain at least one —C=N— unit can be a monovalent radical of

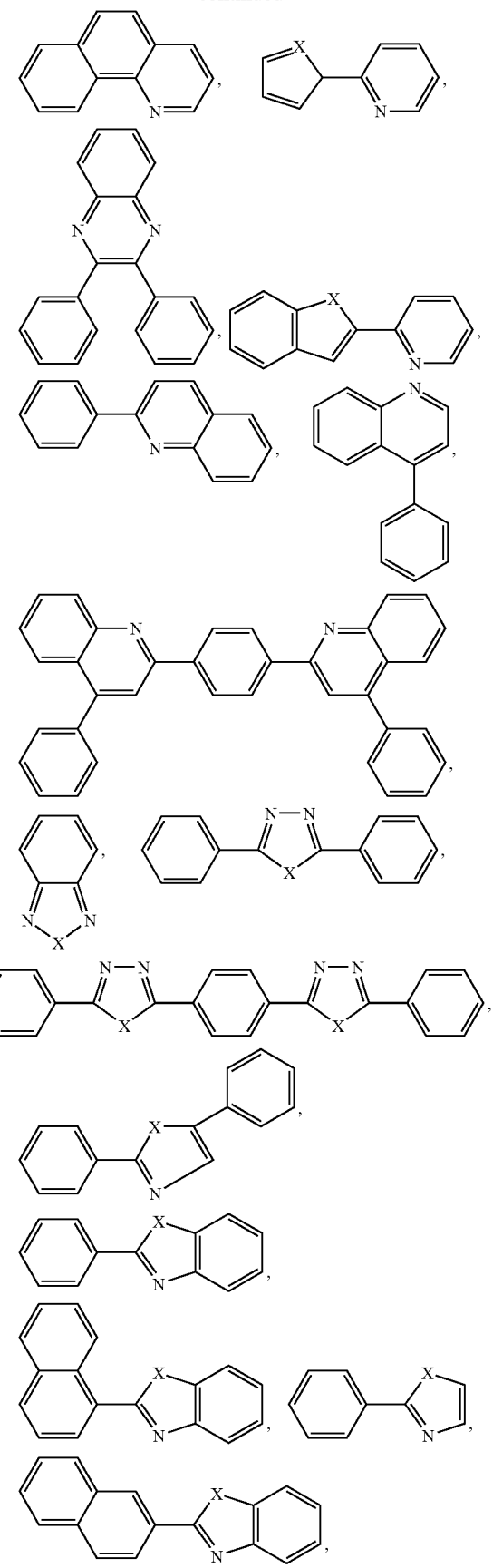

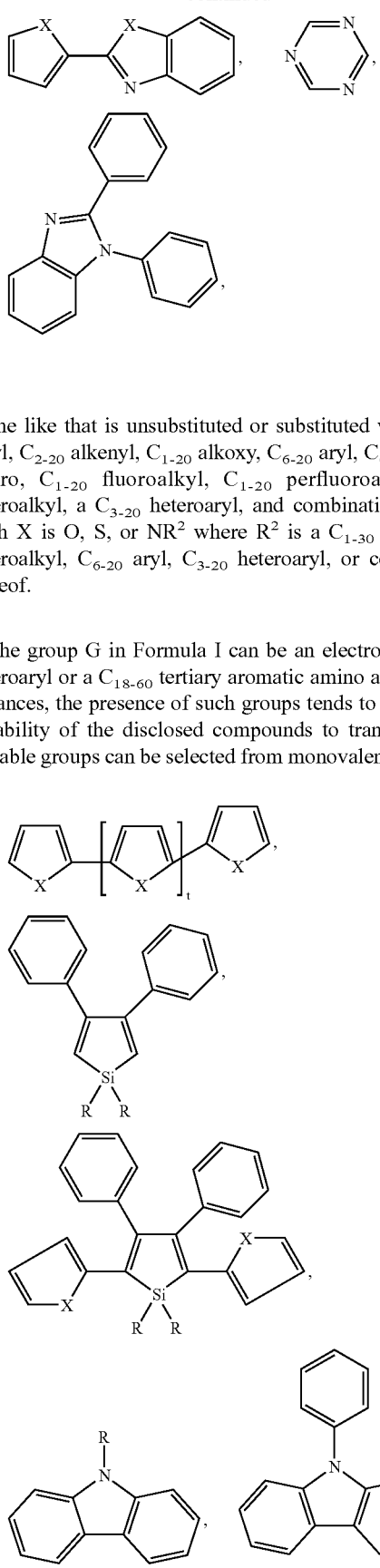

or the like that is unsubstituted or substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, a $C_{3-20}$ heteroaryl, and combinations thereof. Each X is O, S, or $NR^2$ where $R^2$ is a $C_{1-30}$ alkyl, $C_{1-30}$ heteroalkyl, $C_{6-20}$ aryl, $C_{3-20}$ heteroaryl, or combinations thereof.

The group G in Formula I can be an electron rich $C_{3-60}$ heteroaryl or a $C_{18-60}$ tertiary aromatic amino aryl. In some instances, the presence of such groups tends to enhance the capability of the disclosed compounds to transport holes. Suitable groups can be selected from monovalent radicals of

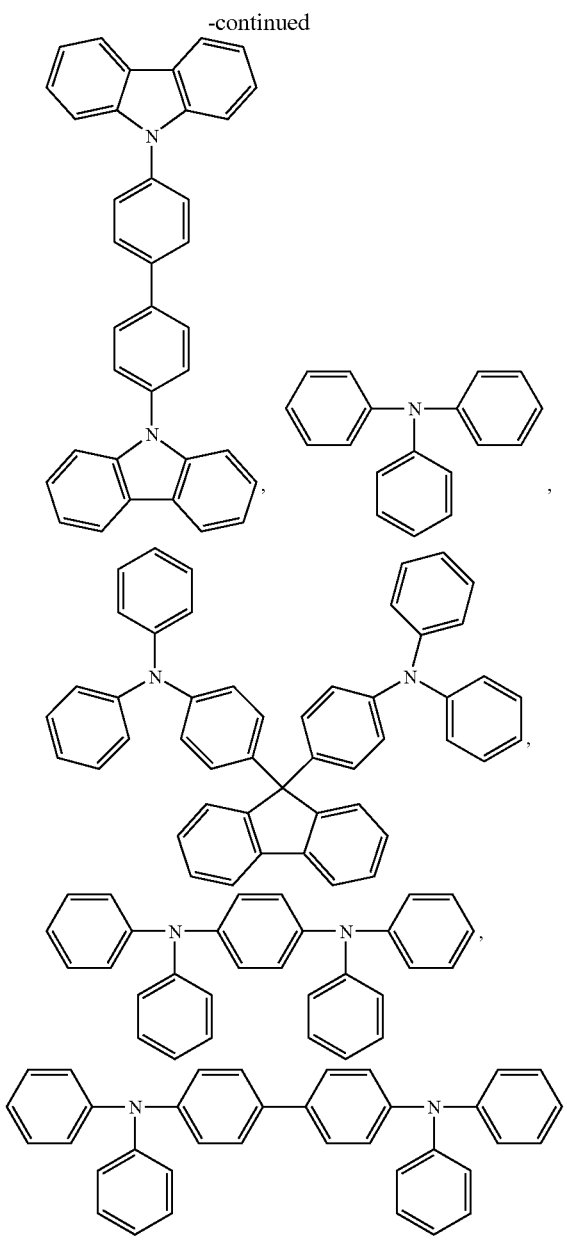

and the like that are unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof. Each t is an integer of 0 to 4.

The group J in Formula I can be a monovalent radical Of $C_{1-30}$ alkyl, $C_{1-30}$ heteroalkyl, $C_{3-60}$ heteroaryl, $C_{6-60}$ carbocyclic aryl, or a $C_{18-60}$ tertiary aromatic amino aryl that is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. The group J can be the same or different than group G in Formula I. When there is only one end capping group (i.e., n is equal to 1 in Formula I), no more than one of J and D can be a phenyl that is unsubstituted. In some compounds, the phenyl is substituted with a sterically hindered group selected from an alkyl, alkenyl, alkoxy, aryl, aryloxy, fluoroalkyl, perfluoroalkyl, heteroalkyl, heteroaryl, and a combination thereof. In some embodiments, when there is only one end capping group, no more than one of J and D can be a phenyl that is unsubstituted or substituted.

The group J can be, in some compounds of the invention, a monovalent radical of an alkane or heteroalkane. The alkanes can be straight chained, branched, or cyclic. Suitable $C_{3-30}$ alkanes include, but are not limited to, n-propane, n-butane, n-pentane, tert-butane, iso-propane, iso-butane, cyclopentane, cyclohexane, adamantane, n-octane, n-heptane, ethylhexane, decane, dodcecane, hexadecane, octadecane, and icosane. Suitable $C_{3-30}$ heteroalkanes include one or more heteroatoms selected from S, O, N, P, and Si. The heteroalkanes, for example, can be ethers or thioethers. In some embodiments, the heteroalkane includes a poly(oxyalkylene) segment of formula $-O(C_mH_{2m}O)_y-$ or a poly(dialkylsiloxane) segment of formula $-[Si(C_wH_{2w+1})_2O]_y-$ where w is an integer of 1 to 10, y is an integer of 2 to 20, and m is an integer of 1 to 6. The alkane or heteroalkane can be unsubstituted or substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, a $C_{3-20}$ heteroaryl, and combinations thereof.

In some compounds of Formula I, group J can be a $C_{6-60}$ carbocyclic aryl that is a monovalent radical of

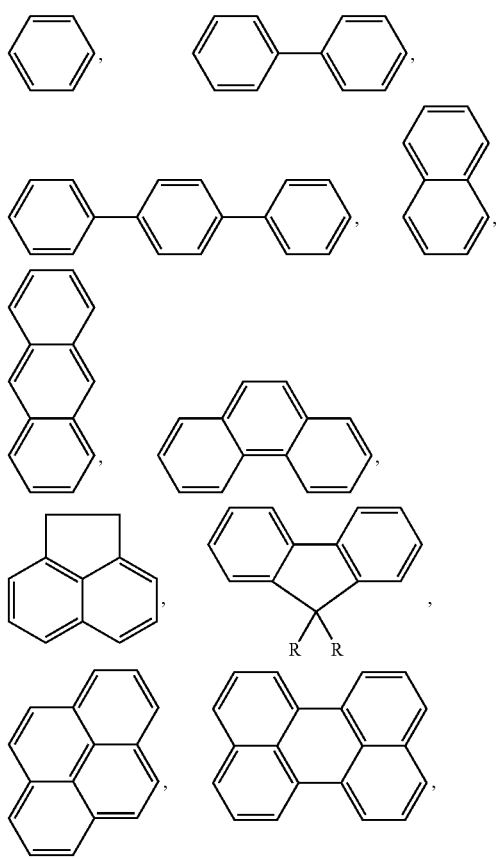

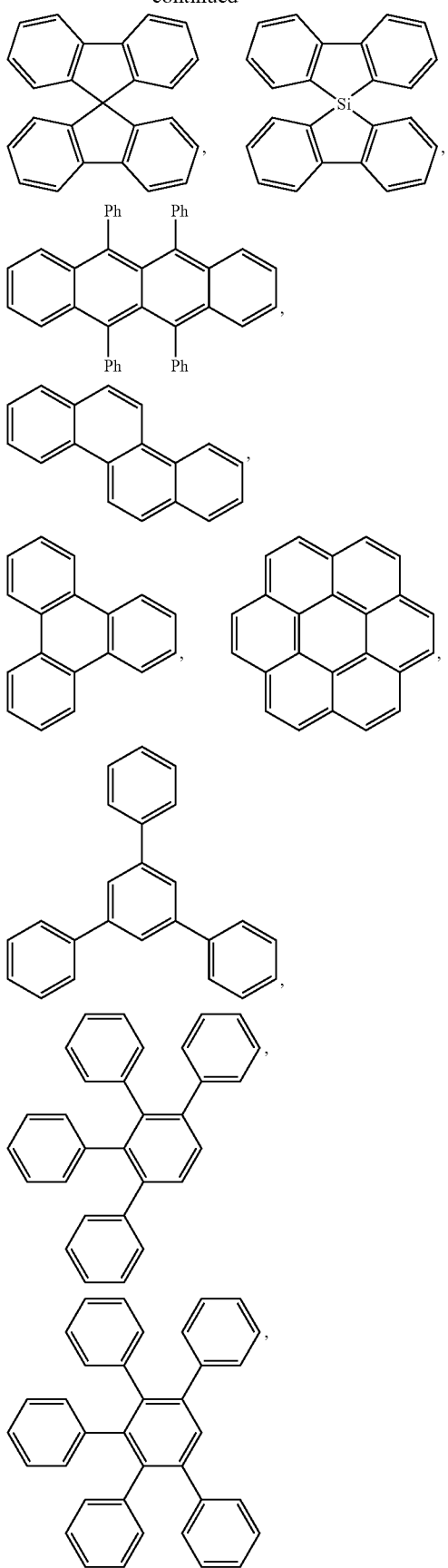

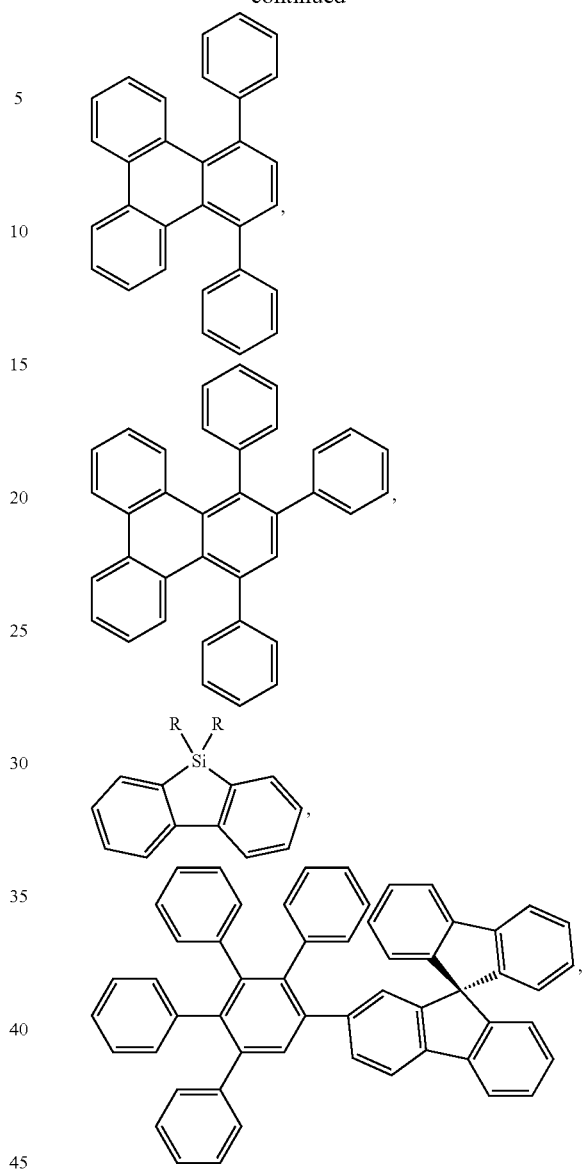

or the like that is unsubstituted or substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, or combinations thereof. Each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof.

The group J can also be a $C_{3-60}$ heteroaryl. In some embodiments, the heteroaryl contains at least one —C=N— unit. A —C=N— unit is typically more electron deficient than a carbon-carbon double bond and the presence of such a group tends to further enhance the electron transport capabilities of the disclosed compounds. Suitable $C_{3-60}$ heteroaryls that contain at least one —C=N— unit can be a monovalent radical of

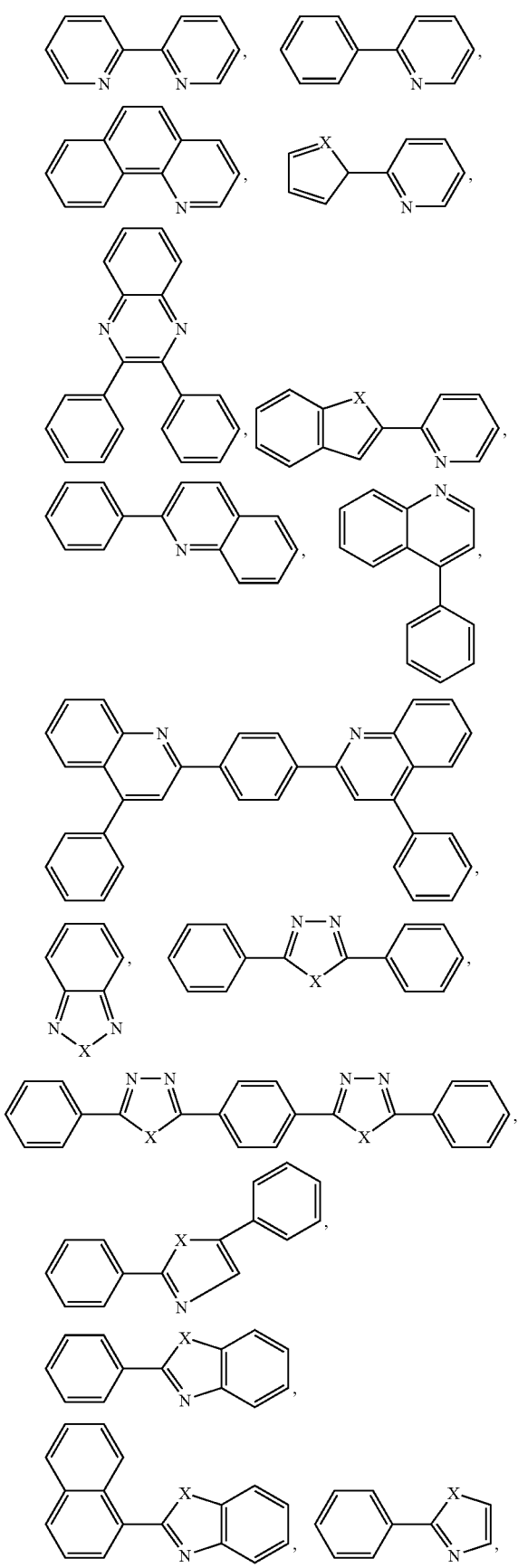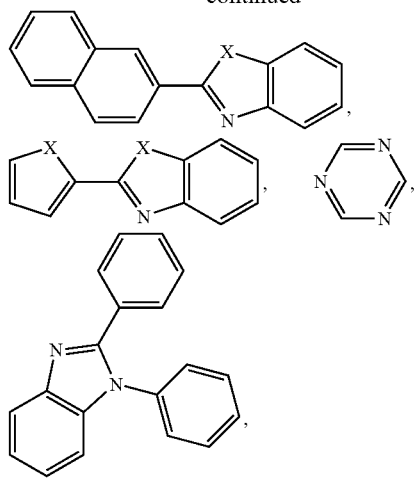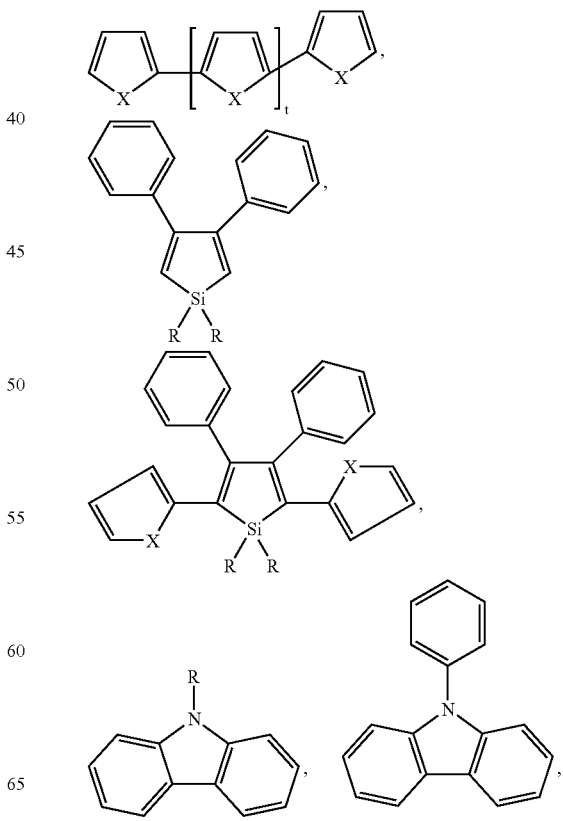

or the like that is unsubstituted or substituted with a $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, a $C_{3-20}$ heteroaryl, and combinations thereof. Each X is O, S, or $NR^2$ where $R^2$ is a $C_{1-30}$ alkyl, $C_{1-30}$ heteroalkyl, $C_{6-20}$ aryl, $C_{3-20}$ heteroaryl, or combinations thereof.

The group J in Formula I can also be an electron rich $C_{3-60}$ heteroaryl or a $C_{18-60}$ tertiary aromatic amino aryl. In some instances, the presence of such a group tends to enhance the capability of the compounds of the invention to transport holes. Suitable electron rich groups can be selected from monovalent radicals of -continued

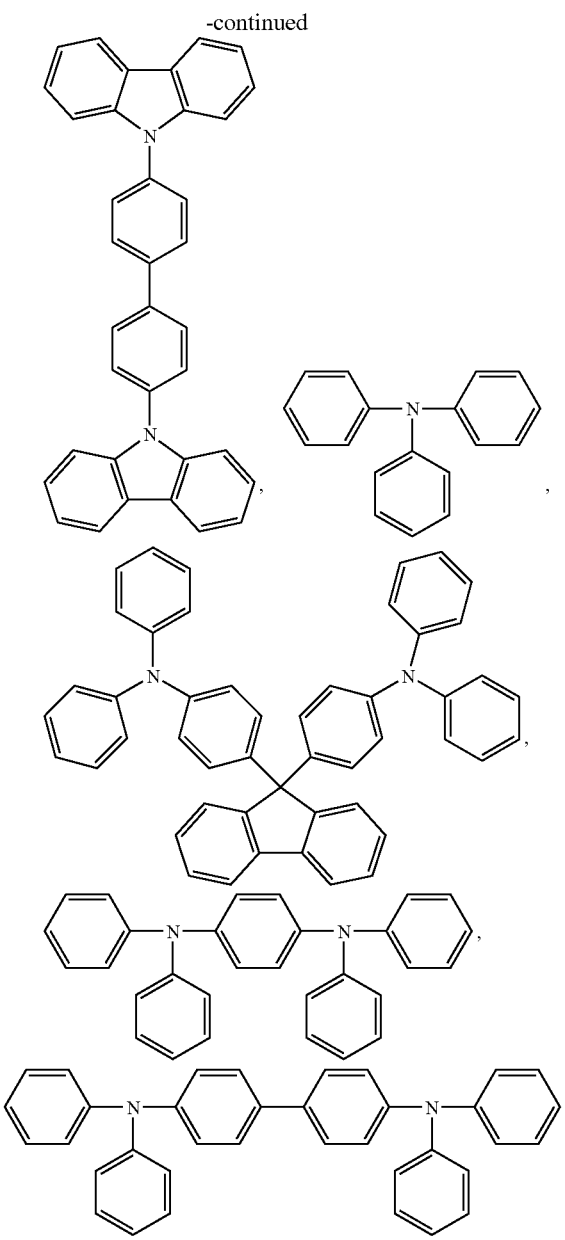

or the like that are unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof. Each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof. Each t is an integer of 0 to 4. Each X is O, S, or $NR^2$ where $R^2$ is a $C_{1-30}$ alkyl, $C_{1-30}$ heteroalkyl, $C_{6-20}$ aryl, $C_{3-20}$ heteroaryl, or combinations thereof.

Any R group in the compounds of the invention can include a divalent poly(oxyalkylene) soft segment of Formula V $$*-O(C_mH_{2m}O)_y-*$$ V or a divalent poly(dialkylsiloxane) soft segment of Formula VI $$*-[Si(C_wH_{2w+1})_2O]_y-*$$ VI where m is an integer of 1 to 6, y is an integer of 2 to 20, and w is an integer of 1 to 10. In some embodiments, the poly(oxyalkylene) or poly(dialkylsiloxane) soft segment can be connected to an alkyl, aryl, or heteroaryl group. The substituent can, for example, have Formula VII $$*-[Ar]_v-SS-R''$$ VII where SS is a poly(oxyalkylene) or poly(dialkylsiloxane) soft segment, Ar is an arylene group, v is an integer of 0 or 1, and R'' is an aryl, heteroaryl, or a alkyl. In some examples, R'' is a sterically hindered group. Groups according to Formula VIII can reduce the formation of intermolecular or intramolecular configurations that produce undesirable excimer or exciplex emission.

Any R group in the disclosed compounds can include a fluoro, $C_{1-30}$ fluoroalkyl, $C_{1-30}$ perfluoroalkyl, or a combination thereof. These groups can improve the solubility and the film forming properties of the compounds, can increase the ionization potential and electron affinity of the compounds, or a combination thereof. Compounds having an increased ionization potential and electron affinity can more easily inject electrons and block holes when used in organic electroluminescent devices. Fluoro, fluoroalkyl, or perfluoroalkyl groups can also lower the vapor pressure of the compounds and make them easier to vapor deposit.

In some embodiments of Formula I, the various groups D, $Ar^1$, G, J, or a combination thereof can be selected to provide a high bandgap between the highest occupied molecular orbital (HOMO) and the lowest unoccupied molecular orbital (LUMO). As used herein, high bandgap refers to an energy difference between the HOMO and LUMO of at least 2.5 eV. In some embodiments, the energy difference is at least 3 eV. A high bandgap tends to make the compound suitable for use as a blue light emitting material or as a host material for other light emitting material.

This large bandgap between the HOMO and LUMO can be particularly advantageous when a high bandgap molecule is desired for use as an electron transport agent, as a hole blocker, as a molecular host for molecular or polymeric emitters, or as a blue emitting electroluminescent molecule. Some compounds include, for example, carbocyclic aromatic groups. Such groups can, in some instances, be sufficiently sterically hindering to reduce the formation of intermolecular or intramolecular configurations that produce excimer or exciplex emission that can cause color shifting of the electroluminescence.

Some group can facilitate or provide hole transport, electron transport, or a combination thereof. Such groups include, for example, tertiary aromatic amino aryl groups and electron rich heteroaromatic groups. The use of such groups can balance the hole and electron transport efficiencies, or tune the ionization potential and/or electron affinity of the compounds of the invention. Such groups can enhance or modify the band gap and/or electroluminescent character of the compound. The groups can be used, for example, to tune the color of the emitting light of the compound or other compounds in a composition. Certain heteroaryl and tertiary aromatic amino aryl groups can provide compounds that have emissions in the red, green, or blue regions of the visible spectrum.

Exemplary compounds of the invention where n is equal to 1 include, but are not limited to
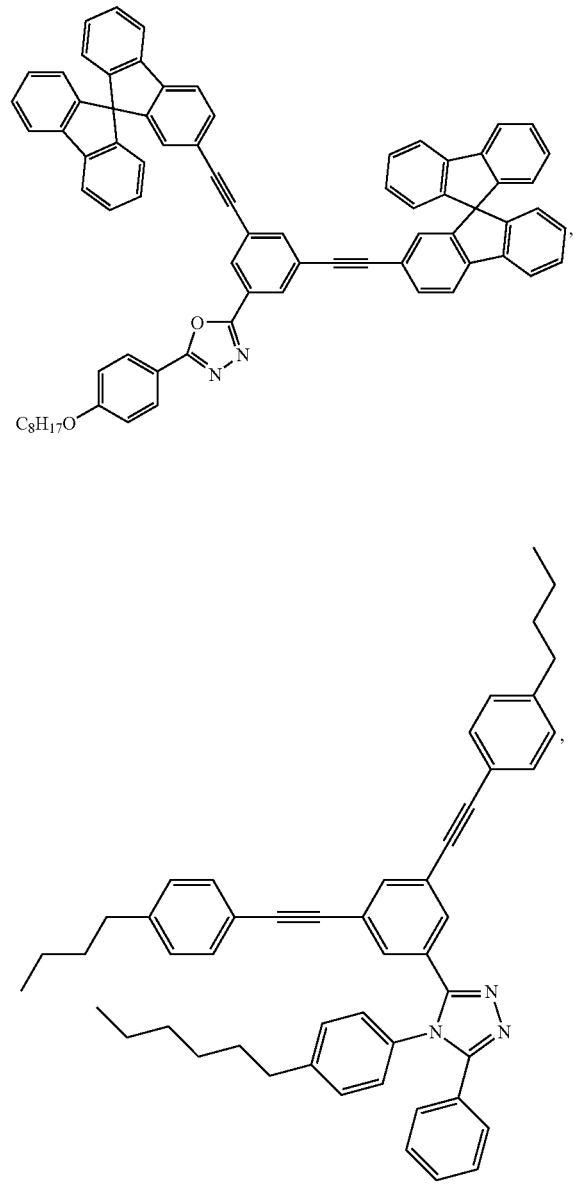
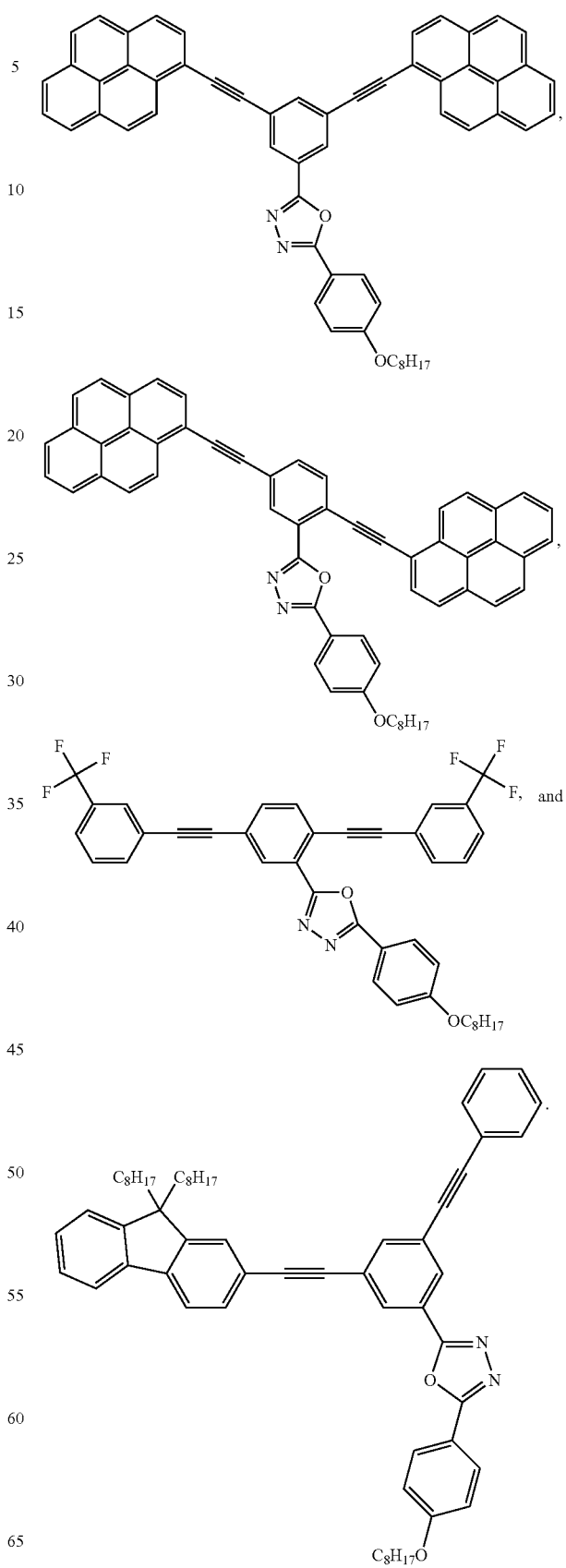

Exemplary compounds of the invention where n is equal to 2 include, but are not limited to
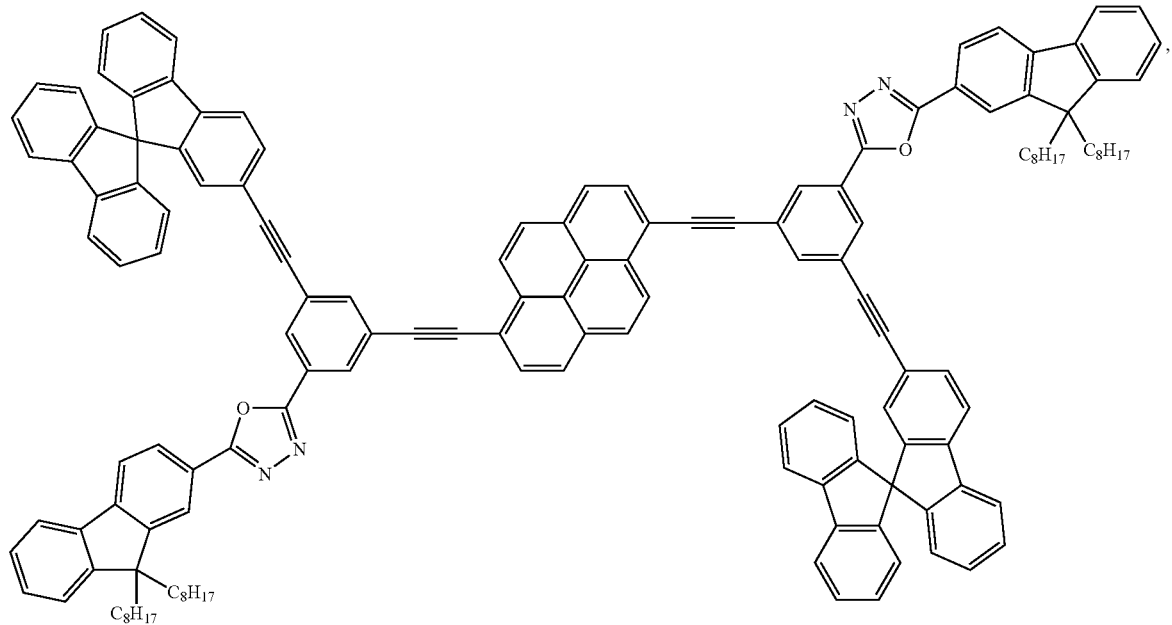
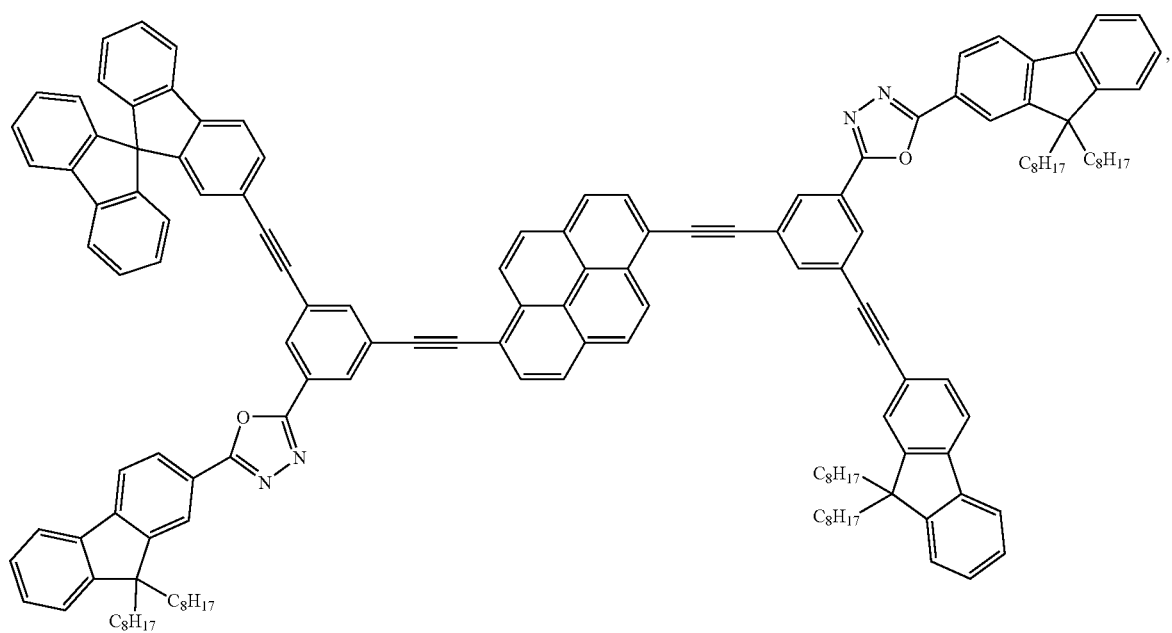

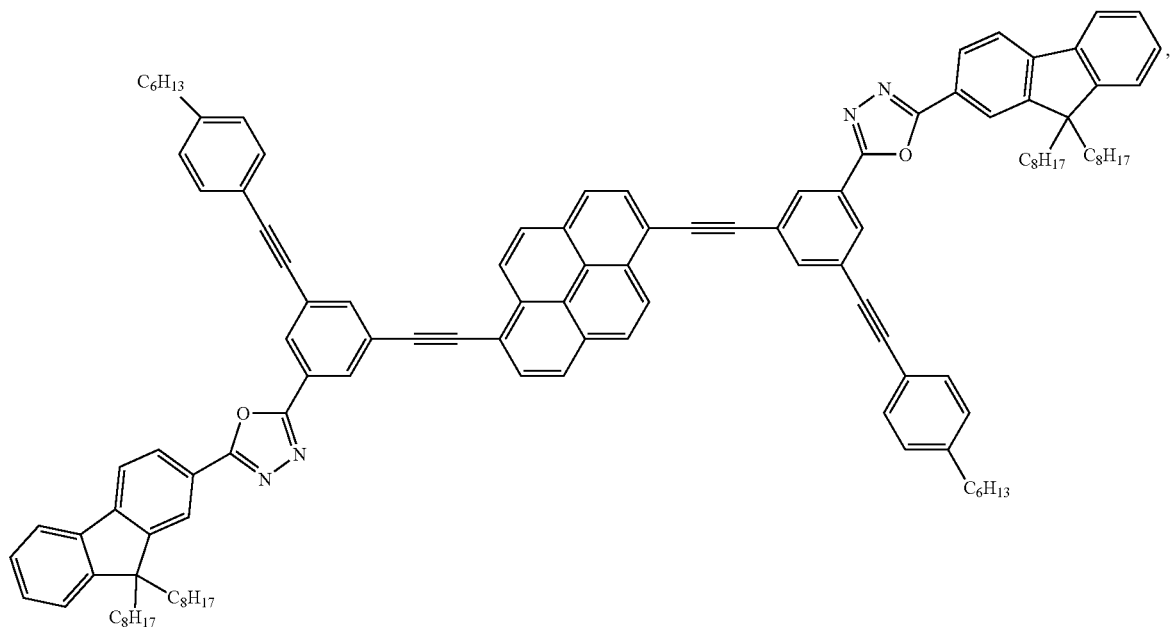
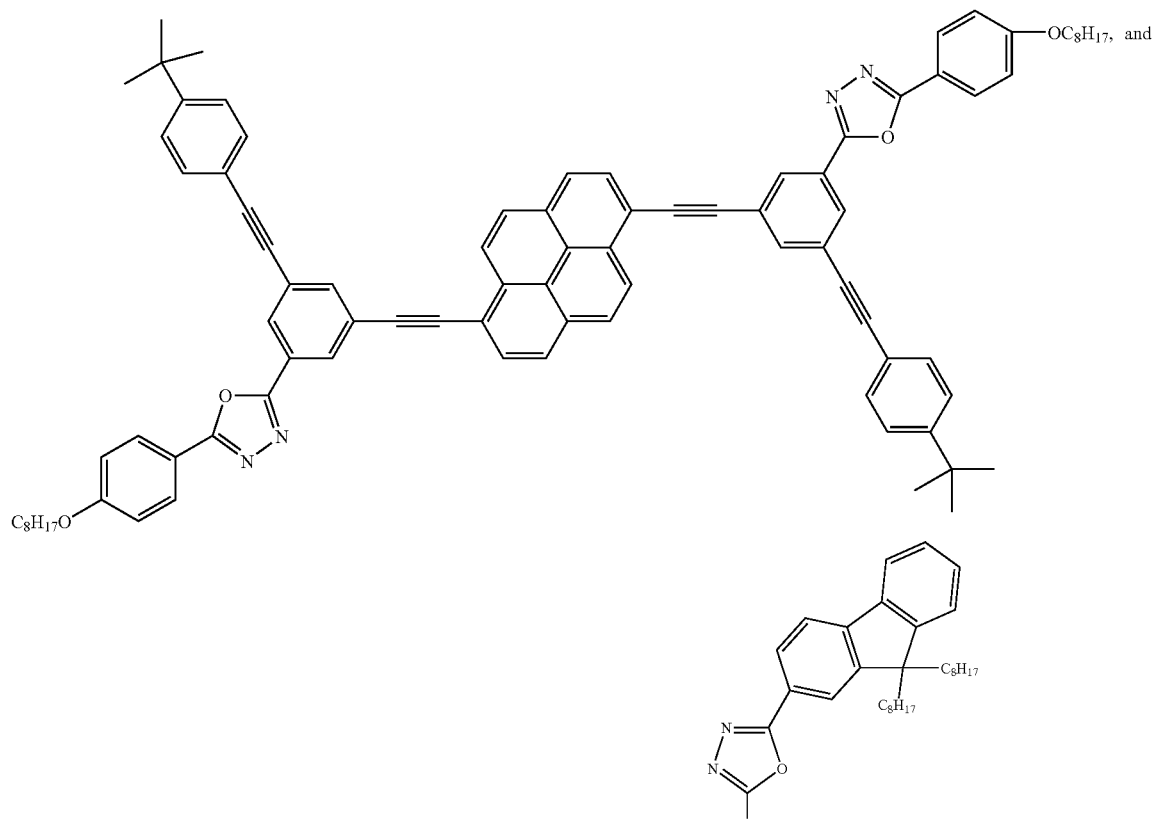

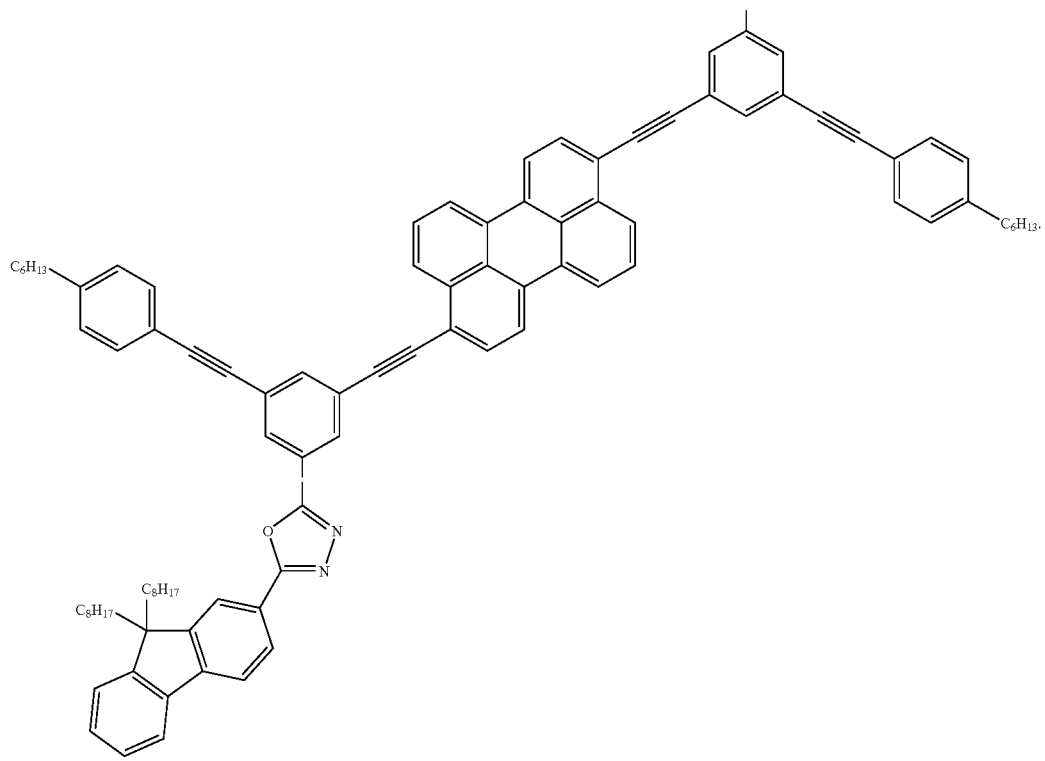
An exemplary compound where n is equal to 3 includes, but is not limited to,
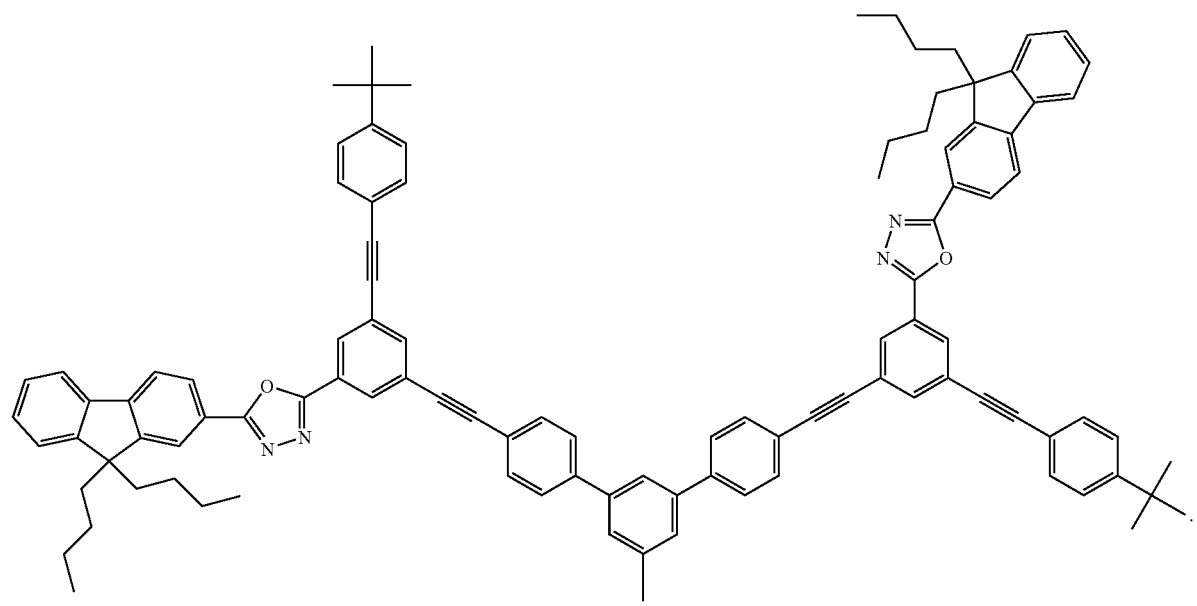

-continued
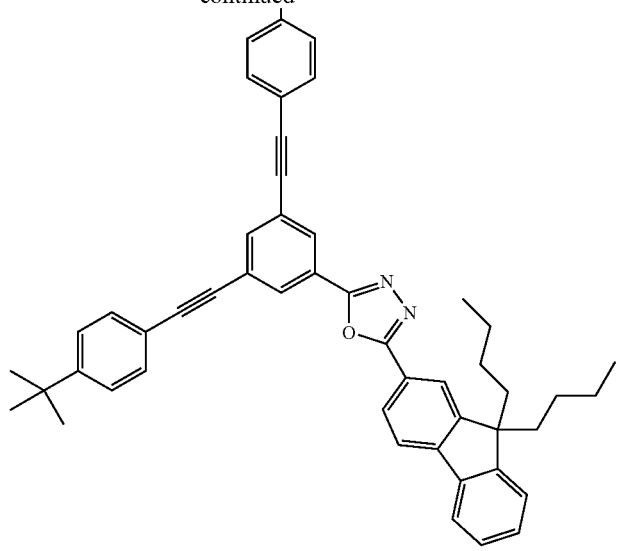
Exemplary compounds where n is equal to 4 include, but are not limited to,
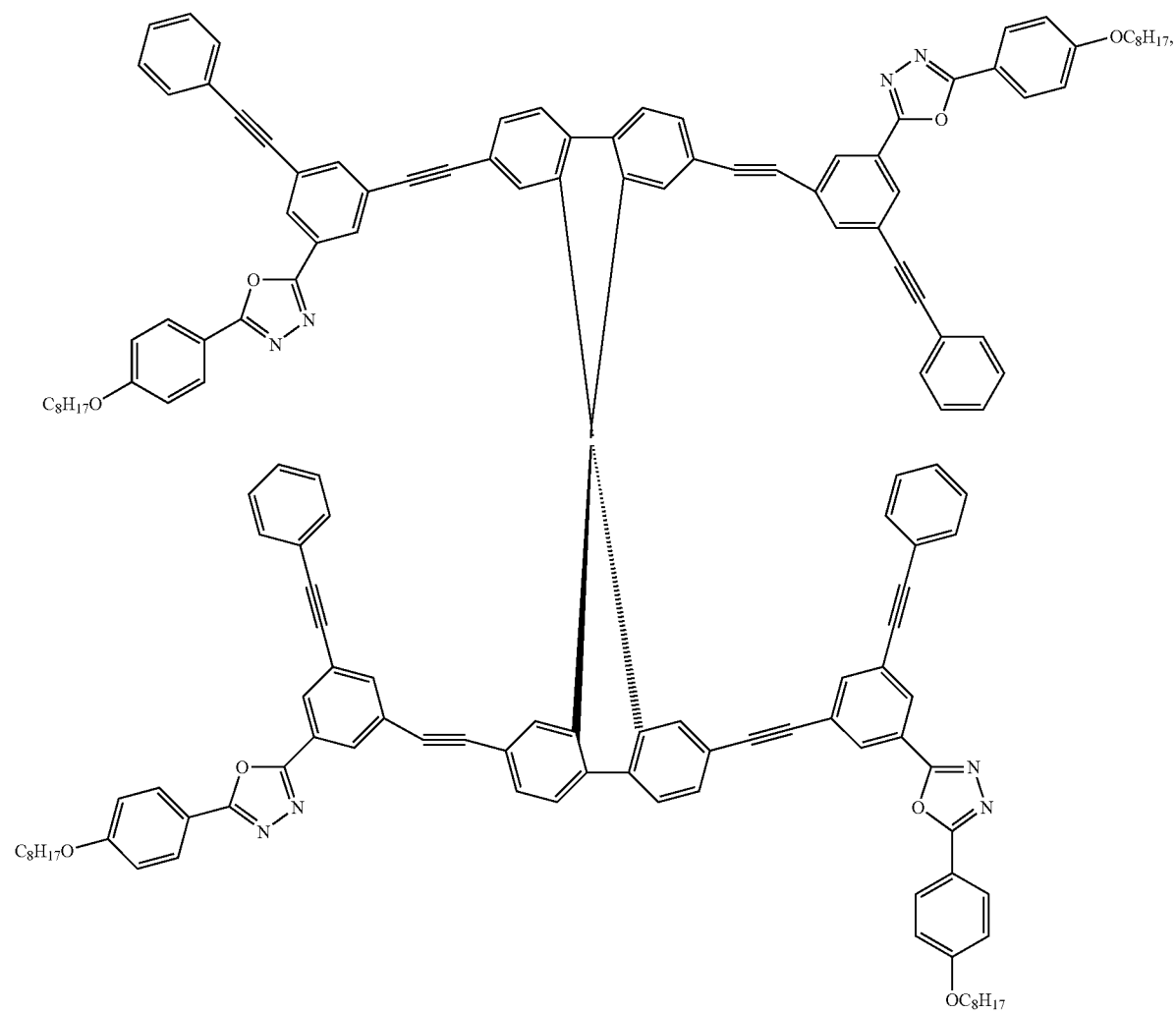

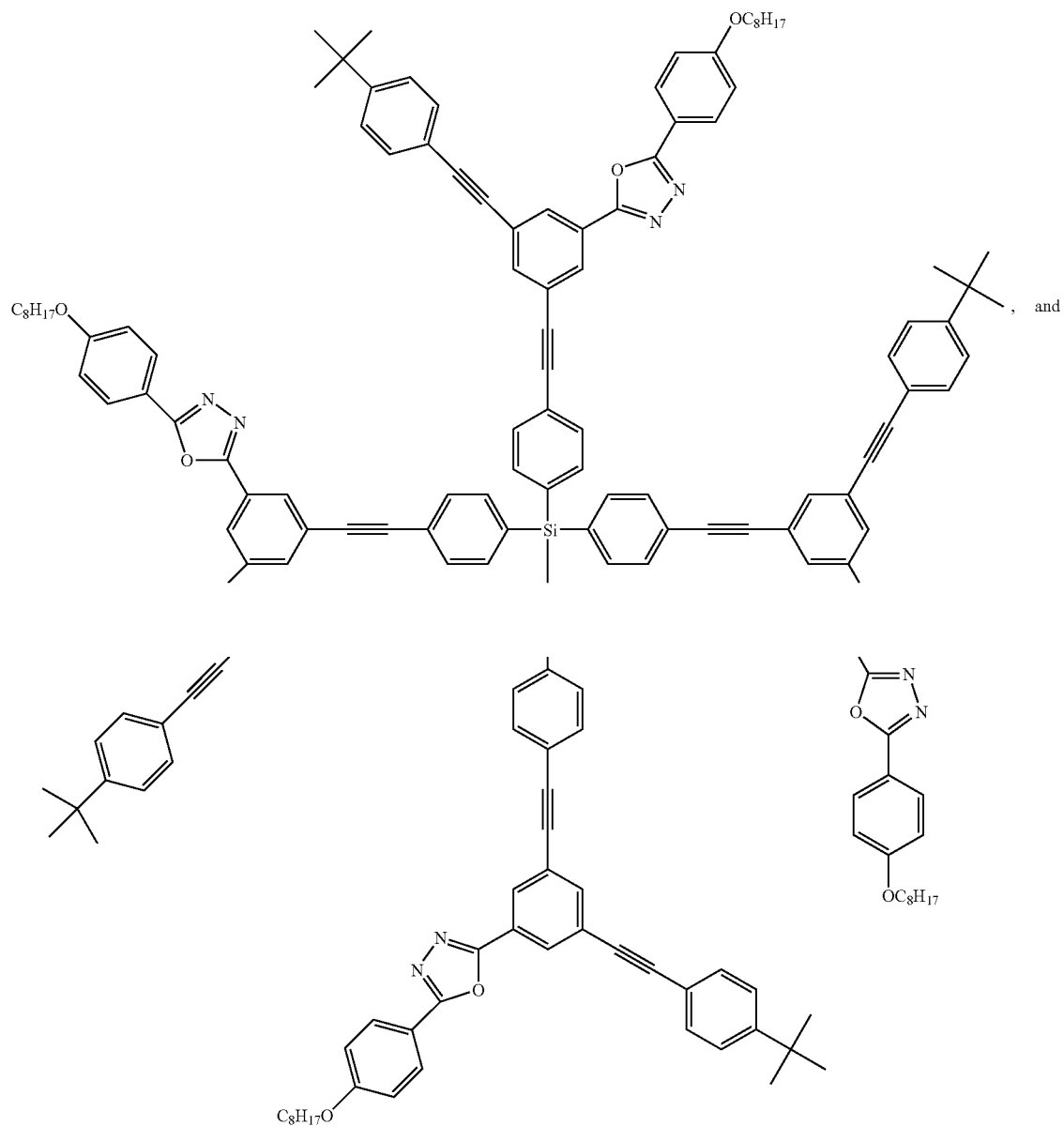

-continued

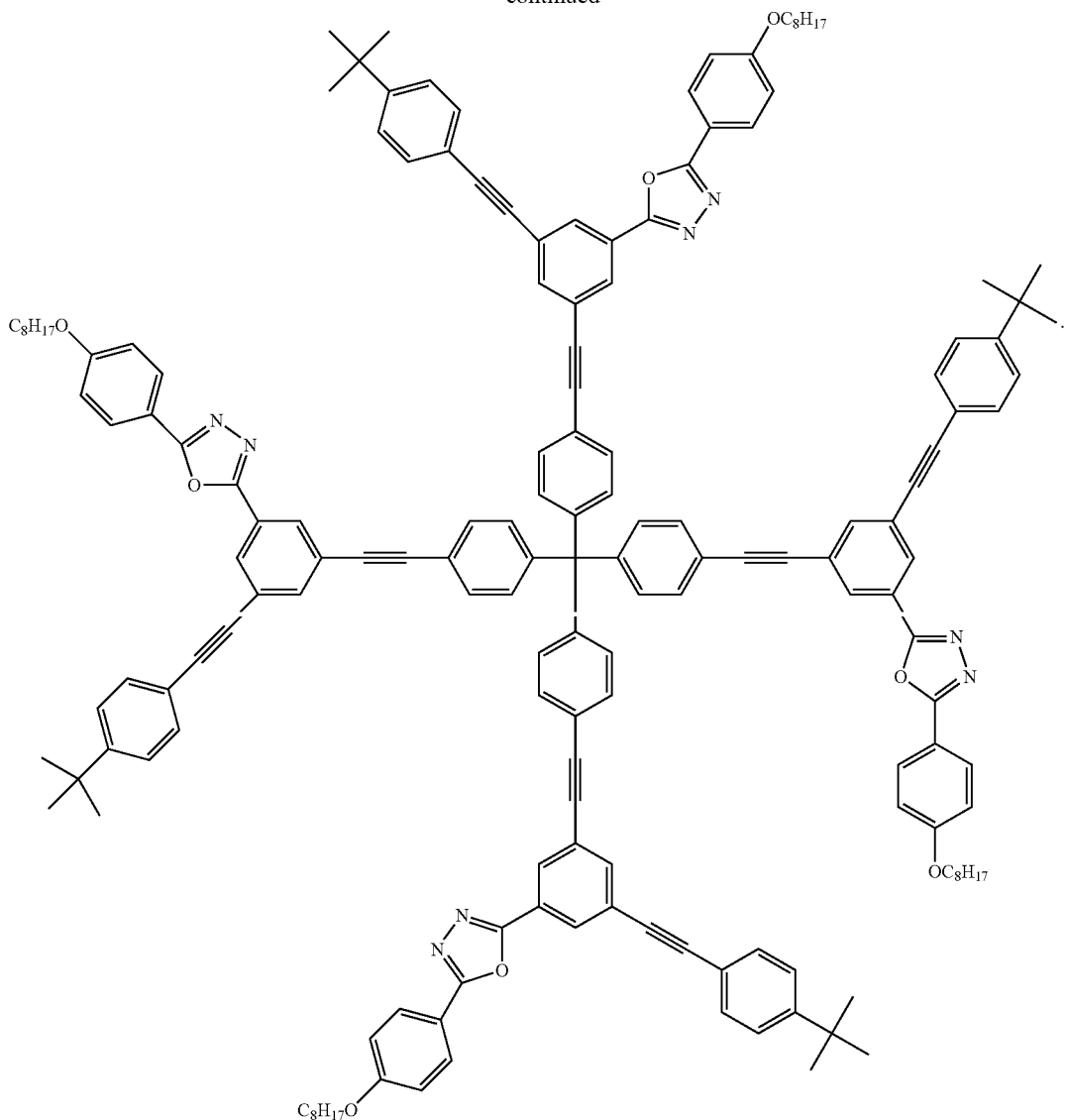

Compounds of the present invention can be prepared from building blocks of Formula CCC:

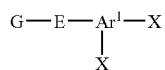

where $Ar^1$, E, and G are as previously described and X represents halogen atoms. Typically the halogens are bromine atoms, iodine atoms, or a combination thereof. Compounds of Formula CCC includes a wide variety of dihalogenated heteroaromatic compounds. For example, the compounds can contain a radical of 1,3,4-oxadiazole, 1,3,4-thiadiazole, 1,3,4-triazole, and the like.

Dihalogenated compounds of Formula CCC can be made by a wide variety of methods, a number of which will be exemplified here.

The compounds 2-(dihaloaryl)benzoxazoles (CCCII), 2-(dihaloaryl)benzothiazoles (CCCIII), and 1-(dihaloaryl)-1,2-diphenyl-1H-benzoimidazole (CCCIV) are a subgenus of the Formula CCC where G—E is benzoxazol-2-yl, benzothiazol-2-yl, and 1-phenyl-benzimdazol-2-yl heteroaryls, respectively. Such groups can be prepared by polyphosphoric acid (PPA) promoted cyclocondensation of aromatic acid CCCI with 2-aminothiophenol, 2-aminophenol, and N-phenyl-1,2-phenylenediamine, respectively as shown in Reaction Scheme I. Group G is a hydrogen in this reaction scheme. However, the aromatic ring can be substituted to provide another group G.

The reaction of N-phenyl-benzene-1,2-diamine with benzoic acid to give 1,2-diphenyl-1H-benzoimidazole has been demonstrated with triflic anhydride/triphenylphosphine oxide in $CH_2Cl_2$ and 1,2-dichloro-ethane (Takeda et al., *J. Org. Chem.*, 52 (18), 4137–4139 (1987)). Other dinucleophiles useful for the synthesis of compounds of Reaction Scheme I include $N^2$-p-tolyl-naphthalene-1,2-diyldiamine (Fischer, *Chem. Ber.*, 25, 2826–2846 (1892)), 1-amino-naphthalen-2-ol (Barton et al., *Tetrahedron Lett.*, 24 (15) 1601–1604 (1983)), and 1-amino-naphthalene-2-thiol (Kajino et al., *Chem. Pharm. Bull.*, 39 (11), 2888–2895 (1991)).

Reaction Scheme I

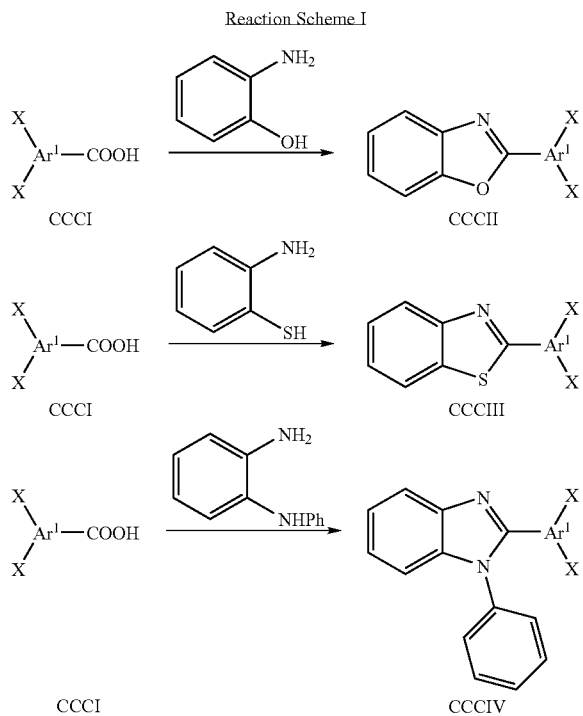

Dihalogenated 1,3,4-oxadiazole building blocks CCCVII are a subgenus of Formula CCC where Ar¹, G, and X are as previously defined and E is the 1,3,4-oxadiazol-2,5-diyl moiety. Compounds CCCVII can be synthesized by the acylation of substituted tetrazoles CCCV as shown in Reaction Scheme II. In Reaction Scheme II, a dihaloaroyl chloride CCCVI is reacted with a substituted tetrazole CCCV by heating for about 12 hours in an inert solvent such as pyridine (Myznikov et al., *J. Gen. Chem. of USSR*, 62 (6), 1125–1128 (1992)) to form the dihalogenated oxadiazole compound CCVII. The tetrazole of CCCV can be prepared by reaction of the corresponding nitrile with $NaN_3$ and $NH_4Cl$ in N,N-dimethylformamide (DMF) at reflux.

Reaction Scheme II

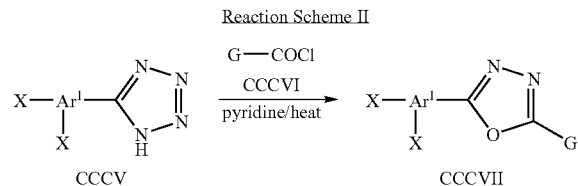

Alternatively, compounds CCCVII can be prepared by cyclocondensation of benzoylaroylhydrazides as shown in Reaction Scheme III. (Grekov et al., *J. Gen. Chem. USSR* (*Engl. Transl.*), 30, 3763–3766 (1960)) where Ar¹, G, E, and X are as defined above. In Reaction Scheme III, a dihaloaroyl hydrazide CCCVIII is reacted with a substituted benzoyl chloride CCCIX at room temperature in dichloromethane with one equivalent of triethylamine to form a benzoylaroylhydrazide CCCX. Alternatively, a dihaloaroyl chloride CCCXII is reacted with a substituted benzoyl hydrazide compound CCCXI to form the benzoylaroylhydrazide CCCX. Finally the benzoylaroylhydrazide CCCX is reacted with phosphorus oxychloride at reflux to form the dihalogenated oxadiazole compound CCCVII.

Reaction Scheme III

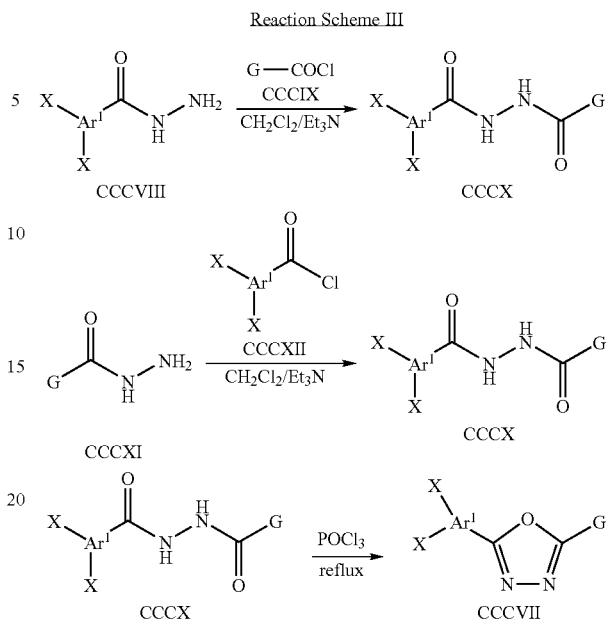

Dihalogenated 1,3,4-thiadiazole compounds CCCXII-a, which are subgenus of Formula CCC where Ar¹, G, and X are as previously defined and E is the 1,3,4-thiadiazol-2,5-diyl heteroaromatic group. These can be prepared by cyclocondensation of a benzoylaroylhydrazide intermediates as shown in Reaction Scheme IV (A. T. Prudchenko, *J. Gen. Chem. USSR* (*Engl. Transl.*). 37, 2082–2084(1967)). In Reaction Scheme IV the benzoylaroylhydrazide intermediate of Formula CCCX is reacted with $P_2S_5$ to provide the 1,3,4-thiadiazoles CCCXII.

Reaction Scheme IV

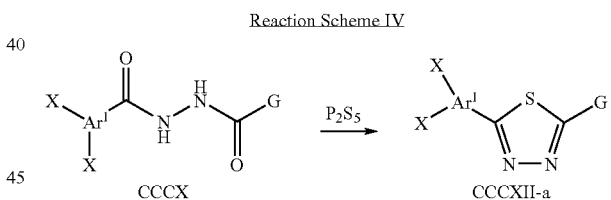

Dihalogenated 1,3,4-triazole compounds CCCXIII, which are a subgenus of Formula CCC, can be prepared by cyclocondensation of the benzoylaroylhydrazide intermediates as shown in Reaction Scheme V (E. Klingsberg, *J. Org. Chem.*, 23, 1086(1958)) where Ar¹, G, and X are as previously defined. The group E in Formula CCC is a 1,3,4-triazolyl radical. In Reaction Scheme V, the benzoylaroylhydrazide intermediate CCX is reacted with phosphorus trichloride at an elevated temperature, e.g., 150° C., in the presence of $RNH_2$, (wherein R is alkyl, aryl, heteroaryl, or heteroalkyl) to provide the 1,3,4-triazole CCCXIII. Alternatively, the benzoylaroylhydrazide CCCX is reacted with chlorine in glacial acetic acid (Moss et al., *J. Chem. Soc. Perkin Trans.*, 1 (9), 1999–2006 (1982)) or other non-reactive solvents to form compound CCCXIV. The compound CCCXIV is reacted with $RNH_2$ (Gautun et al., *Acta Chem. Scand.*, 45(6), 609–615 (1991)) to provide the corresponding 1,3,4-triazoles CCCXIII.

Reaction Scheme V

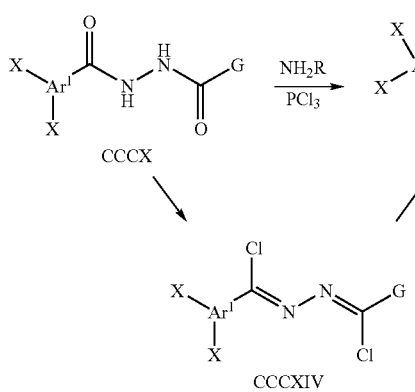

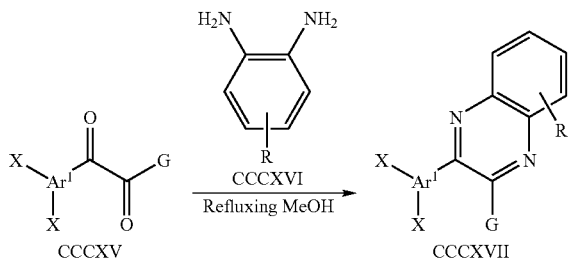

Dihalides CCCXVII are a subgenus of Formula CCC where $Ar^1$, G, and X are as previously defined and E is the quinoxalin-2,3-diyl moiety. Intermediate CCCXVII can be made by refluxing the 1,2-phenylenediamine CCCXVI with compound CCCXV in methanol (Amashukeli et al., *J. Phys. Chem. A*, 106(33), 7593–7598 (2002)) as shown in Reaction Scheme VI.

Reaction Scheme VI

Compounds of the invention utilize aryl-ethynyl coupling reactions. Such couplings can be achieved using Heck-Reaction (H-R) methodology where aryl bromides and iodides are reacted with aliphatic, aromatic or heteroaromatic terminal alkynes in the presence of a palladium catalyst. One suitable catalytic system is $(PPh_3)_4Pd(0)/CuI/Et_3N$, as described in Sanechika et al., *Bull. Chem. Soc. Jpn.*, 57, 752–755 (1984). Other catalyst systems include Pd(II) and CuI such as, for example, $Pd(OAc)_2/PPh_3/CuI/Et_2NH$ and $Pd(PPh_3)_2Cl_2/PPh_3/CuI/Et_3N/pyridine$.

In one embodiment, acetylene is coupled with compounds of Formula CCCXVIII in a stepwise manner. This can be achieved, for example, by using trimethylsilyl acetylene where the trimethylsilyl (TMS) moiety acts as a protecting group for one terminus of acetylene. De-protection can be achieved by stirring the TMS-terminated intermediate CCCXIX with $K_2CO_3/MeOH$ at room temperature. (Takahashi et al., *Synthesis*, 627 (1980)). In Reaction Scheme VII, J is as described for Formula I. A similar reaction can be used to prepared $D—C \equiv CH$ (CCCXXII).

Reaction Scheme VII

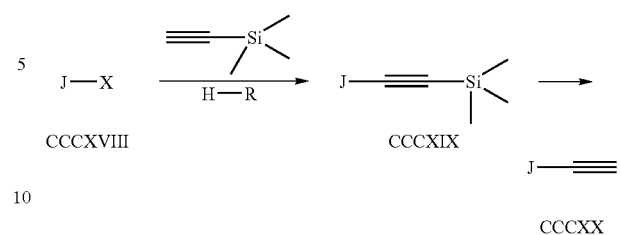

The compounds CCCXXIII in Reaction Scheme VIII is a subgenus of Formula I where n is equal to 1. The compound CCCXXIII can be made by the stepwise reaction of the thus obtained ethynyls $J—C \equiv CH$ (CCCXX), $D—C \equiv CH$ (CCCXXII) with CCC where G, E, Ar1, D, and J are as described for Formula I.

Reaction Scheme VIII

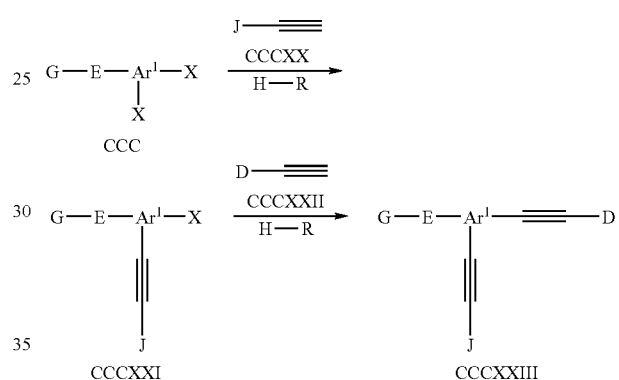

In cases of CCCXXIII where D is equal to J, the reaction of CCC with a two molar equivalents of the ethynyl $J—C \equiv CH$ gives the compound CCCXXIII in a one step reaction.

Alternatively CCCXXIII can be prepared from the ethynyls $J—C \equiv CH$, $D—C \equiv CH$ by conversion to the corresponding magnesium bromide derivatives $J—C \equiv C—MgBr$ or $D—C \equiv C—MgBr$ with an equivalent of ethyl magnesium bromide under standard conditions. Without isolation, the magnesium bromide salt can be reacted with CCC to produce CCCXXIII when n is equal to 1.

Alternatively, where n is equal to 1, CCC can be converted to the corresponding bis-TMS-derivative $G—E—Ar^1—(C \equiv CH)_2$ by treatment with two equivalents of $TMS—C \equiv CH$ and then desilylated with $MeOH/K_2CO_3$ as shown in Reaction Scheme IX. The derivative CCCXXV can then be reacted in a stepwise manner with bromides $D—X$, $J—X$ under H-R conditions to give the CCCXXIII.

Reaction Scheme IX

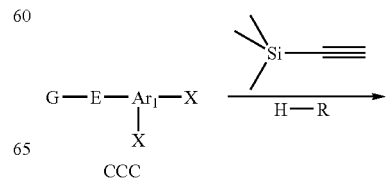

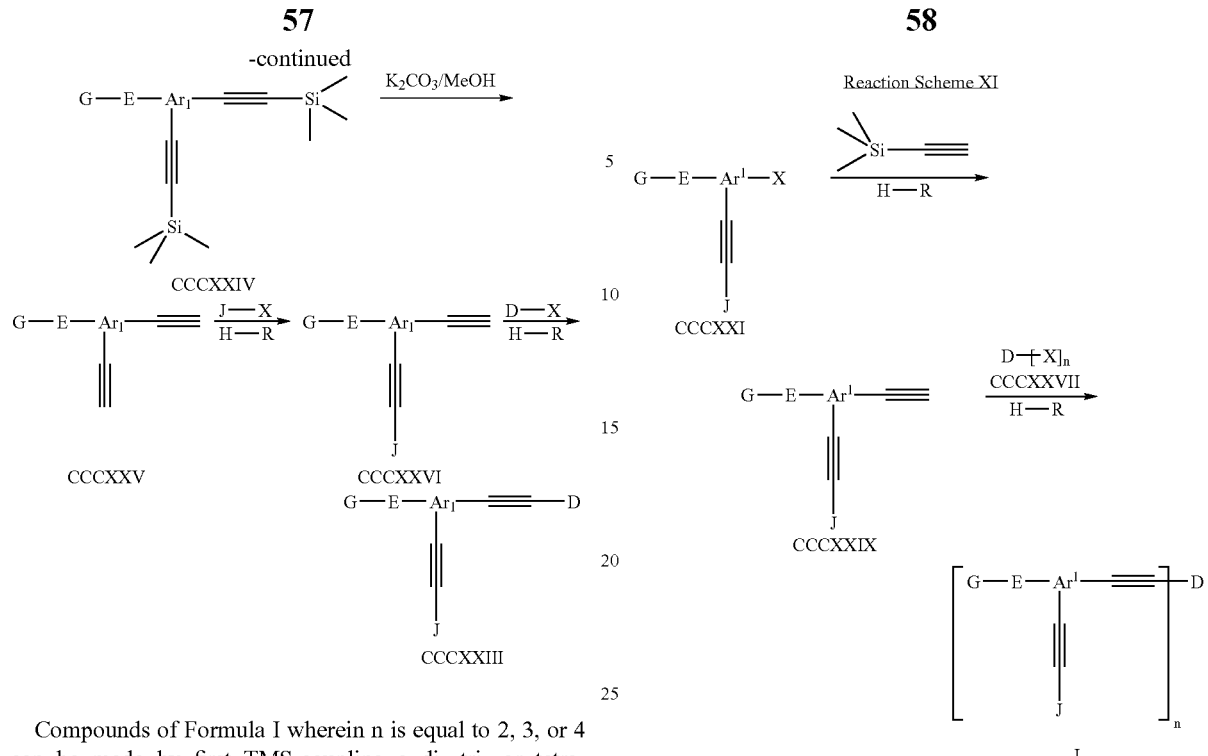

Compounds of Formula I wherein n is equal to 2, 3, or 4 can be made by first TMS-coupling a di- tri- or tetra-substituted core structures $DX_n$ (CCCXXVII) to their corresponding ethynyls to form $D—(C≡CH)_n$ (CCCXXVIII) as shown in Reaction Scheme X. Representative examples of ethynyls CCCXXVIII include, without limitation: 1,3,5-tris-(4-ethynylphenyl)benzene (see E. Weber et al., *J. Chem. Soc. Perkin Trans.*, 2, 1251–1258 (1988)), tetrakis(4-ethynylphenyl)methane (see Weil et al., *J. Amer. Chem. Soc.*, 123 (33), 8101–108 (2001)) and 2,2',7,7'-tetraethynyl-9,9'-spirobifluorene, tris-(4-ethynylphenyl)-amine (see EP 1,170, 273 A1). Compound CCCXXVIII is then coupled with CCCXXI to give a compound of Formula I.

Alternatively the intermediate CCCXXI can be coupled with TMS—C≡CH under H-R conditions followed by de-silylation to give the diyne CCCXXIX. The diyne CCCXXIX is then reacted with the halides of group D to give molecules of Formula I as shown in Reaction Scheme XI.

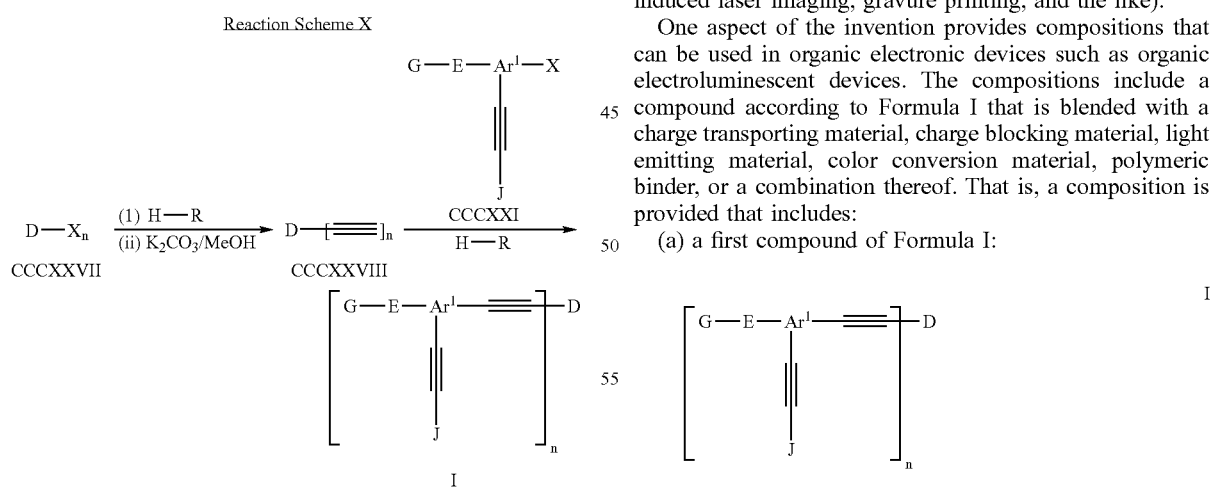

Compositions

There is a need in the art for solution processible electroluminescent compositions that can be uniformly coated or printed onto a substrate for the purpose of fabricating organic electroluminescent devices. OLED devices prepared from these compositions can typically provide at least one of the following: low operating voltages, high external quantum efficiencies, proper color coordinates (e.g. red, green, and blue for display applications or white for backlight applications), long operating lifetimes, and compatibility with the printing process (e.g. inkjet printing, thermal induced laser imaging, gravure printing, and the like).

One aspect of the invention provides compositions that can be used in organic electronic devices such as organic electroluminescent devices. The compositions include a compound according to Formula I that is blended with a charge transporting material, charge blocking material, light emitting material, color conversion material, polymeric binder, or a combination thereof. That is, a composition is provided that includes:

(a) a first compound of Formula I:

wherein

D is a core that is a monovalent, divalent, trivalent, or tetravalent radical of a $C_{3-30}$ alkane, $C_{3-30}$ heteroalkane, conjugated or unconjugated $C_{6-60}$ carbocyclic aromatic compound, $C_{3-60}$ heteroaromatic compound, $C_{18-60}$ tertiary aromatic amino compound, or a compound of Formula II or Formula III

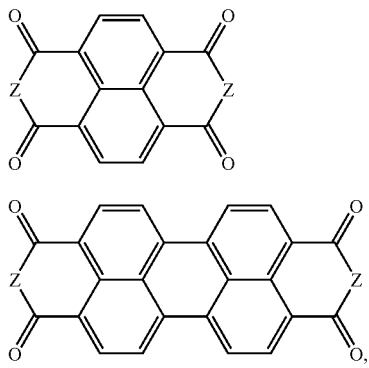

that is unsubstituted or substituted with one or more alkyl, alkenyl, alkoxy, aryl, aryloxy, fluoro, fluoroalkyl, perfluoroalkyl, heteroalkyl, heteroaryl, or combinations thereof, wherein $Ar^1$ is trivalent radical of a conjugated $C_{6-30}$ carbocyclic aromatic compound that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

E is an $C_{3-60}$ heteroarylene having at least one —C=N— unit, said heteroarylene being unsubstituted or substituted with one or more alkyl alkenyl, alkoxy, aryl, aryloxy, fluoro, fluoroalkyl, perfluoroalkyl, heteroalkyl, heteroaryl, or combinations thereof;

G is a monovalent radical selected from hydrogen, $C_{1-30}$ alkyl, $C_{1-30}$ heteroalkyl, $C_{3-60}$ heteroaryl, $C_{6-60}$ aryl, or $C_{18-60}$ tertiary aromatic amino aryl that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

J is a monovalent radical selected from $C_{1-30}$ alkyl, $C_{1-30}$ heteroalkyl, $C_{3-60}$ heteroaryl, $C_{6-60}$ aryl, or $C_{18-60}$ tertiary aromatic amino aryl that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

Z is selected from $NH$ or $CH_2$; and n is an integer of 1 to 4; and (b) a second compound selected from a charge transporting material, a charge blocking material, a light emitting material, a color conversion material, a polymeric binder, or a combination thereof.

The charge transporting material can be either a small molecule or a polymeric material and can transport holes, electrons, or a combination thereof. The charge blocking material can be either a small molecule or a polymeric material and can block holes, electrons, or a combination thereof. The light emitting material and the color conversion material can be either a small molecule or polymeric material. Such blends can be prepared, for example, by blending the compounds in a solution or in a melt state. In some embodiments, the compositions can be in the form of film prepared from the blended compounds.

Such compositions can be useful for making organic electronic devices by thermal patterning of the materials onto a receptor. The compositions can also be useful for non-thermal printing, patterning, and transfer methods including, for example, inkjet printing, screen printing, and photolithographic patterning.

Hole transport agents useful in these compositions are preferably selected from tertiary aromatic amine derivatives, electron rich heteroarylene derivatives, electron rich inorganic and organometallic complexes, or polymers derived from these materials. Hole transport polymers useful in these blends include polyvinyl carbazoles, triaryl amine based polymer of the types taught in DE Patent No. 3,610,649, U.S. Pat. No. 5,681,664, patent application WO 99/32537, and patent application WO 98/06773, all of which are incorporated by reference. Other examples of hole transport agents include copper phthalocyanine (CuPC) and compounds such as those described in H. Fujikawa, et al., *Synthetic Metals*, 91, 161 (1997) and J. V. Grazuleviciua et al., "Charge-Transporting Polymers and Molecular Glasses", *Handbook of Advanced Electronic and Photonic Materials and Devices*, H. S. Nalwa (ed.), 10, 233–274 (2001), both of which are incorporated herein by reference.

Electron transport agents useful in these blended systems can be selected from polycyclic aromatic hydrocarbons, heteroaromatic compounds having at least one —C=N— unit, and electron deficient inorganic complexes. Suitable electron transport agents include oxadiazole derivatives such as 2-(4-biphenyl)-5-(4-t-butylphenyl)-1,3,4-oxadiazole (also known as PBD), 1,3-bis[5-(4-(1,1-dimethylethyl)phenyl)-1,3,4-oxadiazol-2-yl]benzene (known as PBD dimer) as well as starburst and dendrimeric derivatives of oxadiazoles (Bettenhausen et al., *Synthetic Metals*, 91, 223 (1997)), incorporated herein by reference; N-substituted triazole derivatives such as 3-(4-biphenylyl)-4-phenyl-5-(4-tert-butylphenyl)1,2,4-triazole (also known as TAZ) as well as starburst and dendrimeric derivatives of triazoles; organometallic compounds such as tris(8-hydroxyquinolato) aluminum ($Alq_3$) and biphenylatobis(8-hydroxyquinolato) aluminum (Balq); and other compounds described in C. H. Chen et al., *Macromol. Symp.* 125, 1 (1997) and J. V. Grazulevicius et al., "Charge-Transporting Polymers and Molecular Glasses", *Handbook of Advanced Electronic and Photonic Materials and Devices*, H. S. Nalwa (ed.), 10, 233 (2001), both of which are incorporated herein by reference.

Small molecule emitters useful in these blended systems are without restriction, but are typically selected from molecular emitters derived from fluorescent polynuclear arylene and heteroarylene derivatives, phosphorescent cyclometallated chelate complexes of Ir(III), Rh(III), Os(II), Ru(II), Ni(II) and Pt(II), and fluorescent chelate complexes of Zn(II) and Al(III). Examples of useful fluorescent polynuclear arylene emitters include molecules derived from perylene, benzo[g,h,i]perylene, anthracene, pyrene, decacyclene and fluorenes. Examples of useful fluorescent polynuclear heteroarylene derivatives include molecules derived from coumarins such as 10-(2-benzothiazolyl)-2,3,6,7-tetrahydro-1,1,7,7-tetramethyl-1H,5H,11H-[1]benzopyrano[6,7,8-ij]quinolizin-11-one (also known as Coumarin C545T), 3-(2-benzothiazolyl)-7-diethylaminocoumarin (also known as Coumarin 6 or Coumarin 540), and 3-thiophenyl-7-methoxycoumarin.

Examples of useful phosphorescent cyclometallated chelate complexes of Ir(III), Rh(III), Os(II), Ru(II), and Pt(II) include molecules derived from phosphorescent organometallic $L^1{}_3Ir$ (III), $L^1{}_3Rh$ (III), $L^1L^2Ir(III)X$, $L^1L^2Rh(III)X$, $L^1L^2Os(II)Y$, $L^1L^2Ru(II)Y$, and $L^1L^2Pt(II)$ compounds where $L^1$ and $L^2$ can be the same or different in each instance and are optionally substituted cyclometallated bidentate ligands of 2-(1-naphthyl)benzoxazole, 2-phenylbenzoxazole, 2-phenylbenzothiazole, 2-phenylbenzimidazole, 7,8-benzoquinoline, coumarin, (thienylpyridine), phenylpyridine, benzothienylpyridine, 3-methyoxy2-phenylpyridine, thienylpyridine, tolylpyridine; X is selected from the group consisting of acetylacetonate ("acac"), hexafluoroacetylacetonate, salicylidene, picolinate, and 8-hydroxyquinolinate; Y is selected from charge neutral chelating compounds such as an optionally substituted derivatives of phenathroline or bipyridine. Cyclometallated Ir(III) chelate derivatives such as those taught in patent applications WO 00/70655 and WO 01/41512 A1 and cylcometalated Os(II) chelate derivatives such as those taught in U.S. Pat. No. 6,664,111 are herewith incorporated by reference. Platinum(II) porphyrins such as octaethyl porphyrin (also known as Pt(OEP)) are also useful.

Examples of useful fluorescent chelate complexes of Zn(II) and Al(III) include complexes such as bis(8-quinolinolato)zinc(II), bis(2-(2-hydroxyphenyl) benzoxazolate)zinc(II), bis(2-(2-hydroxyphenyl) benzothiazolate)zinc(II), bis(2-(2-hydroxyphenyl)-5-phenyl-1,3,4-oxadiazole)zinc(II), bis(8-quinolinolato) aluminum(III), and biphenylatobis(8-hydroxyquinolato) aluminum (BALq). Fluorescent Zn (II) chelates such as those taught by Tokito et al., *Synthetic Metals*, 111–112, 393–396, (2000) and in patent application WO 01/39234 A2, all of which are incorporated by reference. Useful Al(III) chelates include those taught in U.S. Pat. No. 6,203,933 B1, incorporated herein by reference.

Suitable light emitting polymers for use in these blends are polymers and copolymers of the polyfluorenes (PFs), polyparaphenylenes (PPPs), polyphenylenevinylenes (PPVs), and polyspirobisfluorenes.

In one embodiment, a compound according to Formula I is blended with one or more materials to provide a composition that can transport both holes and electrons. For example, a compound of Formula I that can transport electrons can be combined with either a small molecule or a polymeric hole transporting material. Such a composition can be charge balanced by virtue of the blend ratio and the compounds selected. Optionally, a light emitting polymer or electroluminescent small molecule can be added to the blend to form compositions that can be formed into an organic emissive element.

These types of compositions can be solution processible and can be spin coated to provide thin films that are electroluminescent. The compositions can be, for example, in the form of an amorphous film that can be thermally transferred from a donor substrate to a receptor substrate. The compositions can be thermally imaged to form pixilated arrays useful in OLED display manufacture and can be optimized to give rise to high quantum efficiency electroluminescence by varying the thickness of the film and the ratio of components within the ranges specified. The emission color can be varied by choice of the light emitting material. For example, perylene, bis(2-(2-hydroxyphenyl) benzoxazolate)zinc(II), or 3-thienyl-7-methoxy-coumarin give rise to blue emission; benzothienyl pyridine acetylacetonate iridium(III), or platinum octaethylporphyrin give rise to red emission; Coumarin 6, Coumarin C545T and Ir(ppy)$_3$ give rise to green emission; and t-butylated decacyclene gives rise to white emission.

The compositions can include a first compound according to Formula I and a second compound that has structural similarities to the first compound. A compound of Formula I has a core and one or more end capping groups that are attached to the core. The second compound can include a radical that includes the core of the first compound, a monovalent radical that includes the end capping group of the first compound, a divalent radical that includes a divalent radical of the end capping group of the first compound, or a combination thereof. The second compound can be, for example, a light emitting material, a color conversion material, a charge transporting material, a charge blocking material, a polymeric binder, or a combination thereof.

In this aspect, the second compound can be unsubstituted, can have a substituent of a same type that is present on the corresponding structure of the first compound, or can be substituted with a substituent that is absent on the corresponding structure of the first compound. In some embodiments, the substituent on a radical of the second compound can be identical to that on a corresponding structure of the first compound. The corresponding structure of the first compound can be the first core, the first end capping group, or a divalent radical of the first end capping group. Both the radical of the second compound and the corresponding structure of the first compound can be free of substituents. In a specific example, the first end capping group can be a radical of anthracene without any substituent group and the second compound includes a radical of anthracene without any substituent group. Similarly, both the radical of the second compound and the corresponding structure of the first compound can have identical substituents. In a specific example, the first end capping group can be a radical of anthracene with a methoxy substituent and the second compound includes a radical of anthracene with a methoxy substituent in the same position as in the first end capping group.

Additionally, the second compound can contain a radical that is similar to, but not identical to, a corresponding structure of the first compound. For example, a substituent on a radical of the second compound can be absent on a corresponding structure of the first compound. In a specific example, the first end capping group is a radical of anthracene without any substituent groups and the second compound includes a radical of anthracene with a methoxy substituent. Likewise, a substituent on a radical included in the first compound can be absent on a corresponding structure of the second compound. In another specific example, the first compound has an end capping group that is a spirobisfluorenyl group with a methyl substituent and the second compound has an end capping group that is an unsubstituted spirobisfluorenyl group.

A substituent on a radical of the second compound can be of the same type of substituent (e.g., alkyl, alkenyl, alkoxy, aryl, aryloxy, fluoro, fluoroalkyl, perfluoroalkyl, heteroalkyl, heteroaryl, or combinations thereof) present on the corresponding structure of the first compound but contain a different number of carbon atoms. In a specific example, the first end capping group is a radical of anthracene with a methoxy substituent and the second compound includes a radical of anthracene with an ethoxy substituent. In another specific example, the first compound has an end capping group that is a spirobisfluorenyl group substituted with a methyl group and the second compound contains an end capping group that is a spirobisfluorenyl group substituted with a tert-butyl group.

The substituents on the first compound and the second compound cannot be of a different type if they are substituted in the same position. In a specific example, if the first end capping group is a spirobisfluorenyl group substituted with a methyl group and the second compound has a spirobisfluorenyl group substituted with a phenyl group in the same position where the methyl group is located on the first end capping groups, then the groups are not considered to be structurally similar.

The second compound of the composition can be a small molecule (i.e., non-polymeric) or can be a polymeric material. In some embodiments, the composition includes both a hole transporting material and an electron transporting material. In other embodiments, the composition includes a hole transporting material, an electron transporting material, and a light emitting material.

In one embodiment of a composition of the invention, the first compound is a compound according to Formula I and has a first end capping group (e.g., the first compound can be represented, for example by the formula $Z_1$—A—$Z_1$ where A is the core and $Z_1$ are two identical end capping groups). The second compound can be polymeric or a small molecule (i.e., non-polymeric) and has a second end capping group that includes the first end capping group (e.g., the second compound has an end capping group $Z_2$; and $Z_2$ includes $Z_1$).

In a variation of this first embodiment, the first end capping group or the second end capping group has a substituent that is absent in the other moiety. In another variation, the first end capping group and the second end capping group have the same type of substituents (e.g., alkyl, alkenyl, alkoxy, aryl, aryloxy, fluoro, fluoroalkyl, perfluoroalkyl, heteroalkyl, heteroaryl, or combinations thereof) but the number of carbon atoms in the substituents are different.

In a second embodiment, the first compound is a compound according to Formula I and has a first core (e.g., the first compound can be represented, for example by the formula Z—$A_1$—Z where $A_1$ is the first core and Z are two identical end capping groups). The second compound can be polymeric or a small molecule and contains a divalent, trivalent, or tetravalent radical that includes the first core (e.g., the second compound contains a radical $A_2$ and $A_2$ includes $A_1$).

In a variation of the second embodiment, the first core or the corresponding radical in the second compound has a substituent that is absent in the other moiety. In another variation, the first core and the corresponding radical in the second compound have the same type of substituents (e.g., alkyl, alkenyl, alkoxy, aryl, aryloxy, fluoro, fluoroalkyl, perfluoroalkyl, heteroalkyl, heteroaryl, or combinations thereof) but the number of carbon atoms in the substituents are different.

In a third embodiment, the first compound is a compound according to Formula I and has a first end capping group (e.g., the first compound can be represented, for example, by the formula $Z_1$—A—$Z_1$ where A is the core and $Z_1$ are two identical first end capping groups). The second compound is a small molecule and has a second end capping group that includes the first end capping group (e.g., the second compound can be represented, for example, by the formula $Z_2$—B—$Z_2$ where B is the core and $Z_2$ are two identical second end capping groups; and $Z_2$ includes $Z_1$). Such a composition could be used, for example, to prepare a film that includes two small molecules with an active (i.e., electroactive or electroluminescent) core. The similar end capping groups can be used to enhance the compatibility of the two small molecules.

In a variation of the third embodiment, the first end capping group or the second end capping group can contain a substituent that is lacking in the other end capping group. In another variation, both the first and the second end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a fourth embodiment, the composition includes a first compound according to Formula I, a second compound that is a small molecule, and a third compound that is a light emitting polymer. The first compound has a first end capping group (e.g., the first compound can be represented, for example, by the formula $Z_1$—A—$Z_1$ where A is the core and $Z_1$ are two identical first end capping groups) and the second compound has a second end capping group that includes the first end capping group (e.g., the second compound can be represented, for example, by the formula $Z_2$—B—$Z_2$ where B is the core and $Z_2$ are two identical second end capping groups; and $Z_2$ includes $Z_1$). Such a composition could be used, for example, to prepare a film that includes a small molecule blend with a light emitting polymer where the end capping groups of the first and second compound can enhance the compatibility of the entire composition. The small molecules can include active cores.

In a variation of the fourth embodiment, the first end capping group or the second end capping group can contain a substituent that is lacking in the other end capping group. In another variation, both the first and the second end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a fifth embodiment, the composition includes a first compound according to Formula I, a second compound that is a small molecule, and third compound that is an electroactive polymer. The first compound has a first end capping group (e.g., the first compound can be represented, for example, by the formula $Z_1$—A—$Z_1$ where A is the core and $Z_1$ are two identical first end capping groups) and the second compound has a second end capping group that includes the first end capping group (e.g., the second compound can be represented, for example, by the formula $Z_2$—B—$Z_2$ where B is the core and $Z_2$ are two identical second end capping groups; and $Z_2$ includes $Z_1$). Such a composition could be used, for example, to prepare a film that includes a small molecule blend with an electroactive polymer where the end capping groups of the first and second compound can enhance the compatibility of the entire composition. The small molecules can include active cores.

In a variation of the fifth embodiment, the first end capping group or the second end capping group can contain a substituent that is lacking in the other end capping group. In another variation, both the first and the second end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a sixth embodiment, the composition include a first compound according to Formula I, a second compound that is a small molecule, and a third compound that is an inactive polymer. As used herein, the term "inactive polymer" refers to a polymer that is not electroactive and that is not a light emitting polymer. The inactive polymer can serve, for example, as a matrix for the first compound and the second compound. The first compound has a first end capping group (e.g., the first compound can be represented, for example, by the formula $Z_1$—A—$Z_1$ where A is the core and $Z_1$ are two identical first end capping groups) and the second compound has a second end capping group that includes the first end capping group (e.g., the second compound can be represented, for example, by the formula $Z_2$—B—$Z_2$ where B is the core and $Z_2$ are two identical second end capping groups; and $Z_2$ includes $Z_1$). Such a composition could be used, for example, to prepare a film that includes a small molecule blend in an inactive polymer matrix where the end capping groups of the first and second compound can enhance the compatibility of the entire composition. The small molecules can include active cores.

In a variation of this sixth embodiment, the first end capping group or the second end capping group can contain a substituent that is lacking in the other end capping group. In another variation, both the first and the second end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a seventh embodiment, the composition includes a first compound according to Formula I and a second compound that is a small molecule. The first compound has a first core (e.g., the first compound can be represented, for example, by the formula Z—$A_1$—Z where $A_1$ is the first core and Z are two identical end capping groups) and the second compound contains a corresponding radical that includes the first core (e.g., the second compound can be represented, for example, by the formula Y—$A_2$—Y where $A_2$ is the second core and Y are two identical end capping groups; and $A_2$ includes $A_1$). Such a composition could be used, for example, to prepare a film that includes two small molecules with active (i.e., electroactive or electroluminescent) end capping groups. The similar cores can be used, for example, to enhance the compatibility of the two small molecules.

In a variation of the seventh embodiment, either the first core or the corresponding radical in the second compound contain a substituent that is lacking in the other moiety. In another variation, both the first core and the corresponding radical in the second compound have substituents that are of the same type (e.g., alkyl, alkenyl, alkoxy, aryl, aryloxy, fluoro, fluoroalkyl, perfluoroalkyl, heteroalkyl, heteroaryl, and combinations thereof) but the substituents can contain a different number of carbon atoms.

In an eighth embodiment, the composition includes a first compound according to Formula I, a second compound that is a small molecule, and a third compound that is a light emitting polymer. The first compound has a first core (e.g., the first compound can be represented, for example, by the formula Z—$A_1$—Z where $A_1$ is the first core and Z are two identical end capping groups) and the second compound contains a corresponding radical that includes the first core (e.g., the second compound can be represented, for example, by the formula Y—$A_2$—Y where $A_2$ is the second core and Y are two identical end capping groups; and $A_2$ includes $A_1$). Such a composition could be used, for example, to prepare a film that includes a small molecule blend with a light emitting polymer where the cores of the first and second compound can enhance the compatibility of the entire composition. The small molecules can include, for example, active end capping groups.

In a variation of the eighth embodiment, either the first core or the corresponding radical in the second compound can contain a substituent that is lacking in the other moiety. In another variation, both the first core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a ninth embodiment, the composition includes a first compound according to Formula I, a second compound that is a small molecule, and a third compound that is an electroactive polymer. The first compound has a first core (e.g., the first compound can be represented, for example, by the formula Z—$A_1$—Z where $A_1$ is the first core and Z are two identical end capping groups) and the second compound contains a corresponding radical that includes the first core (e.g., the second compound can be represented, for example, by the formula Y—$A_2$—Y where $A_2$ is the second core and Y are two identical end capping groups; and $A_2$ includes $A_1$). Such a composition could be used, for example, to prepare a film that includes a small molecule blend with an electroactive polymer where the cores of the first and second compound can enhance the compatibility of the entire composition. The small molecules can include, for example, active end capping groups.

In a variation of the ninth embodiment, either the first core or the corresponding radical in the second compound can contain a substituent that is lacking in the other moiety. In another variation, both the first core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a tenth embodiment, the composition includes a first compound according to Formula I, a second compound that is a small molecule, and a third compound that is an inactive polymer. The first compound has a first core (e.g., the first compound can be represented, for example, by the formula Z—$A_1$—Z where $A_1$ is the first core and Z are two identical end capping groups) and the second compound contains a corresponding radical that includes the first core (e.g., the second compound can be represented, for example, by the formula Y—$A_2$—Y where $A_2$ is the second core and Y are two identical end capping groups; and $A_2$ includes $A_1$). Such a composition could be used, for example, to prepare a film that includes a small molecule blend with an inactive polymer where the cores of the first and second compound can enhance the compatibility of the entire composition. The small molecules can include, for example, active end capping groups.

In a variation of the tenth embodiment, either the first core or the corresponding radical in the second compound can contain a substituent that is lacking in the other moiety. In another variation, both the first core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In an eleventh embodiment, the composition includes a first compound according to Formula I and a second compound that is a polymer. The first compound has a first core (e.g., the first compound can be represented by the formula Z—$A_1$—Z where $A_1$ is the first core and Z are two identical end capping groups). The polymer is a reaction product of a monomer mixture that includes a first monomer that contains a radical that includes the first core (e.g., the first monomer contains a radical $A_2$; and $A_2$ includes $A_1$). Such a composition can be used, for example, to prepare a film that includes a small molecule having groups in common with a polymer. The common groups can enhance the compatibility of the compounds in the composition.

In a variation of the eleventh embodiment, either the first core or the corresponding radical in the second compound can contain a substituent that is lacking in the other moiety. In another variation, both the first core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a twelfth embodiment, the composition includes a first compound according to Formula I and a second compound that is a polymer. The first compound contains a first end capping group (e.g., the first compound can be represented, for example, by a formula $Z_1$—A—$Z_1$ where A is the core and $Z_1$ are two identical first end capping groups). The polymer is a reaction product of a monomer mixture that includes a first monomer that contains a divalent radical that includes a divalent radical of the first end capping group (e.g., the first monomer contains $Z_2$; and $Z_2$ includes a radical of $Z_1$). Such a composition can be used, for example, to prepare a film that includes a small molecule having groups in common with a polymer. The similar groups in both the first and second compound can enhance the compatibility of the compounds in the composition.

In a variation of the twelfth embodiment, the first end capping group or the second end capping group can contain a substituent that is lacking in the other end capping group. In another variation, both end capping groups can have substituents that are of the same type (e.g., alkyl, alkenyl, alkoxy, aryl, aryloxy, fluoro, fluoroalkyl, perfluoroalkyl, heteroalkyl, heteroaryl, and combinations thereof) but the substituents can contain a different number of carbon atoms.

In a thirteenth embodiment, the composition includes a first compound according to Formula I, a second compound that is a small molecule, and a polymer. The first compound has a first end capping group and a first core (e.g., the first compound can be represented, for example, by the formula $Z_1$—A—$Z_1$ where A is the first core and $Z_1$ are two identical first end capping groups). The second compound has a second end capping group that includes the first end capping group $Z_1$ but a second core that is different than the first core (e.g., the second compound can be represented, for example, by the formula $Z_2$—B—$Z_2$ where B is the second core and $Z_2$ are two identical second end capping groups; $Z_1$ includes $Z_2$; and B does not include A). The polymer is the reaction product of a monomer mixture that includes a first monomer that contains a radical that includes the first core and a second monomer that contains a radical that includes the second core (e.g., the first monomer contains a radical $A_3$ and the second monomer contains a radical $B_3$; $A_3$ includes A; and $B_3$ includes B). Such a composition can be used, for example, to prepare a film that includes small molecules that have groups in common with a polymer formed by reacting the monomer mixture. The similar groups in both the small molecules and the similar groups between the small molecules and the polymer can enhance the compatibility of the compounds in the composition.

In a first variation of the thirteenth embodiment, the first end capping group or the second end capping group can contain a substituent that is lacking in the other end capping group. In a second variation, both end capping groups can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms. In a third variation, either the first core or the corresponding radical in the polymer can contain a substituent that is lacking in the other moiety. In a fourth variation, both the first core and the corresponding radical in the polymer can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms. In a fifth variation, either the second core or the corresponding radical in the polymer can contain a substituent that is lacking in the other moiety. In another variation, both the second core and the corresponding radical in the polymer have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

In a fourteenth embodiment, the composition includes a first compound according to Formula I, a second compound that is a small molecule, and a polymer. The first compound has a first core and a first end capping group (e.g., the first compound can be represented, for example, by the formula Z—$A_1$—Z where $A_1$ is the first core and Z are two identical first end capping groups). The second compound has a second core that includes the first core but a second end capping group that is different than the first end capping group (e.g., the second compound can be represented, for example, by the formula Y—$A_2$—Y where $A_2$ is the second core and Y are two identical second end capping groups; and $A_2$ includes $A_1$). The polymer is the reaction product of a monomer mixture that includes a first monomer that contains a divalent radical of the first end capping group and a second monomer that contains a divalent radical of the second end capping group (e.g., the first monomer can contain the radical $Z_3$ and the second monomer can contain the radical $Y_3$; $Z_3$ includes a radical of Z; and $Y_3$ includes a radical of Y). Such a composition can be used, for example, to prepare a film that includes small molecules that have groups in common with a polymer formed by reacting the monomer mixture. The similar groups between the two small molecules and the similar groups between the small molecules and the polymer can enhance the compatibility of the composition.

In a first variation of the fourteenth embodiment, the first core or the radical in the second compound can contain a substituent that is lacking in the other moiety. In a second variation, both the first core and the corresponding radical in the second compound can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms. In a third variation, either the first end capping group or the corresponding monovalent radical in the first monomer of the monomer mixture can contain a substituents that are lacking in the other moiety. In a fourth variation, both the first end capping group and the corresponding monovalent radical in the first monomer can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms. In a fifth variation, either the second end capping group or the corresponding monovalent radical in the second monomer of the monomer mixture can contain a substituent that is lacking in the other moiety. In another variation, both the second end capping group and the corresponding monovalent radical in the second monomer can have substituents that are of the same type (e.g., alkyl, alkenyl, alkoxy, aryl, aryloxy, fluoro, fluoroalkyl, perfluoroalkyl, heteroalkyl, heteroaryl, or combinations thereof) but the substituents can contain a different number of carbon atoms.

The above embodiments provide examples where the first compound has two end capping groups. Similar examples include those in which the first compound has one, three, or four end capping groups.

The above embodiments provide examples where the first compound has identical end capping groups. Similar examples include those in which the first compound has non-identical end capping groups and the second compound has structural similarities to at least one of the end capping groups.

The above embodiments provide examples where the second compound has two end capping groups. Similar examples include those in which the second compound has only one end capping group or more than two end capping groups.

The above embodiments provide examples where the second compound has identical end capping groups. The end capping groups of the second compound can be the same or different from each other. Similar examples include those in which at least one of the end capping groups has structural similarities to the first compound.

Organic Electronic Devices

In another aspect, the present invention provides organic electronic devices that include a compound of Formula I or compositions that include a compound of Formula I. Organic electronic devices are articles that include layers of organic materials, at least one of which can conduct an electric current. Examples of organic electronic devices that can be made using the compounds or compositions of this invention include organic transistors and diodes, photovoltaic devices, organic electroluminescent (OEL) devices such as organic light emitting diodes (OLEDs), and the like.

The organic electronic device can be an organic electroluminescent display or device. As used herein, "organic electroluminescent (OEL) displays or devices" refer to displays or devices that include an organic light emitting material sandwiched between an anode and a cathode. The light emitting material can be a small molecule (SM) emitter, a SM doped polymer, a light emitting polymer (LEP), a doped LEP, a blended LEP, or another organic emissive material that can be provided alone or in combination with any other organic or inorganic materials that are functional or non-functional in the OEL display or devices. The organic electroluminescent displays or devices have potential use in applications such as backlighting of graphics, pixelated displays, and large emissive graphics.

R. H. Friend et al. in "Electroluminescence in Conjugated Polymers," *Nature,* 397, 121 (1999), incorporated herein by reference, describe one mechanism of electroluminescence as including the "injection of electrons from one electrode and holes from the other, the capture of oppositely charged carriers (so-called recombination), and the radiative decay of the excited electron-hole state (exciton) produced by this recombination process."

The organic electroluminescent device includes an organic emissive element. The organic emissive element includes a thin layer, or layers, of one or more suitable organic materials sandwiched between a cathode and an anode. The organic emissive element typically provides electron transport and hole transport as well as light emission. When activated, electrons are injected into the organic emissive element from the cathode and holes are injected into the organic emissive element from the anode. Electrons reside in the organic emissive element as radical anions and holes as radical cations. As the injected charges migrate towards the oppositely charged electrodes, they may recombine to form electron-hole pairs that are typically referred to as excitons. The region of the device in which the excitons are generally formed can be referred to as the recombination zone. These excitons, or excited state species, can emit energy in the form of light as they decay back to a ground state.

The organic emissive element typically includes a light emitting layer. The light emitting layer includes a light emitting material such as a light emitting polymer or a light emitting small molecule. The light emitting layer optionally includes other materials, such as, for example, hole transport material, electron transport material, binder, polymeric binder, wave guiding particles, phosphorescent compounds, and color conversion materials. In some embodiments, the light emitting layer includes a compound according to Formula I. For example, the light emitting layer can include a compound according to Formula I as well as a second compound that is a light emitting material, a charge transporting material, a charge blocking material, a color conversion material, a polymeric binder, or a combination thereof.

Other layers can also be present in organic emissive element such as hole transport layers, electron transport layers, hole injection layer, electron injection layers, hole blocking layers, electron blocking layers, buffer layers, and the like. In addition, photoluminescent materials can be present in the light emitting layer or other layers in OEL devices, for example, to convert the color of light emitted by the electroluminescent material to another color. These and other such layers and materials can be used to alter or tune the electronic properties and behavior of the layered OEL device, for example to achieve a desired current/voltage response, a desired device efficiency, a desired color, a desired brightness, and the like. In some embodiments, a compound according to Formula I can be included in these other layers of the light emissive element. In other embodiments, at least one of these other layers includes a compound according to Formula I as well as a second compound that is a light emitting material, a charge transporting material, a charge blocking material, a color conversion material, a polymeric binder, or a combination thereof. For example, the compounds or compositions of the invention can be included in the electron transport layer, the hole transport layer, or a combination thereof.

In some embodiments, the light emitting molecule included in the organic emissive element of an organic electroluminescent device can be a molecularly doped polymer where charge carrying and/or emitting species are dispersed in a polymer matrix (see J. Kido, "Organic Electroluminescent devices Based on Polymeric Materials," *Trends in Polymer Science,* 2, 350–355 (1994)); a conjugated polymer or light emitting polymer (LEP) where layers of polymers such as poly(phenylenevinylene) act as the charge carrying and emitting species (see J. J. M. Halls, D. R. Baigent, F. Cacialli, N. C. Greenham, R. H. Friend, S. C. Moratti, and A. B. Holmes, "Light-emitting and Photoconductive Diodes Fabricated with Conjugated Polymers," *Thin Solid Films,* 276, 13–20 (1996)); a vapor deposited small molecule heterostructure (see U.S. Pat. No. 5,061,569, incorporated by reference, and C. H. Chen, J. Shi, and C. W. Tang, "Recent Developments in Molecular Organic Electroluminescent Materials," *Macromolecular Symposia,* 125, 1–48 (1997)); or various combinations of these elements.

Other examples of OLEDs include light emitting electrochemical cells (see Q. Pei, Y. Yang, G. Yu, C. Zang, and A. J. Heeger, "Polymer Light-Emitting Electrochemical Cells: In Situ Formation of Light-Emitting p-n Junction," *Journal of the American Chemical Society,* 118, 3922–3929 (1996)) and vertically stacked organic light-emitting diodes capable of emitting light of multiple wavelengths (see U.S. Pat. No. 5,707,745, incorporated by reference, and Z. Shen, P. E. Burrows, V. Bulovic, S. R. Forrest, and M. E. Thompson, "Three-Color, Tunable, Organic Light-Emitting Devices," *Science,* 276, 2009–2011 (1997)).

A typical anode for an organic electroluminescent device is indium-tin-oxide (ITO) sputtered onto a transparent substrate such as plastic or glass. Suitable substrates include, for example, glass, transparent plastics such as polyolefins, polyethersulfones, polycarbonates, polyesters, polyarylates, and polymeric multilayer films, ITO coated barrier films such as the Plastic Film Conductor available from 3M Optical Systems Division, surface-treated films, and selected polyimides. In some embodiments, the substrate has barrier properties matching those of the protective (or counter electrode) film. Flexible rolls of glass may also be used. Such a material may be laminated to a polymer carrier for better structural integrity.

The anode material coating the substrate is electrically conductive and may be optically transparent or semi-transparent. In addition to ITO, suitable anode materials include indium oxide, fluorine tin oxide (FTO), zinc oxide, vanadium oxide, zinc-tin oxide, gold, platinum, palladium silver, other high work function metals, and combinations thereof. In practice, the anode is optionally coated with 10–200 Å of an ionic polymer such as PEDT or PANI to help planarize the surface and to modify the effective work function of the anode.

Typical cathodes include low work function metals such as aluminum, barium, calcium, samarium, magnesium, silver, magnesium/silver alloys, lithium, lithium fluoride, ytterbium, and alloys of calcium and magnesium.

As an example of a device structure, FIG. 1 illustrates an OEL display or device 100 that includes a device layer 110 and a substrate 120. Any other suitable display component can also be included with display 100. Optionally, additional optical elements or other devices suitable for use with electronic displays, devices, or lamps can be provided between display 100 and viewer position 140 as indicated by optional element 130.

In some embodiments like the one shown, device layer 110 includes one or more OEL devices that emit light through the substrate toward a viewer position 140. The viewer position 140 is used generically to indicate an intended destination for the emitted light whether it be an actual human observer, a screen, an optical component, an electronic device, or the like. In other embodiments (not shown), device layer 110 is positioned between substrate 120 and the viewer position 140. The device configuration shown in FIG. 1 (termed "bottom emitting") may be used when substrate 120 is transmissive to light emitted by device layer 110 and when a transparent conductive electrode is disposed in the device between the light emitting layer of the device and the substrate. The inverted configuration (termed "top emitting") may be used when substrate 120 does or does not transmit the light emitted by the device layer and the electrode disposed between the substrate and the light emitting layer of the device does not transmit the light emitted by the device.

Device layer 110 can include one or more OEL devices arranged in any suitable manner. For example, in lamp applications (e.g., backlights for liquid crystal display (LCD) modules), device layer 110 might constitute a single OEL device that spans an entire intended backlight area. Alternatively, in other lamp applications, device layer 110 might constitute a plurality of closely spaced devices that can be contemporaneously activated. For example, relatively small and closely spaced red, green, and blue light emitters can be patterned between common electrodes so that device layer 110 appears to emit white light when the emitters are activated. Other arrangements for backlight applications are also contemplated.

In direct view or other display applications, it may be desirable for device layer 110 to include a plurality of independently addressable OEL devices or elements that emit the same or different colors. Each device might represent a separate pixel or a separate sub-pixel of a pixilated display (e.g., high resolution display), a separate segment or sub-segment of a segmented display (e.g., low information content display), or a separate icon, portion of an icon, or lamp for an icon (e.g., indicator applications).

Referring back to FIG. 1, device layer 110 is disposed on substrate 120. Substrate 120 can be any substrate suitable for OEL device and display applications. For example, substrate 120 can include glass, clear plastic, or other suitable material(s) that are substantially transparent to visible light. Substrate 120 can also be opaque to visible light, for example stainless steel, crystalline silicon, poly-silicon, or the like. Because some materials in OEL devices can be particularly susceptible to damage due to exposure to oxygen or water, substrate 120 preferably provides an adequate environmental barrier, or is supplied with one or more layers, coatings, or laminates that provide an adequate environmental barrier.

Substrate 120 can also include any number of devices or components suitable in OEL devices and displays such as transistor arrays and other electronic devices; color filters, polarizers, wave plates, diffusers, and other optical devices; insulators, barrier ribs, black matrix, mask work and other such components; and the like. Generally, one or more electrodes will be coated, deposited, patterned, or otherwise disposed on substrate 120 before forming the remaining layer or layers of the OEL device or devices of the device layer 110. When a light transmissive substrate 120 is used and the OEL device or devices are bottom emitting, the electrode or electrodes that are disposed between the substrate 120 and the emissive material(s) are preferably substantially transparent to light, for example transparent conductive electrodes such as indium tin oxide (ITO) or any of a number of other transparent conductive oxides.

Element 130 can be any element or combination of elements suitable for use with OEL display or device 100. For example, element 130 can be a LCD module when device 100 is a backlight. One or more polarizers or other elements can be provided between the LCD module and the backlight device 100, for instance an absorbing or reflective clean-up polarizer. Alternatively, when device 100 is itself an information display, element 130 can include one or more of polarizers, wave plates, touch panels, antireflective coatings, anti-smudge coatings, projection screens, brightness enhancement films, or other optical components, coatings, user interface devices, or the like.

FIGS. 4A to 4D illustrate examples of different OEL device (for example, an organic light emitting diode) configurations of the present invention. Each configuration includes a substrate 250, an anode 252, a cathode 254, and a light emitting layer 256. The light emitting layer 256 can include a compound of Formula I or a composition containing a compound of Formula I in combination with a second compound that is a charge transporting material, a charge blocking material, a light emitting material, a color conversion material, a polymeric binder, or a combination thereof. The configurations of FIGS. 4C and 4D also include a hole transport layer 258 and the configurations of FIGS. 4B and 4D include an electron transport layer 260. These layers conduct holes from the anode or electrons from the cathode, respectively. The compounds and compositions of the present invention can be included in one or both of these layers. In some embodiments, the OEL devices of FIGS. 4B–4D include a compound or composition of the invention in one or both of the light emitting layer 256 and the electron transport layer 260.

The anode 252 and cathode 254 are typically formed using conducting materials such as metals, alloys, metallic compounds, metal oxides, conductive ceramics, conductive dispersions, and conductive polymers, including, for example, gold, platinum, palladium, aluminum, calcium, titanium, titanium nitride, indium tin oxide (ITO), fluorine tin oxide (FTO), and polyaniline. The anode 252 and the cathode 254 can be single layers of conducting materials or they can include multiple layers. For example, an anode or a cathode may include a layer of aluminum and a layer of gold, a layer of calcium and a layer of aluminum, a layer of aluminum and a layer of lithium fluoride, or a metal layer and a conductive organic layer.

The hole transport layer 258 facilitates the injection of holes from the anode into the device and their migration towards the recombination zone. The hole transport layer 258 can further act as a barrier for the passage of electrons to the anode 252. In some examples, the hole transport layer 258 can include, for example, a diamine derivative, such as N,N'-bis(3-methylphenyl)-N,N'-bis(phenyl)benzidine (also known as TPD) or N,N'-bis(1-naphthyl)-N,N'-bis(phenyl) benzidine (NPB), or a triarylamine derivative, such as, 4,4',4"-Tris(N,N-diphenylamino)triphenylamine (TDATA) or 4,4',4"-Tris(N-3-methylphenyl-N-phenylamino) triphenylamine (mTDATA). Other examples of materials that can be in the hole transport layer include copper phthalocyanine (CuPC); 1,3,5-Tris(4-diphenylaminophenyl) benzenes (TDAPBs); and other compounds such as those described in H. Fujikawa, et al., *Synthetic Metals*, 91, 161 (1997) and J. V. Grazulevicius, P. Strohriegl, "Charge-Transporting Polymers and Molecular Glasses", *Handbook of Advanced Electronic and Photonic Materials and Devices*, H. S. Nalwa (ed.), 10, 233–274 (2001), both of which are incorporated herein by reference.

The electron transport layer 260 facilitates the injection of electrons and their migration towards the recombination zone. The electron transport layer 260 can further act as a barrier for the passage of holes to the cathode 254, if desired. In some examples, the electron transport layer 260 can be formed using the organometallic compound tris(8-hydroxyquinolato)aluminum (Alq3). Other examples of electron transport materials useful in electron transport layer 260 include 1,3-bis[5-(4-(1,1-dimethylethyl)phenyl)-1,3,4-oxadiazol-2-yl]benzene, 2-(biphenyl-4-yl)-5-(4-(1,1-dimethylethyl)phenyl)-1,3,4-oxadiazole (tBuPBD) and other compounds described in C. H. Chen et al., *Macromol. Symp.*, 125, 1 (1997) and J. V. Grazulevicius et al., "Charge-Transporting Polymers and Molecular Glasses", *Handbook of Advanced Electronic and Photonic Materials and Devices*, H. S. Nalwa (ed.), 10, 233 (2001), both of which are incorporated herein by reference.

Figure 3:
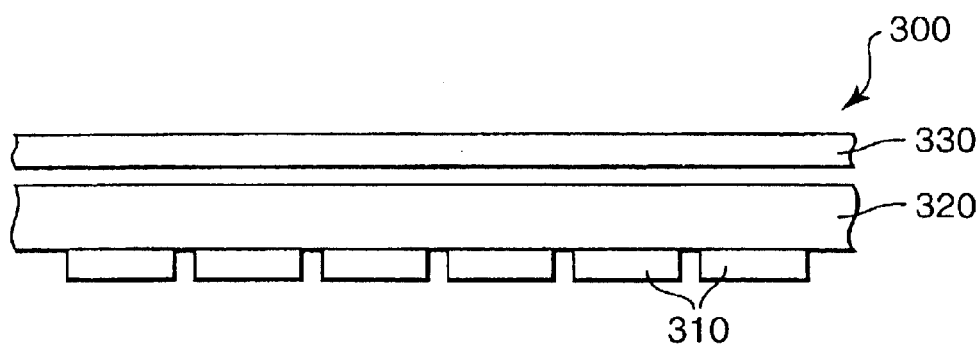
FIG. 3 is a schematic side view of an organic electroluminescent display.
Figure 4A:
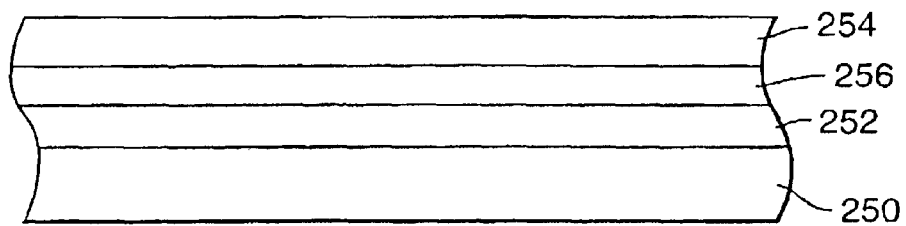
FIG. 4A is a schematic side view of a first embodiment of an organic electroluminescent device.
Figure 4B:
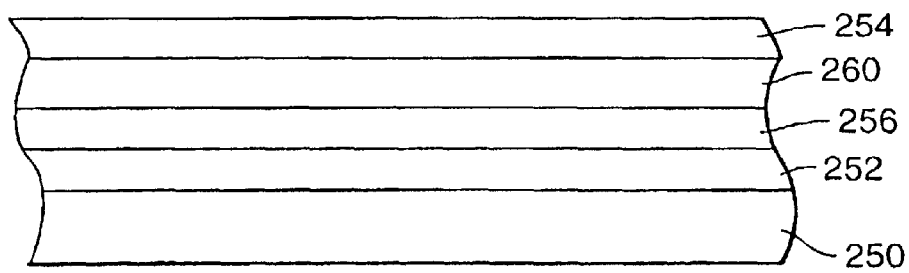
FIG. 4B is a schematic side view of a second embodiment of an organic electroluminescent device.
Figure 4C:
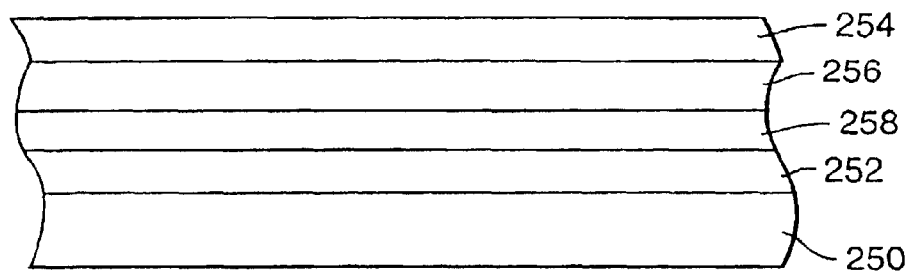
FIG. 4C is a schematic side view of a third embodiment of an organic electroluminescent device.
Figure 4D:
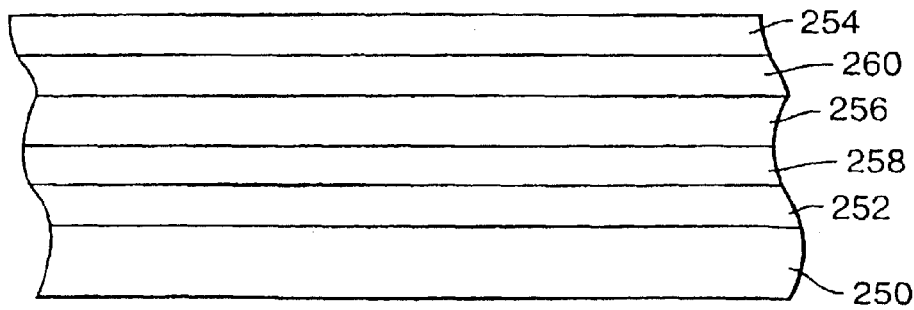
FIG. 4D is a schematic side view of a fourth embodiment of an organic electroluminescent device.

The present invention contemplates light emitting OEL displays and devices that include a compound according to Formula I or a composition that includes a compound according to Formula I in addition to a second compound that is a charge transporting material, a charge blocking material, a light emitting material, a color conversion material, a polymeric binder, or a combination thereof. In one embodiment, OEL displays can be made that emit light and that have adjacent devices or elements that can emit light having different color. For example, FIG. 3 shows an OEL display 300 that includes a plurality of OEL elements 310 adjacent to each other and disposed on a substrate 320. Two or more adjacent elements 310 can be made to emit different colors of light, for example red, green, and blue. One or more of elements 310 include a compound or composition of the present invention.

The separation shown between elements 310 is for illustrative purposes only. Adjacent devices may be separated, in contact, overlapping, etc., or different combinations of these in more than one direction on the display substrate. For example, a pattern of parallel striped transparent conductive anodes can be formed on the substrate followed by a striped pattern of a hole transport material and a striped repeating pattern of red, green, and blue light emitting LEP layers, followed by a striped pattern of cathodes, the cathode stripes oriented perpendicular to the anode stripes. Such a construction may be suitable for forming passive matrix displays. In other embodiments, transparent conductive anode pads can be provided in a two-dimensional pattern on the substrate and associated with addressing electronics such as one or more transistors, capacitors, etc., such as are suitable for making active matrix displays. Other layers, including the light emitting layer(s) can then be coated or deposited as a single layer or can be patterned (e.g., parallel stripes, two-dimensional pattern commensurate with the anodes, etc.) over the anodes or electronic devices. Any other suitable construction is also contemplated by the present invention.

In one embodiment, display 300 can be a multiple color display. In exemplary embodiments, each of the elements 310 emits light. There are many displays and devices constructions covered by the general construction illustrated in FIG. 3. Some of those constructions are discussed as follows.

Constructions of OEL backlights can include bare or circuitized substrates, anodes, cathodes, hole transport layers, electron transport layers, hole injection layers, electron injection layers, emissive layers, color changing layers, and other layers and materials suitable in OEL devices. Constructions can also include polarizers, diffusers, light guides, lenses, light control films, brightness enhancement films, and the like. Applications include white or single color large area single pixel lamps, for example where an emissive material is provided by thermal stamp transfer, lamination transfer, resistive head thermal printing, or the like; white or single color large area single electrode pair lamps that have a large number of closely spaced emissive layers patterned by laser induced thermal transfer; and tunable color multiple electrode large area lamps.

Constructions of low resolution OEL displays can include bare or circuitized substrates, anodes, cathodes, hole transport layers, electron transport layers, hole injection layers, electron injection layers, emissive layers, color changing layers, and other layers and materials suitable in OEL devices. Constructions can also include polarizers, diffusers, light guides, lenses, light control films, brightness enhancement films, and the like. Applications include graphic indicator lamps (e.g., icons); segmented alphanumeric displays (e.g., appliance time indicators); small monochrome passive or active matrix displays; small monochrome passive or active matrix displays plus graphic indicator lamps as part of an integrated display (e.g., cell phone displays); large area pixel display tiles (e.g., a plurality of modules, or tiles, each having a relatively small number of pixels), such as may be suitable for outdoor display used; and security display applications.

Constructions of high resolution OEL displays can include bare or circuitized substrates, anodes, cathodes, hole transport layers, electron transport layers, hole injection layers, electron injection layers, emissive layers, color changing layers, and other layers and materials suitable in OEL devices. Constructions can also include polarizers, diffusers, light guides, lenses, light control films, brightness enhancement films, and the like. Applications include active or passive matrix multicolor or full color displays; active or passive matrix multicolor or full color displays plus segmented or graphic indicator lamps (e.g., laser induced transfer of high resolution devices plus thermal hot stamp of icons on the same substrate); and security display applications. One particularly useful embodiment for this type of thermally patterned construction includes the high resolution transfer of red, green and blue emitting emissive layers onto a common substrate. High resolution transfer means that the rms (root mean square) edge roughness of the transferred material is 5 micrometers or less.

Methods for Fabricating OEL Layers

Another aspect of the invention provides a method for preparing organic electroluminescent devices. The devices include an organic emissive structure that includes a compound of Formula I or a composition that includes a compound of Formula I in addition to a second compound that is a light emitting material, a charge transporting material, a charge blocking material, a color conversion material, a polymeric binder, or a combination thereof.

In certain applications, it is desirable to pattern one or more layers of an organic electronic device onto a substrate, for example, to fabricate emissive displays. Methods for patterning include selective transfer, for example laser thermal transfer, photolithographic patterning, inkjet printing, screen printing, and the like.

One aspect of the present invention provides methods for making an organic electronic device. A donor sheet is prepared that has a transfer layer. The transfer layer includes a compound according to Formula I or a composition containing a compound according to Formula I and a second compound that is a light emitting material, a charge transporting material, a charge blocking material, a color conversion material, a polymeric binder, or a combination thereof. The method of preparing an organic electronic device includes preparing a donor sheet having a transfer layer and transferring the transfer layer from the donor layer to a receptor sheet.

A particularly useful method of forming organic electronic devices of the present invention, for example, organic electroluminescent devices, includes transferring one or more transfer layers by laser thermal patterning. This method is described in, for example, U.S. Pat. Nos. 6,358,664; 6,284,425; 6,242,152; 6,228,555; 6,228,543; 6,221,553; 6,221,543; 6,214,520; 6,194,119; 6,114,088; 5,998,085; 5,725,989; 5,710,097; 5,695,907; 5,693,446[, 6,485,884 and 6,521,324; WO02/22374; and U.S. Patent Publication Nos. 2003-0068525 and 2003-0124265, all of which are incorporated herein by reference. The effectiveness of the patterning process can depend upon the physical properties of the transfer layer.

One parameter is the cohesive, or film strength, of the transfer layer. During imaging, the transfer layer preferably breaks cleanly along the line dividing imaged and unimaged regions to form the edge of a pattern. Highly conjugated polymers that exist in extended chain conformations, such as polyphenylenevinylenes, can have high tensile strengths and elastic moduli comparable to that of polyaramide fibers. In practice, clean edge formation during the laser thermal imaging of light emitting polymers can be challenging. The undesired consequence of poor edge formation is rough, torn, or ragged edges on the transferred pattern. Another parameter is the strength of the bond formed between the transfer layer and the receptor surface. This strength may be influenced by the solubility parameter compatibility of the transfer layer and the receptor surface.

In some instances, it is desirable to select the material on the substrate surface and the material to be transferred (e.g., a compound or composition of the present invention) such that the solubility parameters are compatible to improve or even make possible thermal transfer or other patterning methods. As an example, the materials can be selected such that the difference in these solubility parameters is no more than 4 $J^{1/2}$ $cm^{-3/2}$ and, preferably, no more than 2 $J^{1/2}$ $cm^{-3/2}$ as determined according to *Properties of Polymers; Their Correlation with Chemical Structure; Their Numerical Estimation and Prediction from Additive Group Contributions*, third edition, edited by D. W. Van Krevelen; Elsevier Science Publishers B. V., 1990, Chapter 7, pp 189–225, incorporated herein by reference.

The solubility parameter of a materials can be determined from measurements of the extent of equilibrium swelling of the material in a range of solvents of differing solubility parameters. The solubility parameters of the solvents themselves can be determined from their heats of evaporation. The solubility parameter $\delta$ is related to the cohesive energy $E_{coh}$ and the specific volume V by the relationship $\delta=(E_{coh}/V)^{1/2}$. For solvents of low molecular weight, the cohesive energy is closely related to the molar heat of evaporation $\Delta H_{vap}$ according to $E_{coh}=\Delta H_{vap}-p\Delta V=\Delta H_{vap}-RT$. Thus, $E_{coh}$ and $\delta$ can be calculated from the heat of evaporation of the solvent or from the course of the vapor pressure as a function of temperature.

Because some materials such as polymers cannot be evaporated, indirect methods have to be used for determination of their solubility parameter. To determine the solubility parameter of the polymer, the equilibrium swelling of the polymer in a variety of solvents of differing $\delta$ is measured and a plot of equilibrium swelling of the polymer vs. the solubility parameter of the solvents is generated. The solubility parameter of the polymer is defined as the point on this plot where maximum swelling is obtained. Swelling will be less for solvents having solubility parameters that are less than or greater than that of the polymer. There are several methods for theoretically estimating the solubility parameter of a polymer based on the additive contributions of functional groups present in the polymer as outlined in the above-cited reference.

Organic electronic devices containing a compound or composition of the present invention can be made at least in part by selective thermal transfer of the compound or composition from a thermal transfer donor sheet to a desired receptor substrate. For example, displays and lamps can be made by coating a light emitting layer on a donor sheet and then selectively transferring the light emitting layer alone or along with other device layers or materials to the display (receptor) substrate.

Figure 2:
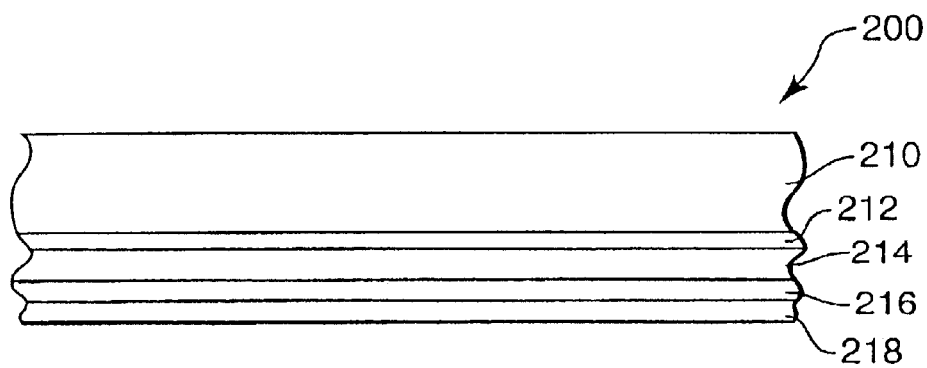
FIG. 2 is a schematic side view of a donor sheet for transferring materials.

FIG. 2 shows an example of a thermal transfer donor sheet 200 suitable for use in the present invention. Donor element 200 includes a base substrate 210, an optional underlayer 212, an optional light-to-heat conversion layer (LTHC layer) 214, an optional interlayer 216, and a transfer layer 218 comprising a compound according to Formula I or a composition that includes a compound according to Formula I in addition to a second compound that is a charge transporting material, a charge blocking material, a light emitting material, a color conversion material, a polymeric binder, or a combination thereof. Other compounds, compositions, or layers can also be present. Examples of suitable donors or layers of donors are disclosed in U.S. Pat. Nos. 6,358,664; 6,284,425; 6,242,152; 6,228,555; 6,228,543; 6,221,553; 6,221,543; 6,214,520; 6,194,119; 6,114,088; 5,998,085; 5,725,989; 5,710,097; 5,695,907; 5,693,446; 6,485,884 and 6,521,324; WO02/22374; and U.S. Patent Publication Nos. 2003-0068525 and 2003-0124265, all of which are incorporated herein by reference.

Emissive organic materials, including LEPs or molecularly doped polymer films that include the compounds or compositions of this invention, can be transferred or selectively transferred in the transfer layer from a donor sheet to a receptor substrate by placing the transfer layer of the donor element adjacent to the receptor and selectively heating the donor element. Methods for the transfer or the selective transfer are described in, for example, U.S. Pat. No. 6,242,152. Transfer layers can also be transferred from donor sheets without selectively transferring the transfer layer. For example, a transfer layer can be formed on a donor substrate that, in essence, acts as a temporary liner that can be released after the transfer layer is contacted to a receptor substrate, typically with the application of heat or pressure. Such a method, referred to as lamination transfer, can be used to transfer the entire transfer layer, or a large portion thereof, to the receptor.

Materials from separate donor sheets can be transferred adjacent to other materials on a receptor to form adjacent devices, portions of adjacent devices, or different portions of the same device. Alternatively, materials from separate donor sheets can be transferred directly on top of, or in partial overlying registration with, other layers or materials previously patterned onto the receptor by thermal transfer or some other method (e.g., photolithography, deposition through a shadow mask, etc.). A variety of other combinations of two or more donor sheets can be used to form a device, each donor sheet forming one or more portions of the device. It will be understood that other portions of these devices, or other devices on the receptor, may be formed in whole or in part by any suitable process including photolithographic processes, ink jet processes, and various other printing or mask-based processes, whether conventionally used or newly developed.

In FIG. 2 the donor substrate 210 can be a polymer film. Suitable films are described in U.S. Pat. Nos. 6,242,152 and 6,228,555, incorporated herein by reference.

In FIG. 2 optional underlayer 212 may be coated or otherwise disposed between a donor substrate and the LTHC layer, for example to control heat flow between the substrate and the LTHC layer during imaging or to provide mechanical stability to the donor element for storage, handling, donor processing, or imaging. Examples of suitable underlayers and methods of providing underlayers are disclosed in U.S. Pat. No. 6,228,555 and in co-assigned U.S. patent application Ser. No. 09/743,114, incorporated herein by reference.

The underlayer can include materials that impart desired mechanical or thermal properties to the donor element. For example, the underlayer can include materials that exhibit a low specific heat×density or low thermal conductivity relative to the donor substrate. Such an underlayer may be used to increase heat flow to the transfer layer, for example to improve the imaging sensitivity of the donor.

The underlayer may also include materials for their mechanical properties or for adhesion between the substrate and the LTHC. Using an underlayer that improves adhesion between the substrate and the LTHC layer may result in less distortion in the transferred image. As an example, in some cases an underlayer can be used that reduces or eliminates delamination or separation of the LTHC layer that might otherwise occur during imaging of the donor media. This can reduce the amount of physical distortion exhibited by transferred portions of the transfer layer. In other cases, however it may be desirable to employ underlayers that promote at least some degree of separation between or among layers during imaging, for example to produce an air gap between layers during imaging that can provide a thermal insulating function. Separation during imaging may also provide a channel for the release of gases that may be generated by heating of the LTHC layer during imaging. Providing such a channel may lead to fewer imaging defects.

The underlayer may be substantially transparent at the imaging wavelength, or may also be at least partially absorptive or reflective of imaging radiation. Attenuation or reflection of imaging radiation by the underlayer may be used to control heat generation during imaging.

In FIG. 2, an LTHC layer 214 can be included in donor sheets of the present invention to couple irradiation energy into the donor sheet. The LTHC layer preferably includes a radiation absorber that absorbs incident radiation (e.g., laser light) and converts at least a portion of the incident radiation into heat to enable transfer of the transfer layer from the donor sheet to the receptor. Suitable LTHC layers are described in, for example, U.S. Pat. No. 6,242,152, and 6,228,555, incorporated herein by reference.

In FIG. 2, an optional: interlayer 216 may be disposed between the LTHC layer 214 and transfer layer 218. The interlayer can be used, for example, to minimize damage and contamination of the transferred portion of the transfer layer and may also reduce distortion in the transferred portion of the transfer layer. The interlayer may also influence the adhesion of the transfer layer to the rest of the donor sheet. Typically, the interlayer has high thermal resistance. Preferably, the interlayer does not distort or chemically decompose under the imaging conditions, particularly to an extent that renders the transferred image non-functional. The interlayer typically remains in contact with the LTHC layer during the transfer process and is not substantially transferred with the transfer layer. Suitable interlayers are described in, for example, U.S. Pat. Nos. 6,242,152 and 6,228,555, incorporated herein by reference.

In FIG. 2, a thermal transfer layer 218 is included in donor sheet 200. Transfer layer 218 includes a compound or composition of the present invention and can include any other suitable material or materials, disposed in one or more layers, alone or in combination with other materials. Transfer layer 218 is capable of being selectively transferred as a unit or in portions by any suitable transfer mechanism when the donor element is exposed to direct heating or to imaging radiation that can be absorbed by light-to-heat converter material and converted into heat.

The present invention further provides a light emitting transfer layer that includes a compound of Formula I or a composition that includes a compound of Formula I in addition to a second compound that is a light emitting material, a charge transporting material, a charge blocking material, a color conversion material, a polymeric binder, or a combination thereof. One way of providing the transfer layer is by solution coating the light emitting material onto the donor substrate or any of the layers described supra, i.e., underlayer, interlayer, light-to-heat converting layer. In this method, the light emitting material can be solubilized by addition of a suitable compatible solvent, and coated onto the donor substrate or any one of the above layers by spin-coating, gravure coating, Mayer rod coating, knife coating and the like. The solvent chosen preferably does not undesirably interact with (e.g., swell or dissolve) any of the already existing layers in the donor sheet. The coating can then be annealed and the solvent evaporated to leave a transfer layer.

The transfer layer can then be selectively thermally transferred from the resulting donor sheet or element to a proximately located receptor substrate. There can be, if desired, more than one transfer layer so that a multilayer construction is transferred using a single donor sheet. Suitable receptor substrates are described, for example, in U.S. Pat. Nos. 6,242,152 and 6,228,555, incorporated herein by reference.

Receptor substrates can be pre-patterned with any one or more of electrodes, transistors, capacitors, insulator ribs, spacers, color filters, black matrix, hole transport layers, electron transport layers, and other elements useful for electronic displays or other devices.

The invention is further described by the following examples, which are provided for illustration only and are not intended to be limiting in any way.

EXAMPLES

Example 1

Synthesis of 2-(2,5-Bis-phenylethynylphenyl)-5-(4-octyloxyphenyl)-[1,3,4]oxadiazole

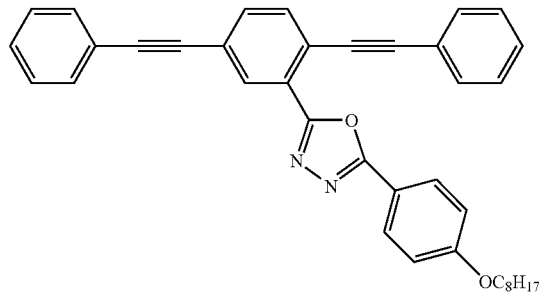

Part A: Synthesis of Methyl 4-octoxybenzoate

Into a flask were introduced methyl 4-hydroxybenzoate (251.0 g, 1.65 mol), potassium carbonate (276.37 g, 1.99 mol) and 1200 g of acetone. This was refluxed for 45 min followed by the drop-wise addition of 1-octylbromide (386.17 g, 1.99 mol) over a 1 hour period. The reaction mixture was refluxed for two days. Filtration of the cooled reaction mixture and evaporation of the filtrate gave an oil. This was taken up in ethyl acetate and extracted with 5% NaOH (2×100 ml) followed by water (2×100 ml). The organic layer was dried (MgSO$_4$), concentrated, and transferred to a pre-weighed 1L three-necked flask. The contents of the flask were subjected to high vacuum distillation to remove the excess 1-octylbromide. The pot residue gave 376 g (86% yield) of methyl 4-octoxybenzoate.

Part B: Synthesis of 4-Octyloxybenzoic Acid Hydrazide

To the contents of the flask from Part A was added 98% hydrazine (387.14 g). This was refluxed for 5 hours (106° C.). The cooled solution was poured into 3L of water and the precipitated solid filtered, washed with copious amounts of water and dried in vacuum to give 343 g (91% yield). 4-octyloxybenzoic acid hydrazide. Melting point 90° C.

Part C: Synthesis of 2,5-Dibromobenzoyl Chloride

Into a 2 L flask fitted with a reflux condenser and magnetic stir-bar was introduced 2,5-dibromobenzoic acid (50.0 g, 0.1786 mol) and thionyl chloride (150 mL, 2.04 mol). The mixture was refluxed for 8 hours. Most of the thionyl chloride was distilled off followed by removal of the remainder by rotary evaporation. Distillation gave 40 g of 2,5-dibromobenzoyl chloride. (pot temperature 110° C.; distillation temp 70° C./0.70 mm Hg).

Part D: Synthesis of 2,5-Dibromo-N'-[4-(octyloxy)benzoyl]benzohydrazide

Under a blanket of nitrogen, 2,5-dibromobenzoyl chloride (57.43 g, 0.11925 mol) was added to a solution of 4-octyloxybenzoic acid hydrazide (50.88 g, 0.1925 mol) and triethylamine (27 mL, 19.48 g, 0.1925 mol) in 800 mL of methylene chloride. The reaction mixture was stirred for 5 hours at room temperature. The precipitated solid was filtered off and re-crystallized from hot DMF/water gave 79.38 g (78% yield) 2,5-dibromo-N'-[4-(octyloxy)benzoyl]benzohydrazide.

Part E: Synthesis of 2-(2,5-Dibromophenyl)-5-[4-(octyloxy)phenyl]-1,3,4-oxadiazole A mixture of 2,5-dibromo-N'-[4-(octyloxy)benzoyl]benzohydrazide (39.1 g, 0.0743 mol) and phosphorus oxychloride (203 mL) was refluxed for 8 hrs. Unreacted phosphorus oxychloride was distilled off and the residue poured onto crushed ice. The precipitated solid was collected by filtration and re-crystallized from EtOH/water to give 33.6 g (89% yield) 2-(2,5-dibromophenyl)-5-[4-(octyloxy)phenyl]1,3,4-oxadiazole.

Part F: Synthesis of 2-(2,5-Bis-phenylethynylphenyl)-5-(4-octyloxyphenyl)-[1,3,4]oxadiazole Pd(PPh$_3$)$_4$ (71.6 mg, 0.1 mmol) and CuI (23.6 mg, 0.1 mmol) were added to a mixture of 2,(2,5-dibromophenyl)-5-[4-octyloxy)phenyl]-1,3,4-oxadiazole (3.20 g, 6.3 mmol) and phenyl acetylene (1.29 g, 12.6 mmol) in 20 mL of dry Et$_3$N. The reaction mixture was magnetically stirred for 3 h under reflux. The cooled reaction mixture was poured into an excess amount of methanol and the precipitate was collected by filtration. Re-crystallization from methylene chloride/hexane gave 2-(2,5-bis-phenylethynylphenyl)-5-(4-octyloxyphenyl)-[1,3,4]oxadiazole (2.50 g, 72% yield).

$^1$H-NMR (500 MHz, C$_6$D$_6$) δ 8.45 (d, J=1.46 Hz, 1H), 8.05 (d, J=9.03 Hz, 2H), 7.65 (dd, J=1.95, 8.05 Hz, 2H), 7.49 (dd, J=1.71, 7.81 Hz, 1H), 7.37 (d, J=8.06 Hz, 1H), 7.27 (dd, J=1.7, 8.05 Hz, 2H), 7.01–6.98 (m, 6H) 6.71 (d, J=9.04 Hz, 2H) 3.52 (t, J=6.35 Hz, 2H, CH$_2$O), 1.55 (m, 2H, CH$_2$), 1.3–1.22 (m, 10H, CH$_2$ chain), 0.90 (t, J=6.83 Hz, 3H, CH$_3$). $^{13}$C-NMR (100 MHz, C$_6$D$_6$) δ 164.93, 163.14, 162.16, 134.06, 133.26, 132.28, 132.03, 129.16, 128.7, 126.51, 123.93, 123.67, 123.25, 121.68, 117.06, 115.1, 97.00, 92.86, 88.84, 88.77, 68.08, 32.15, 29.68, 29.6, 29.4, 26.29, 23.04, 14.32.

Example 2

Synthesis of 2-(3,5-Bis-phenylethynylphenyl)-5-(4-octyloxyphenyl)-[1,3,4]oxadiazole

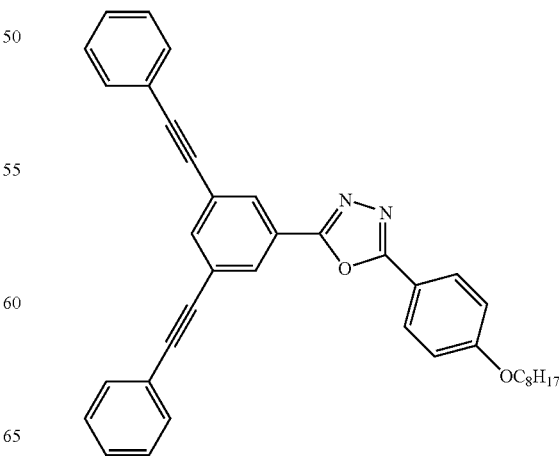

Part A: Synthesis of 2-(3,5-Dibromophenyl)-5-[4-(octyloxy)phenyl]-1,3,4-oxadiazole By the general method for the synthesis of 2-(2,5-dibromophenyl)-5-[4-(octyloxy)phenyl]-1,3,4-oxadiazole in Example 1, the reaction of 3,5-dibromobenzoyl chloride (20.13 g, 0.06747 mole) with 4-octyloxybenzoic acid hydrazide (17 g, 0.06747 mole) gave the intermediate 3,5-dibromo-N'-[4-(octyloxy)benzoyl]benzohydrazide (12.87 g, 36% yield). Cyclocondensation of the intermediate 3,5-dibromo-N'-[4-(octyloxy)benzoyl]-benzohydrazide (12.17 g) with $POCl_3$ (63 mL) gave the required 2-(3,5-dibromophenyl)-5-[4-(octyloxy)phenyl]-1,3,4-oxadiazole (6.12 g, 52% yield).

Part B: Synthesis of 2-(3,5-Bis-phenylethynylphenyl)-5-(4-octyloxyphenyl)-[1,3,4]oxadiazole Using the general method of Example 1, the reaction of $Pd(PPh_3)_4$ (71.6 mg, 0.1 mmol) and CuI (23.6 mg, 0.1 mmol) with a mixture of 2,(3,5-dibromophenyl)-5-[4-octylxoy)phenyl]-1,3,4-oxadiazole (3.20 g, 6.3 mmol) and phenyl acetylene (1.29 g, 12.6 mmol) in 20 mL of dry $Et_3N$ gave, after work-up 2-(3,5-bis-pyren-1-ylethynyl-phenyl)-5-(4-octyloxy-phenyl)-[1,3,4]oxadiazole (2.88 g, 83% yield). DSC and photoluminescence data are given in Table 1.

Example 3

Synthesis of 2-(3,5-Bis-pyren-1-ylethynylphenyl)-5-(4-octyloxyphenyl)-[1,3,4]oxadiazole

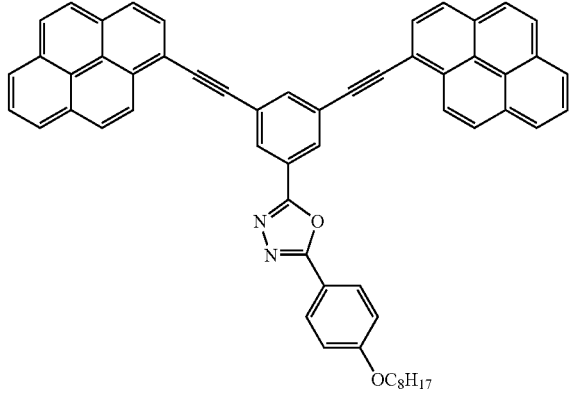

Using the general method of Example 1, the reaction of $Pd(PPh_3)_4$ (127.5 mg, 0.1 mmol) and CuI (42.0 mg, 0.2 mmol) with a mixture of 2,(3,5-dibromophenyl)-5-[4-octylxoy)phenyl]-1,3,4-oxadiazole (5.70 g, 11.2 mmol) and 1-etyylpyrene (Lancaster Chemicals)(1.29 g, 12.6 mmol) in 50 mL of dry $Et_3N$ gave, after work-up and recrystallization from methylene chloride/hexane, 2-(3,5-bis-pyren-1-ylethynyl-phenyl)-5-(4-octyloxy-phenyl)-[1,3,4]oxadiazole (6.25 g, 70% yield).

$^1$H-NMR 600 MHz ($C_6D_6$) δ 8.89 (d, J=9.06 Hz, 2H, pyrene), 8.5 (d, J=1.29 Hz, 2H), 8.22 (d, J=7.76 Hz, 2H), 8.14 (s, 1H), 8.01 (d, J=6.79 Hz, 2H), 7.99 (d, J=9.06 Hz, 2H, pyrene), 7.94 (d, J=7.44 Hz, 2H, pyrene), 7.92 (d, J=7.44 Hz, 2H, pyrene), 7.81 (d, J=8.41 Hz, 2H, pyrene), 7.78 (d, J=7.76 Hz, 2H, pyrene), 7.76 (d, J=7.44 Hz, 2H, pyrene), 7.72 (d, J=8.74 Hz, 2H, pyrene), 6.77 (d, J=8.74 Hz, 2H), 3.57 (t, J=6.47 Hz, 2H, $CH_2$—O), 1.62, (m, 2H, $CH_2$), 1.38–1.29 (m, 10 H, $CH_2$ chain), 0.96 (t, J=7.12 Hz, 3H, $CH_3$). DSC and photoluminescence data are given in Table 1.

Example 4

Synthesis of 2-(2,5-Bis-pyren-1-ylethynylphenyl)-5-(4-octyloxyphenyl)-[1,3,4]oxadiazole

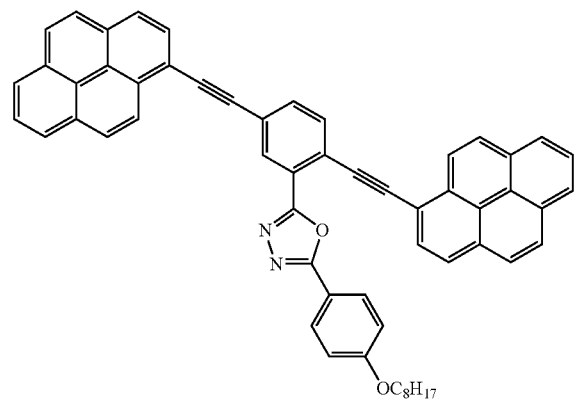

Using the general method of Example 1, the reaction of $Pd(PPh_3)_4$ (24.0 mg, 0.02 mmol) and CuI (8.0 mg, 0.04 mmol) with a mixture of 2,(2,5-dibromophenyl)-5-[4-octylxoy)phenyl]-1,3,4-oxadiazole (1.07 g, 2.11 mmol) and 1-ethynylpyrene (0.96 g, 4.25 mmol) in 80 mL of dry $Et_3N$ gave, after work-up 2-(2,5-bis-pyren-1-ylethynylphenyl)-5-(4-octyloxy-phenyl)-[1,3,4]oxadiazole.

$^1$H 500 MHz ($C_6D_6$) δ 9.41 (d, J=9.03 Hz, 1H, pyrene), 8.98 (d, J=9.04 Hz, 1H, pyrene), 8.68 (d, J=1.46 Hz, 1H), 8.45 (d, J=8.06 1H, pyrene), 8.28 (d, J=7.81 Hz, 1H), 8.21–8.15 (m, 3H, pyrene), 8.00–7.97 (m, 4H, pyrene), 7.88–7.86 (m, 4H, pyrene), 7.82–7.78 (m, 5H, pyrene), 7.76 (d, J=8.06 Hz, 1H), 7.62 (dd, J=1.71, 7.81 Hz, 1H), 6.67 (d, 2H), 3.46 (t, J=6.59 Hz, 2H, $CH_2$—O), 1.57 (m, 2H, $CH_2$), 1.36–1.27 (m, 10H, $CH_2$ chain), 0.99 (t, J=7.08 Hz, 3H, $CH_3$). Carbons signals observed that were resolved from the deuterated benzene are shown below. Not all of the carbons were accounted for. $^{13}$C 100 MHz ($C_6D_6$) δ 165.18, 163.22, 162.15, 135.55, 134.55, 133.48, 133.18, 132.66, 132.37, 132.21, 132.12, 131.68, 131.44, 131.54, 130.59, 130.19, 129.60, 139.27, 129.24, 129.06, 127.44, 126.70, 126.50, 126.41, 126.19, 126.16, 126.03, 125.83, 125.10, 124.97, 124.91, 124.83, 124.18, 122.24, 118.17, 117.64, 117.00, 115.05, 94.58, 94.37, 92.49, 68.00, 32.13, 29.63, 29.57, 29.33, 26.24, 23.01, 14.28. DSC and photoluminescence data are given in Table 1.

Example 5

Synthesis of 2-[2,5-Bis-(3-trifluoromethyl-phenylethynyl)-phenyl]-5-(4-octyloxyphenyl)-[1,3,4]oxadiazole

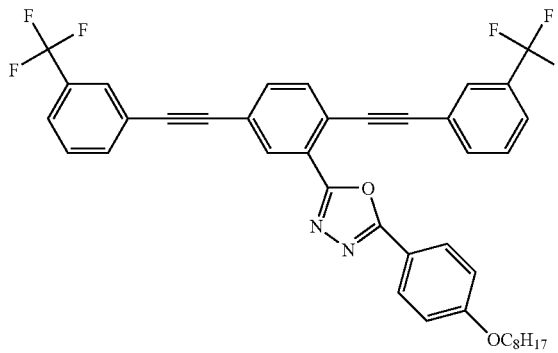

Using the general method of Example 1, the reaction of Pd(PPh$_3$)$_4$ (123.1 mg, 0.106 mmol) and CuI (40.6 mg, 0.213 mmol) with a mixture of 2(2,5-dibromophenyl)-5-[4-octylxoy)phenyl]-1,3,4-oxadiazole (5.50 g, 10.8 mmol) and 3-ethynyl-α,α,α-trifluorotoluene (3.69 g, 21.7 mmol) in 80 mL of dry Et$_3$N gave, after work-up, 2-[2,5-bis-(3-trifluoromethyl-phenylethynyl)-phenyl]-5-(4-octyloxyphenyl)-[1,3,4]oxadiazole (6.1 g, 80% yield).

$^1$H 500 MHz (C$_6$D$_6$) δ 8.43 (d, J=1.46 Hz, 1H), 8.04 (d, J=8.79 Hz, 2H), 7.9 (s, 1H) 7.76 (s, 1H), 7.60 (d, J=7.82 Hz, 1H), 7.38 (dd, J=0.49, 8.05 Hz, 1H), 7.34 (d, J=7.82 Hz, 1H), 7.28 (dd, J=1.71, 8.05 Hz, 1H), 7.16 (d, J=8.09 Hz, 2H), 6.77 (m, 2H), 6.74 (d, J=8.79 Hz, 2H), 3.57 (t, J=6.59 Hz, 2H, CH$_2$—O), 1.56 (m, 2H, CH$_2$), 1.31–1.23 (m, 10H, CH$_2$ chain), 0.90 (t, J=7.08 Hz, 3H, CH$_3$); $^{13}$C 100 MHz (C$_6$D$_6$) δ 165.10, 162.81, 162.38, 135.34, 134.84, 134.25, 133.3, 132.31, 129.29, 129.24, 129.08, 126.74, 125.50, 125.47, 125.43, 124.36, 123.89, 123.71, 121.36, 116.76, 115.22, 95.36, 91.22, 89.90, 68.15, 32.15, 29.66, 29.6, 29.37, 26.28, 23.04, 14.32. DSC and photoluminescence data are given in Table 1.

TABLE 1

Tg, DSC and Photoluminescence Characterization of Compounds where n = 1

| Example | DSC MP (° C.) | Tg (° C.) | Abs (nm) | Excitation (nm) | Em (nm) |
|---|---|---|---|---|---|
| 2 | 149 | — | 308 |  | 378, 398 |
| 3 | 197 | 74 | 285, 300, 369, 397 | 300 | 408, 428 (sh) |
| 4 | — | 67 | 289, 413 | 289 | 475 |
| 5 | 144 | — | 308 | 308 | 418 |

Figure 5:
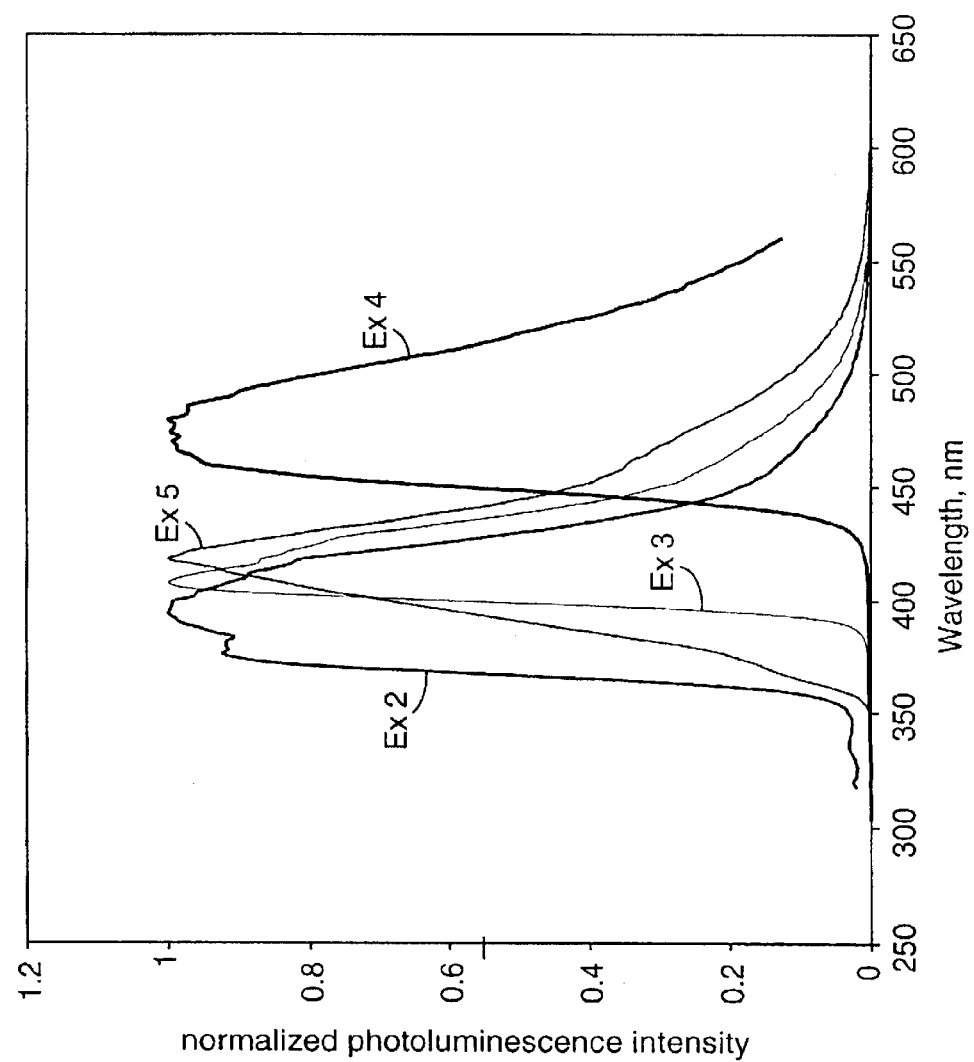
FIG. 5 depicts the photoluminescence spectra for various disclosed compounds.

DSC at 20° C./min in nitrogen atmosphere;
Abs (10 μm solution in dichloroethane)
sh = shoulder The photoluminescence spectra of Examples 2 to 5 are shown in FIG. 5.

Example 6

Synthesis of 2-(3-Bromo-5-phenylethynyl-phenyl)-5-(4-octyloxyphenyl)-[1,3,4]oxadiazole

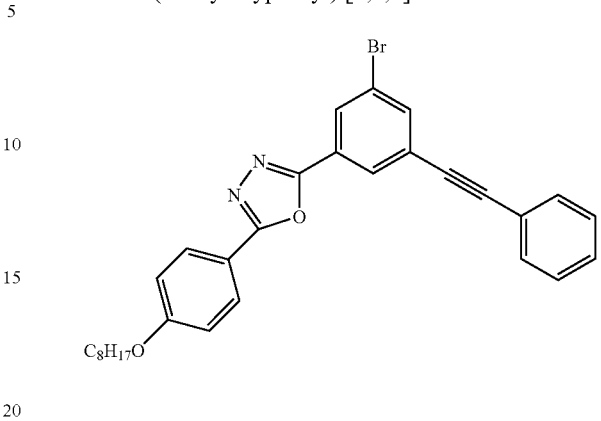

To a 75 mL solution of Et$_3$N, was added 2-(3,5-dibromophenyl)-5-[4-(octyloxy)phenyl]-1,3,4-oxadiazole (5.08 g, 0.01 mol), phenylacetylene (1.29 g, 0.0126 mol), copper (I) iodide (23.6 mg, 0.124 mmol) and Pd(PPh$_3$)$_4$ (70 mg, 0.063 mmol). The mixture was heated at 90° C. for 3 hours and filtered while hot. On cooling the filtrate gave a solid that was collected by filtration and washed with methanol. An excess or methanol was added to the filtrate to give a further crop of material. Column chromatography of the combined solids (hexane/ethyl acetate mixtures of concentrations up to 10% ethyl acetate) gave un-reacted 2-(3,5-dibromophenyl)-5-[4-(octyloxy)phenyl]1,3,4-oxadiazole followed by mixtures of 2-(3-bromo-5-phenylethynyl-phenyl)-5-(4-octyloxyphenyl)-[1,3,4]oxadiazole and 2-(2,4-bis-phenylethynylphenyl)-5-(4-octyloxyphenyl)-[1,3,4]oxadiazole. Repeated crystallization from hot hexane gave pure 2-(3-bromo-5-phenylethynyl-phenyl)-5-(4-octyloxyphenyl)-[1,3,4]oxadiazole (0.95 g, 18% yield)

$^1$H-NMR 400 MHz (CDCl$_3$) δ 8.22 (t, 1H, J=1.43 Hz), 8.20 (t, J=1.76 Hz, 1H), 8.07 (d, J=8.9 Hz, 2H), 7.82 (t, J=1.65 Hz, 1H), 7.56 (m, 2H), 7.36 (m, 3H), 7.01 (d, J=8.9 Hz, 2H), 4.03 (t, J=6.59 Hz, 2H, CH$_2$—O), 1.96 (quin, J=8.02 Hz, 2H), 1.52–1.28 (m, 10H), 0.89 (t, J=7.14 Hz, 3H).

Example 7

Synthesis of (9,9-Dioctyl-9H-fluoren-2-ylethynyl)-trimethylsilane

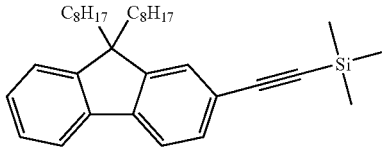

To an ice-cold mixture of 2-bromo-9,9-dioctylfluorene (11.47 g, 24.4 mmol) in 100 mL Et$_3$N was added copper (I) iodide (31.0 mg, 0.163 mmol), palladium (II) acetate (29.7 mg, 0.132 mmol) and triphenylphosphine (90.8 mg, 0.346 mmol). Trimethylsilyl acetylene (3.0 g, 30.5 mmol) was then added and the mixture stirred for 30 minutes followed by a further 30 minutes while warming to room temperature. The reaction mixture was next refluxed for 20 hours and then allowed to cool to room temperature. Thin layer chromatography (hexane as the mobile phase) showed the reaction to be complete and the formation of a reaction product with Rf value less than that of 2-bromo-9,9-dioctylfluorene. Petroleum ether was added to the reaction mixture and the insolubles filtered off. The filtrate was evaporated to dryness and the residual oil taken up in petroleum ether and washed successively with HCl (10%), NaHCO$_3$ solution and water. Drying over magnesium sulfate and evaporation gave oil characterized as (9,9-Dioctyl-9H-fluoren-2-ylethynyl)-trimethylsilane (10.2 g, 86% yield).

Example 8

Synthesis of 2-Ethynyl-9,9-dioctyl-9H-fluorene

To a solution of (9,9-dioctyl-9H-fluoren-2-ylethynyl)-trimethylsilane (10.3 g, 21.2 mmol) in ethanol was added potassium carbonate (2.92 g, 21.2 mmol). The mixture was stirred at room temperature for 20 hours and then filtered. The filtrate was evaporated to dryness and the residue taken up in hexane. Washing with water, drying over magnesium sulfate and evaporation gave an oil characterized as 2-ethynyl-9,9-dioctyl-9H-fluorene (7.20 g, 82% yield).

Example 9

Synthesis of 2-[3-(9,9-Dioctyl-9H-fluoren-2-ylethynyl)-5-phenylethynyl-phenyl]-5-(4-octyloxy-phenyl)-[1,3,4]oxadiazole

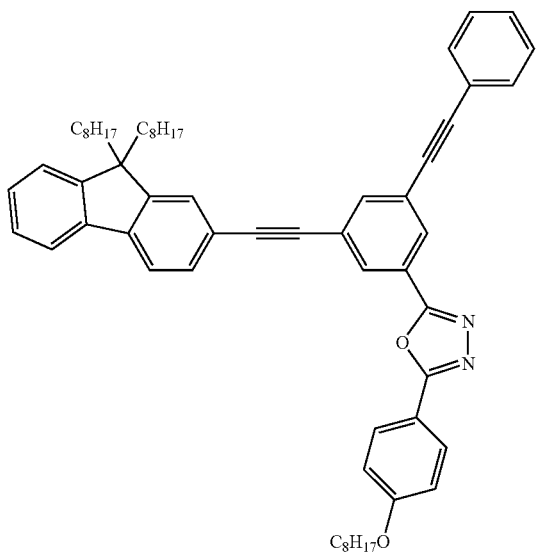

According to the general procedure of Example 1, the reaction of 2-ethynyl-9,9-dioctyl-9H-fluorene (Example 8) with a molar equivalent of 2-(3-bromo-5-phenylethynylphenyl)-5-(4-octyloxy-phenyl)-[1,3,4]oxadiazole (Example 6) gives 2-[3-(9,9-dioctyl-9H-fluoren-2-ylethynyl)-5-phenylethynyl-phenyl]-5-(4-octyloxy-phenyl)-[1,3,4]oxadiazole.

Example 10

Synthesis of 2-(3,5-Bis-trimethylsilanylethynylphenyl)-5-(4-octyloxyphenyl)-[1,3,4]oxadiazole

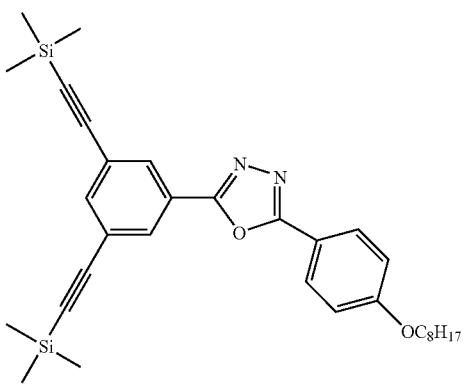

To an ice-cold mixture of 2-(3,5-dibromophenyl)-5-[4-(octyloxy)phenyl]-1,3,4-oxadiazole (11.47 g, 24.4 mmol), triphenylphosphine (0.1816 g, 0.692 mmol), copper (I) iodide (0.062 g, 0.326 mmol) and palladium (II) acetate (0.0594 g, 0.265 mmol) in 100 mL Et$_3$N was added trimethylsilyl acetylene (6.0 g, 61.1 mmol). The mixture was stirred in the ice bath for 30 minutes. The ice bath was removed and after a further 30 minutes warming to room temperature the mixture was heated at reflux for 20 hours. The cooled reaction mixture was slurried in 150 mL methanol. The insoluble material was filtered off and dissolved in chloroform. Precipitation with hexane and evaporation to dryness of the hexane solution gave 2-(3,5-bis-trimethylsilanylethynylphenyl)-5-(4-octyloxyphenyl)-[1,3,4]oxadiazole (1.5 g, 11% yield). The methanol soluble filtrate was evaporated to dryness and dissolved in 250 mL chloroform. About 1.5 L of hexane was added. Filtration gave a dark solid material (3.5 g). Evaporation to dryness of the filtrate gave a further crop of 2-(3,5-bis-trimethylsilanylethynyl-phenyl)-5-(4-octyloxyphenyl)-[1,3,4]oxadiazole (3.5 g, 34% yield in total).

Example 11

Synthesis of 2-(3,5-Bis-ethynylphenyl)-5-(4-octyloxyphenyl)-[1,3,4]oxadiazole

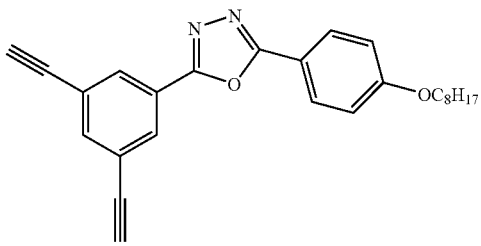

A mixture of 2-(3,5-bis-trimethylsilanylethynylphenyl)-5-(4-octyloxyphenyl)-[1,3,4]oxadiazole (1.20 g, 2.21 mmol) and potassium carbonate (0.305 g, 2.21 mmol) in methanol (30 mL) was stirred at room temperature for 20 hours. Filtration of the solid, washing with water and drying gave 2-(3,5-bis-ethynyl-phenyl)-5-(4-octyloxyphenyl)-[1,3,4] oxadiazole. (0.75 g, 80% yield).

¹H-NMR (400 MHz, CDCl₃) δ 8.20–8.19 (2H, d, J=1.43 Hz), 8.06–8.04 (2H, d, J=8.70 Hz), 7.73 (1H, t, J=1.30 Hz), 7.02–7.00 (2H, d, J=8.79 Hz), 4.04–4.01 (2H, t, CH₂O, J=6.59 Hz), 3.18 (2H, s, ethynyl CH's), 1.85–1.78 (2H, quin, J=6.7 Hz), 1.52–1.24 (10H, m), 0.90–0.87 (3H, t, CH₃).

Example 12

Synthesis of 2-Bromo-9-fluorenone

To a mechanically stirring solution of 2-bromfluoren-9-one (150 g, 0.612 mol) in 1100 mL pyridine was added 18 mL of a 1M solution of tetrabutyl ammonium hydroxide in methanol. The solution immediately turned red-brown. The solution was stirring vigorously for 18 hours. During the course of the reaction a precipitate was observed. To the reaction product was added 35 mL of water and after stirring for an additional 5 minutes the contents of the flask was filtered. The yellow solid obtained was re-crystallized from hot ethanol to give 2-Bromo-9-fluorenone as shiny yellow needles (98 g, 62% yield).

¹³C-NMR (CDl₃) δ 192.35, 143.64, 142.97, 137.06, 135.73, 435.00, 133.67, 129.40, 127.53, 124.58, 122.89, 121.69, 120.41

Example 13

Synthesis of 2-Bromo-9-(2-biphenyl)-9-fluorenone

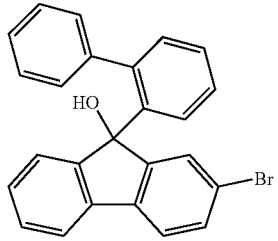

This compound was made according to the procedure given by Pei and co-workers (Pei et al., *J. Org. Chem.*, 67, 4924–4936 (2002)) with a 74% yield.

¹H-NMR (400 MHz) δ 8.34–8.42 (1H, dd, J=0.88, 8.01 Hz), 7.55–7.51 (1H, td, J=1.46, 8.01 Hz), 7.35–7.28 (3H, m), 7.21–7.18 (3H, m), 7.14–7.12 (1H, m), 7.00–6.98 (1H, d, J=8.01 Hz), 6.93–6.90 (1H, dd, J=1.37–7.52 Hz), 6.84–6.80 (1H, tt, J=7.52, 1.27 Hz), 6.70–6.66 (1H, br t, J=approx 7.3 Hz), 6.60–6.57 (1H, br t, J=7.7 Hz), 6.14–6.12 (1H, br d, J=7.72 Hz), 5.78=5.94 (1H, br d, J=7.82 Hz), 2.24 (1H, br s, OH).

Example 14

Synthesis of 2-Bromo-9,9-spirobifluorene

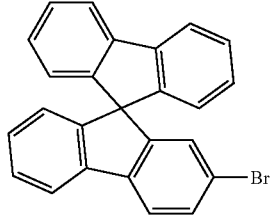

To a refluxing solution of 2-bromo-9-(2-biphenyl)-9-fluorenone (3.0 g, 7.26 mg) in 50 mL acetic acid was added a few drops of concentrated hydrochloric acid. Refluxing was continued for 30 minutes. The cooled mixture was poured into 200 mL water and the obtained solid filtered, dried and recrystallized from chloroform/ethanol to give 2-bromo-9,9-spirobifluorene (2.26 g, 79% yield).

¹H-NMR (400 MHz, CDCl₃) δ 7.85–7.83 (2H, d, J=8.10 Hz), 7.82–7.80 91H, d, J=7.62 Hz), 7.71–7.69 (1H, d, J=8.10 Hz), 7.49–7.47 (1H, dd, J=1.86, 8.1 Hz), 7.40–7.34 (3H, m), 7.14–7.10 (3H, t, J=7.42, 7.61 Hz), 6.84 (1H, d, J=1.37 Hz), 6.73–6.70 (3H, m).

Example 15

Synthesis of 2-[3,5-Bis-(9,9-spirofluoren-2-ylethvnyl)phenyl]-5-(4-octyloxyphenyl)[1,3,4] oxadiazole

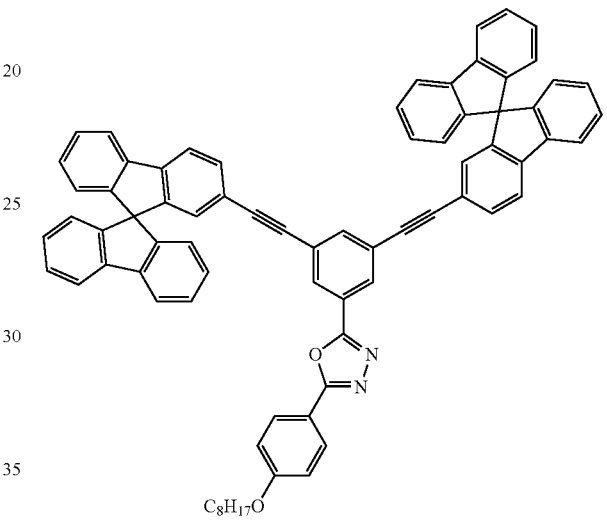

By the general procedure of Example 1, the reaction of 2-(3,5-bis-ethynylphenyl)-5-(4-octyloxyphenyl)-[1,3,4] oxadiazole (Example 11) with a two molar equivalent of 2-bromo-9,9-spirobifluorene (Example 14) gives the required 2-[3,5-bis-(9,9-spirofluoren-2-ylethynyl)phenyl]-5-(4-octyloxyphenyl)-[1,3,4]oxadiazole.

Example 16

Screening of Compounds in MDP Formulations

This example describes electroluminescence performance of bi-layer molecularly doped polymer (MDP) OLED systems having hole-transport material MTDATA, emissive dopant (2-Benzothienylpyridinato) iridium(III) acetylacetonate (BTPIr) complex and various electron transport agents. The electron transport agents are as follows: Comparative Example 16 contained PBD, Example 16-A contained the material prepared in Example 3, Example 16-B contained the material prepared in Example 2, and Example 16-C contained the material prepared in Example 5.

ITO-glass substrates (Applied Films Corporation, CO; ca. 25 Ω/sq.) were rinsed in acetone (Aldrich Chemical Company), dried with nitrogen, and rubbed with TX1010 Vectra Sealed-Border Wipers (Texwipe, N.J.) soaked in methanol (Aldrich Chemical Company, Milwaukee, Wis.), after which they were subjected to oxygen plasma treatment at 200 mT base oxygen pressure and output power of 50 W in Technics Micro Reactive Ion Etcher, Series 80 (K&M Company, CA). A hole injecting layer was formed by spin coating PEDT 4083 (Bayer Corp., later denoted as PEDT) from its water suspension at 2500 RPM spin speed after filtering the suspension through 0.2 μm Nylon microfilters, followed by annealing under nitrogen gas flow at 110° C. for ca. 15 min.

To a vial containing 0.010 g of PBD (Dojindo Co.) was added 1.7 mL of a Stock solution B containing 0.075 g PVK (Polymer Source Inc), 0.050 g MTDATA and 0.0125 g BTPIr in 8.5 mL chloroform. The final concentration of solids was approximately in 0.010 g PBD, 0.015 g PVK, 0.0025 g BTPIr and 0.010 g MTDATA. The solution was spun-coated in triplicate onto glass-ITO/PEDT substrates at the spin speed of 2500 RPM after filtration through 0.2 μm Nylon microfilters.

A layer of electron transport material Alq (HWSands Corp.) was deposited under vacuum (ca. $10^{-5}$ torr) with sublimation rates 0.5–2 Å/s. All OLEDs were capped with a cathode composed of ca. 7–10 Å of lithium fluoride (LiF, Alfa Aesar Co.) and 2000 Å of aluminum (Al, Alfa Aesar Co.), deposited at rates of 0.5 Å for LiF, and 15–20 Å for Al under high vacuum ($10^{-6-10-5}$ torr).

OLED electroluminescence spectral measurements and luminance-current-voltage tests conducted on the device using a current density sweep range of 0–20 mA/cm² gave the following results.

TABLE 2

Preparation conditions for Examples 16A–C and Comparative Example 16

| Ex. | Stock Solution B (mL) | MTDATA (mg) | BTPIr (mg) | ETM | PVK (mg) | MTDATA:BTPIr: ETM:PVK |
|---|---|---|---|---|---|---|
| Comp. 16 | 1.7 | 10 | 2.5 | 10 mg PBD | 15 | 27:7:27:40 |
| 16-A | 1.7 | 10 | 2.5 | 10 mg Ex. 3 | 15 | 27:7:27:40 |
| 16-B | 1.7 | 10 | 2.5 | 10 mg Ex. 2 | 15 | 27:7:27:40 |
| 16-C | 1.7 | 10 | 2.5 | 10 mg Ex. 5 | 15 | 27:7:27:40 |

TABLE 3

Performance characteristics of lamps

| Ex. | CIE x,y coordinates | Voltage, V | QE, % | Brightness Dd/m2 | Eff., lm/W |
|---|---|---|---|---|---|
| Comp. 16 | 0.671, 0.327 | 13.8 | 1.18 | 205.0 | 0.234 |
| 16-A | 0.561, 0.43 | 12.2 | 0.032 | 12.1 | 0.0156 |
| 16-B | 0.679, 0.321 | 14 | 2.5 | 329.0 | 0.369 |
| 16-C | 0.681, 0.319 | 13.4 | 0.88 | 139.0 | 0.162 |

Experiment 17

Device Performance

A stock solution C was made up of 40 mg MTDATA and 8.5 mg BTPIr in 7 mL chloroform. A quantity of 1.7 mL was added to a vial containing 10 mg 2-(3,5-bis-phenylethynylphenyl)-5-(4-octyloxyphenyl)-[1,3,4] oxadiazole from Example 2 and 15 mg PVK. The approximate content of the vial is recorded in the following table as Example 17.1. The solution was spun-coated onto glass-ITO/PEDT substrates at the spin speed of 2500 RPM after filtration through 0.2 μm Nylon microfilters.

A layer of electron transport material Alq (HWSands Corp) was deposited under vacuum (ca. $10^{-5}$ torr) with sublimation rates 0.5–2 Å/s. All OLEDs were capped with a cathode composed of ca. 7–10 Å of lithium fluoride (LiF, Alfa Aesar Co.) and 2000 Å of aluminum (Al, Alfa Aesar Co.), deposited at rates of 0.5 Å for LiF, and 15–20 Å for Al under high vacuum ($10^{-6-10-5}$ torr). The lamps that were evaluated in this experiment are shown in Table 4.

TABLE 4

Preparation conditions for Experiments 17A–C and Comparative Example 17

| Ex. | Stock Solution C | ET | PVK | MTDATA:BTPIr:ETM:PVK |
|---|---|---|---|---|
| 17-A | 1.7 mL | 10 mg Ex 2 | 15 mg | 27:6:27:40 |
| 17-B | 1.7 mL | 13 mg Ex 2 | 15 mg | 27:6:32:37 |
| 17-C | 1.7 mL | 17 mg Ex 2 | 15 mg | 27:6:22:46 |
| Comp. 17 | 1.7 mL | 10 mg PBD | 15 mg | 27:6:27:40 |

Device performance data is summarized in Table 5. All tested devices exhibit deep red electroluminescence (CIE x,y 0.68, 0.32) with no electroluminescence contribution from MTDATA:ETM exciplex emission even at higher concentrations of the ETM component (Examples 17-B and 17-C). This indicates that efficient red electroluminescence can be achieved without admixture of exciplex emission if a combination of MTDATA (HTM) and 2-(3,5-bis-phenylethynylphenyl)-5-(4-octyloxyphenyl)-[1,3,4] oxadiazole (ETM) is used. Devices with higher concentration of MTDATA are expected to show improved stability characteristics, whereas exciplex formation between MTDATA and PBD at higher concentrations of MTDATA prevents from obtaining efficient and pure emission with the control compositions (e.g. based on PVK:MTDATA:PBD:BTPIr). This suggests that by using 2-(3,5-bis-phenylethynylphenyl)-5-(4-octyloxyphenyl)-[1, 3,4]oxadiazoles one can address this problem by introducing an electron deficient component which has lowered exciplex formation efficiency with MTDATA, thereby allowing for the higher concentration of MTDATA and possibly longer device operation lifetimes.

Figure 6:
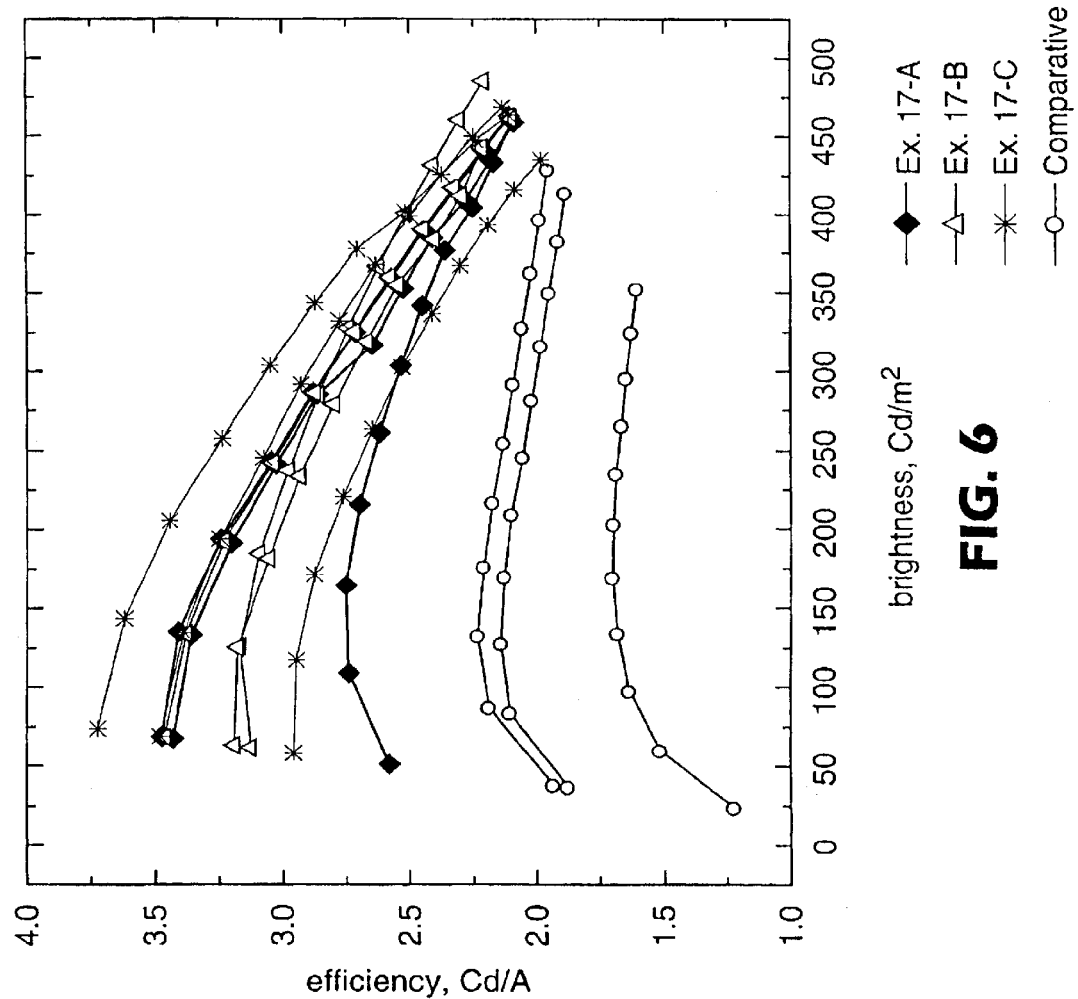
FIG. 6 is the plot of the brightness characteristics for various OLEDS containing disclosed compounds.

Devices based on 2-(3,5-bis-phenylethynylphenyl)-5-(4-octyloxyphenyl)-[1,3,4]oxadiazole (Ex 17-A to 17-C) showed higher efficiencies than those of a control device (Comp. Ex. 17). Moreover, an increase in concentration of the ETM component resulted in an increase in efficiencies (Table 5 and FIG. 6). FIG. 6 shows efficiency-brightness plots for studied devices. Table 5 and FIG. 6 indicate that at projected commercially required luminance for the red electroluminescence (ca. 200–300 Cd/m²), efficiencies of the studied MDP compositions fall in the 2.5–3.5Cd/A range, which is comparable with the best previously achieved MDP OLED results.

TABLE 5

Performance characteristics of lamps at a brightness of 200 Cd/m²

| Ex. | CIE x,y coordinates | QE, % | Eff, Cd/A | Eff., lm/W | Voltage, V |
|---|---|---|---|---|---|
| 17-A | 0.68, 0.32 | 3.3 | 2.7 | 0.78 | 10.5 |
| 17-B | 0.68, 0.32 | 3.7 | 3.0 | 0.93 | 10.4 |
| 17-C | 0.68, 0.32 | 4.0 | 3.4 | 1.2 | 9.4 |
| Comp. 17 | 0.68, 0.32 | 2.4 | 2.1 | 0.53 | 12.5 |

We claim:

1. A compound of formula I

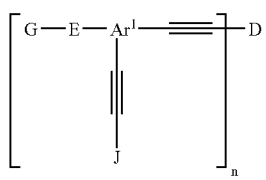

I wherein

D is a monovalent, divalent, trivalent, or tetravalent radical of a $C_{3-30}$ alkane, $C_{3-30}$ heteroalkane, conjugated or unconjugated $C_{6-60}$ carbocyclic aromatic compound, $C_{3-60}$ heteroaromatic compound, $C_{18-60}$ tertiary aromatic amino compound, or a compound or Formula II or Formula III

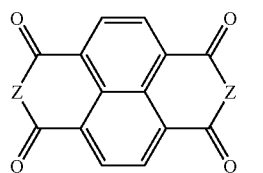

II

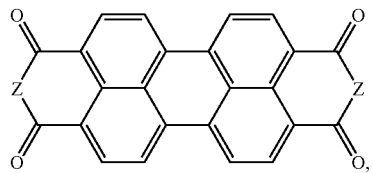

III wherein D is unsubstituted or substituted with one or more alkyl, alkenyl, alkoxy, aryl, aryloxy, fluoro, fluoroalkyl, perfluoroalkyl, heteroalkyl, heteroaryl, or combinations thereof, wherein $Ar^1$ is trivalent radical of a conjugated $C_{6-30}$ carbocyclic aromatic compound that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

E is a $C_{3-60}$ heteroarylene having at least one —C=N— unit, said heteroarylene being unsubstituted or substituted with one or more alkyl, alkenyl, alkoxy, aryl, aryloxy, fluoro, fluoroalkyl, perfluoroalkyl, heteroalkyl, heteroaryl, or combinations thereof;

G is a monovalent radical selected from hydrogen, $C_{1-30}$ alkyl, $C_{1-30}$ heteroalkyl, $C_{3-60}$ heteroaryl, $C_{6-60}$ aryl, or $C_{18-60}$ tertiary aromatic amino aryl wherein G is unsubstituted or substituted with one or more alkyl, alkenyl, alkoxy, aryl, aryloxy, fluoro, fluorualkyl, perfluoroalkyl, heteroalkyl, heteroaryl, or combinations thereof;

J is a monovalent radical selected from $C_{1-30}$ alkyl, $C_{1-30}$ heteroalkyl, $C_{6-60}$ aryl, or $C_{18-60}$ tertiary aromatic amino aryl wherein J is unsubstituted or substituted with one or more alkyl, alkenyl, alkoxy, aryl, aryloxy, fluoro, fluoroalkyl, perfluoroalkyl, heteroalkyl, or combinations thereof;

Z is NH or $CH_2$ and n is an integer of 1 to 4, wherein no more than one of D and J is an unsubstituted phenyl when n is equal to 1.

2. The compound of claim 1, wherein D comprises a radical of a $C_{6-60}$ aromatic compound selected from

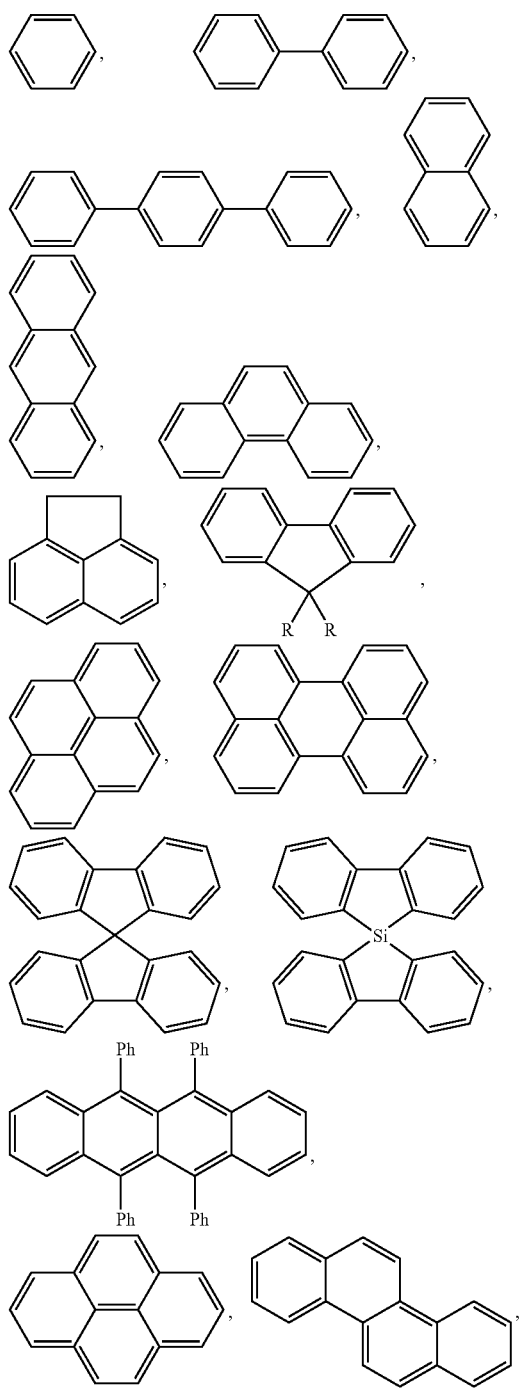

-continued

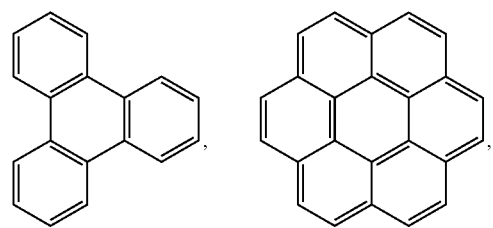

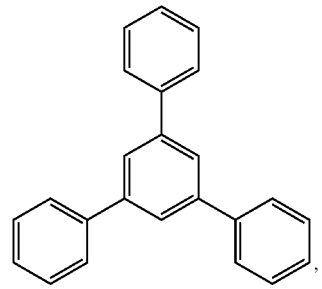

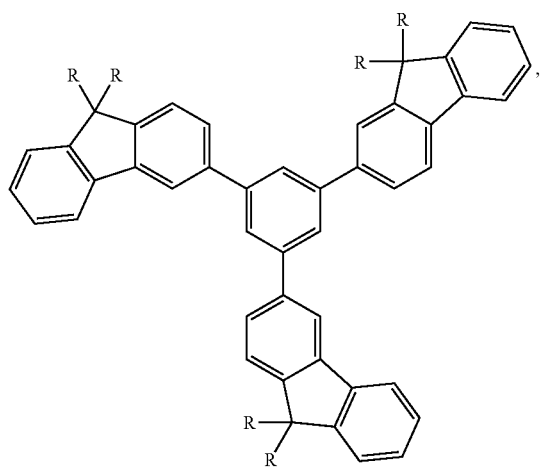

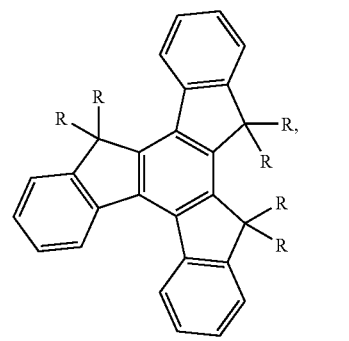

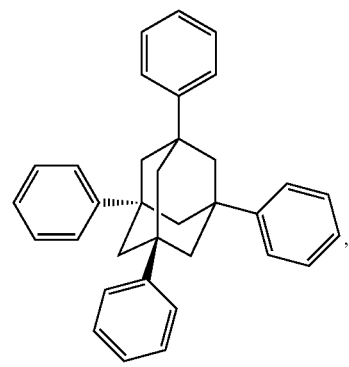

-continued

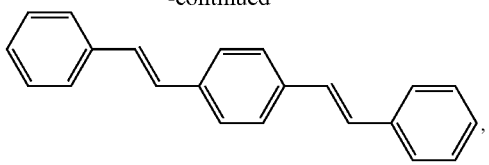

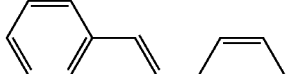

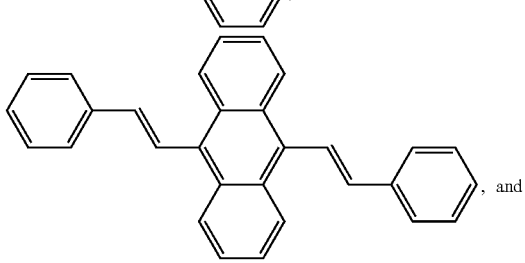, and

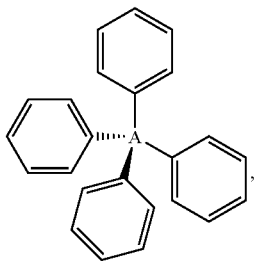

wherein D is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof, wherein
  each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof; and
  A is C, Si, Ge, Pb, or Sn.

3. The compound of claim 1, wherein D comprises a radical of a $C_{3-60}$ heteroaromatic compound having at least one —C=N— unit, said $C_{3-60}$ heteroaromatic compound selected from

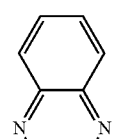

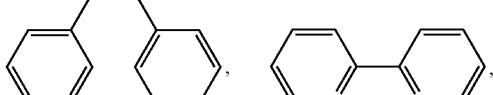

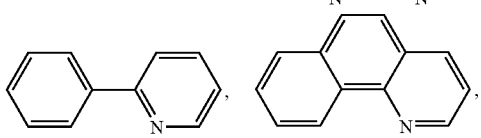

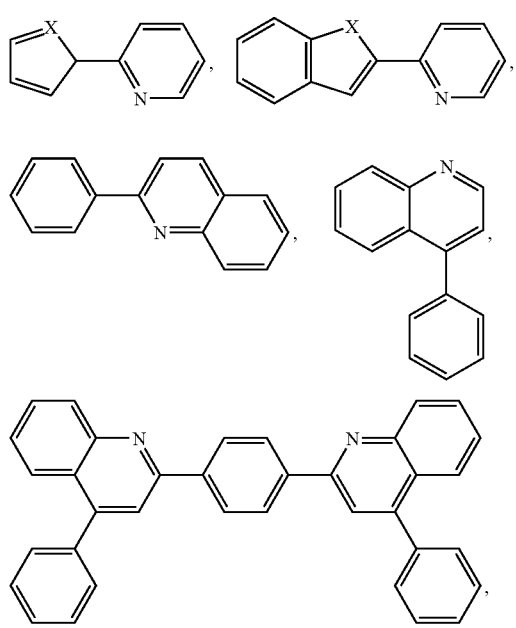

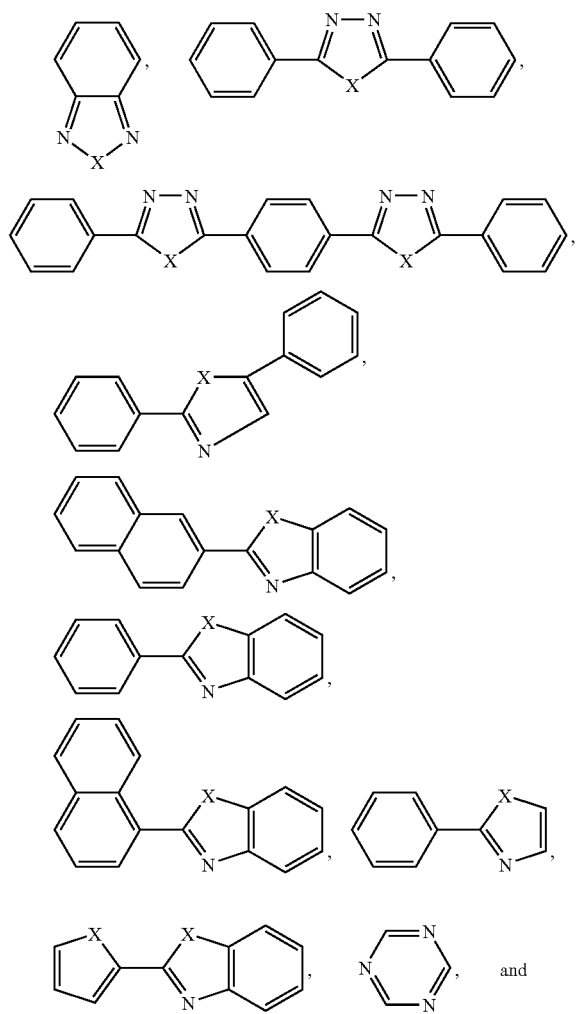

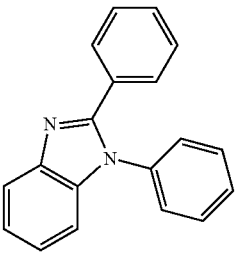

wherein D is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof, wherein X is O, S, or $NR^2$ where $R^2$ is a $C_{1-30}$ alkyl, a $C_{1-30}$ heteroalkyl, a $C_{6-20}$ aryl, a $C_{3-20}$ heteroaryl, or a combination thereof.

4. The compound of claim 1, wherein D comprises a radical of a $C_{3-60}$ heteroaromatic compound that is electron rich or of a $C_{18-60}$ tertiary aromatic amino compound selected from

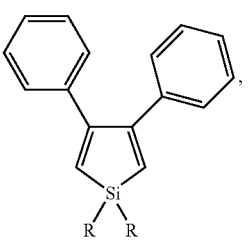

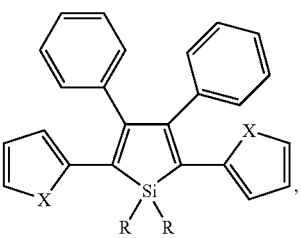

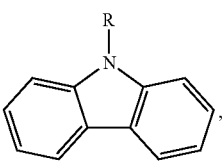

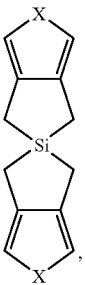

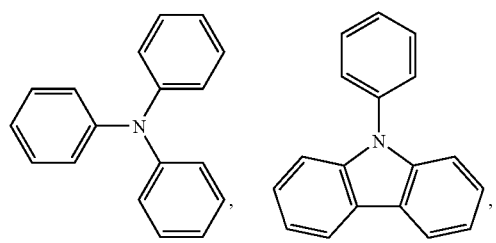

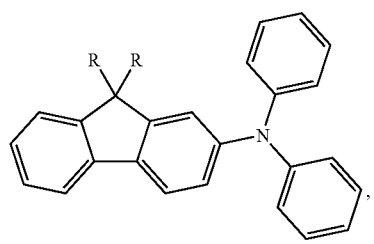

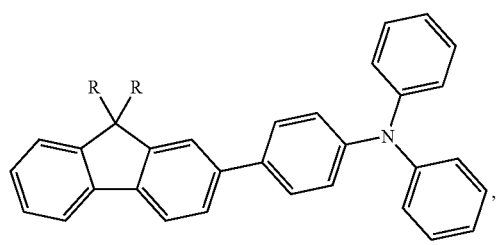

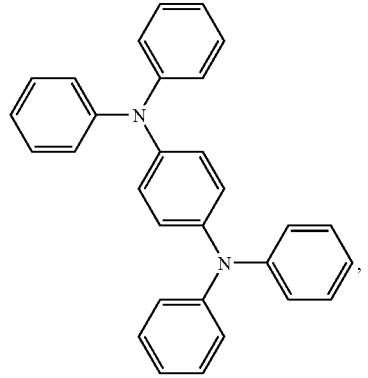

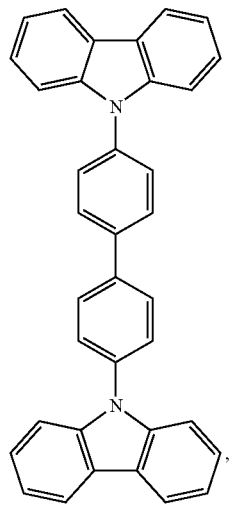

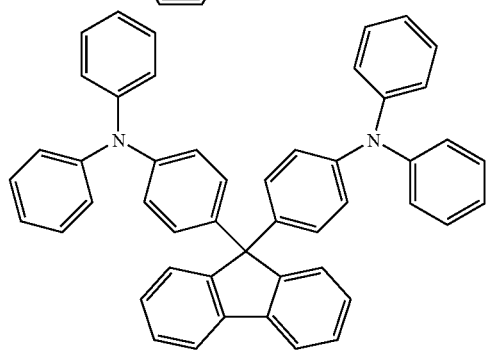

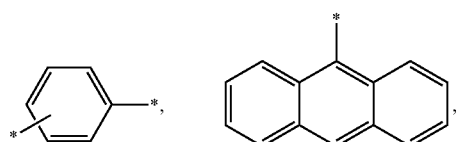

wherein D is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof, wherein each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof; and X is O, S, or $NR^2$ where $R^2$ is a $C_{1-30}$ alkyl, a $C_{1-30}$ heteroalkyl, a $C_{6-20}$ aryl, a $C_{3-20}$ heteroaryl, or a combination thereof, and t is an integer of 1 to 4.

5. The compound of claim 1, wherein n is equal to 2 and D comprises a radical selected from

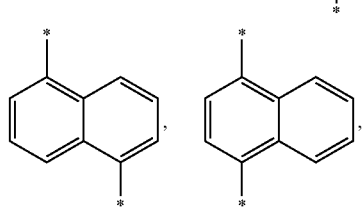

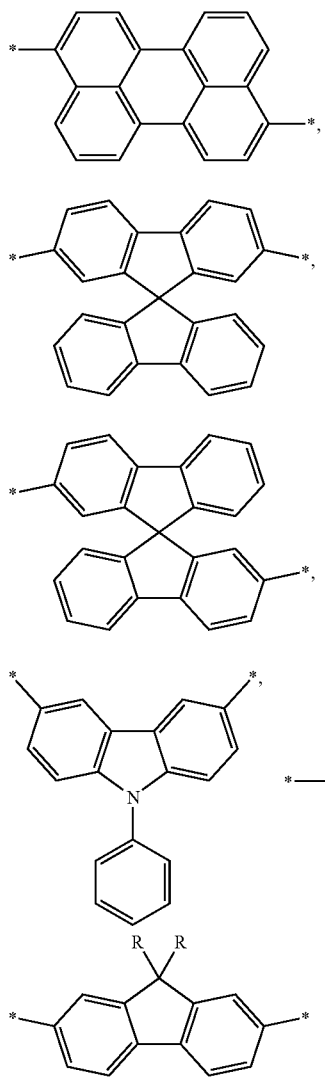

wherein D is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof, wherein each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof.

6. The compound of claim 1, wherein n is equal to 3 and D comprises a radical selected from

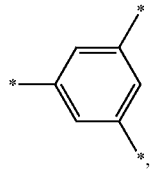

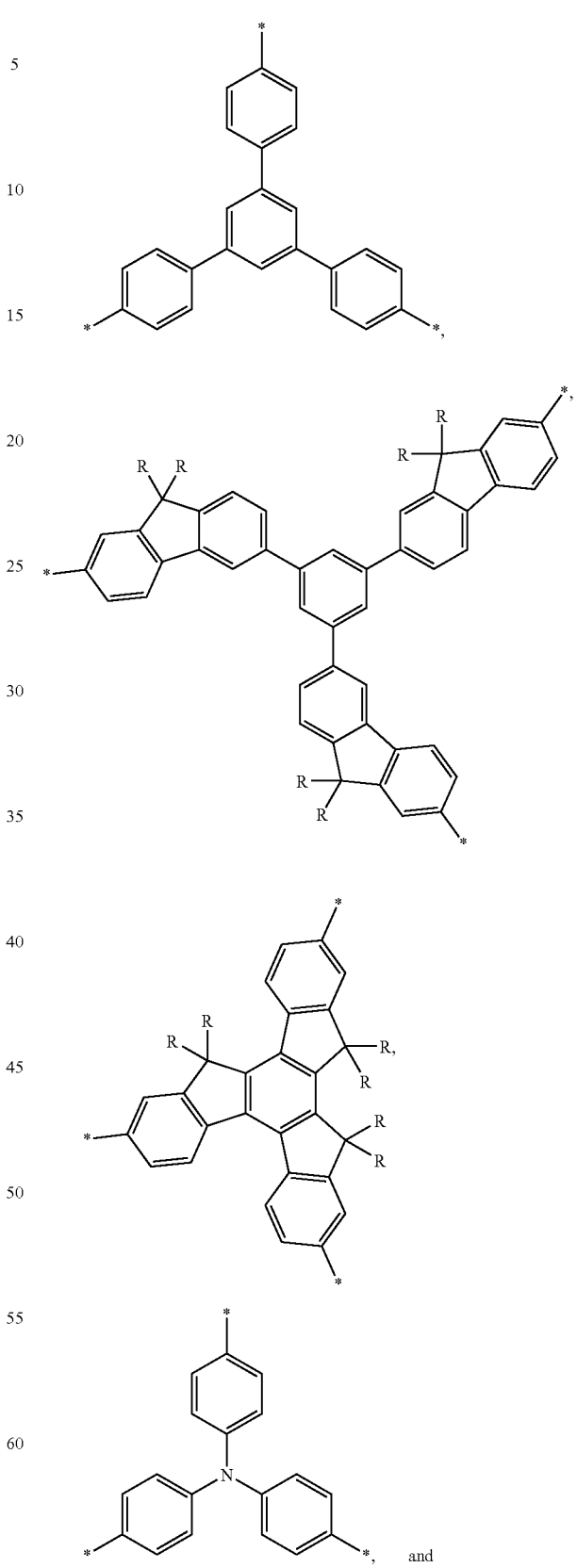

and

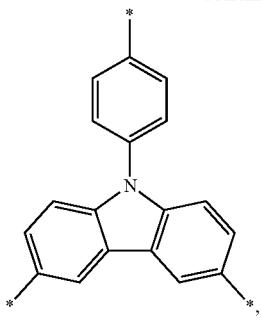

wherein D is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof;

wherein each R is independently a $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof.

7. The compound of claim 1, wherein n is equal to 4 and D comprises a radical selected from

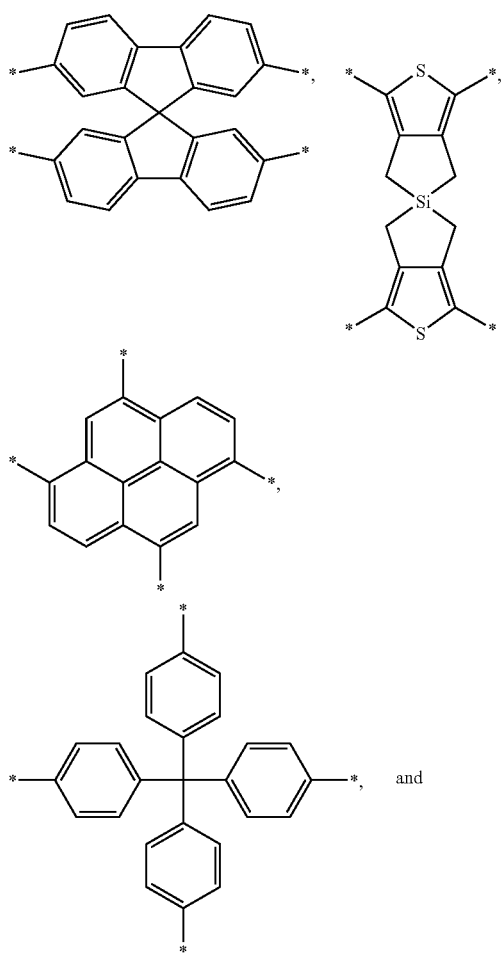

and

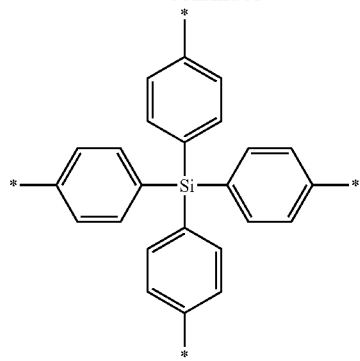

wherein D is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof.

8. The compound of claim 1, wherein $Ar^1$ comprises a trivalent radical of

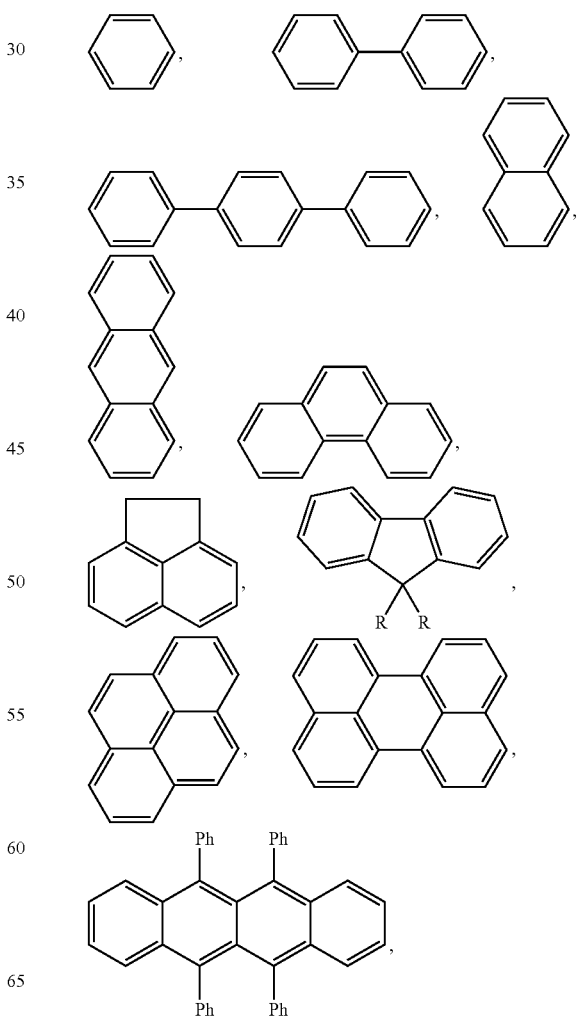

-continued

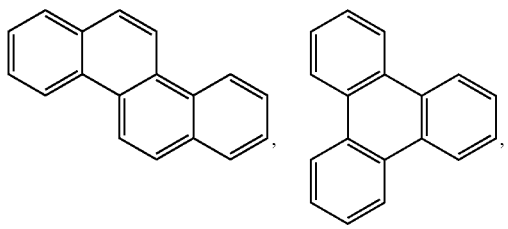

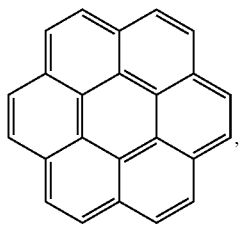

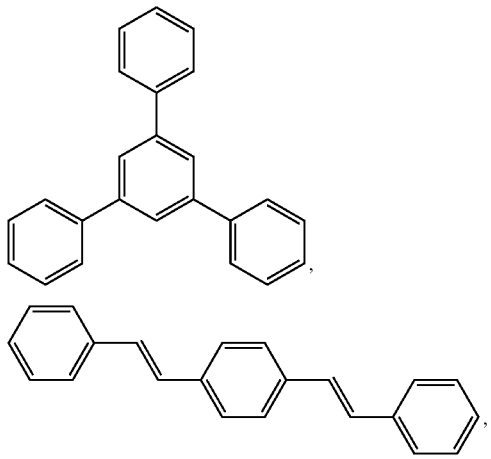

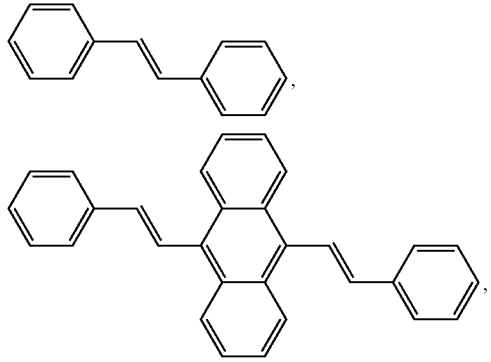

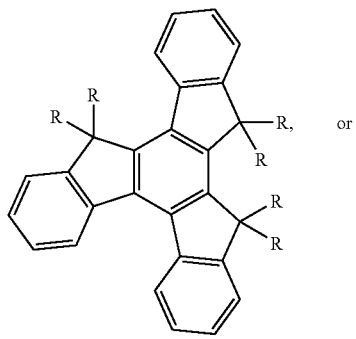

-continued

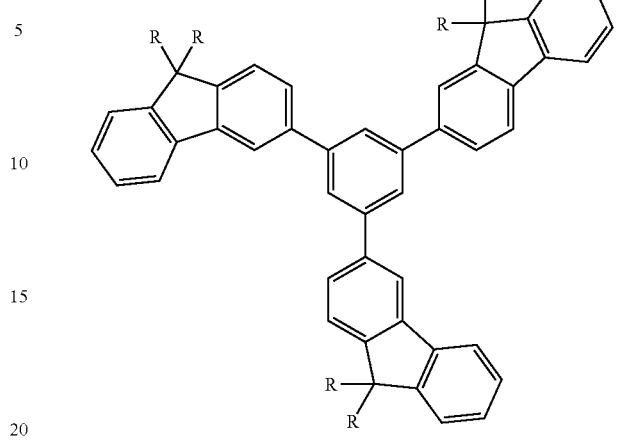

wherein $Ar^1$ is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof, wherein each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof.

9. The compound of claim 1, wherein $Ar^1$ comprises a trivalent radical of benzene.

10. The compound of claim 1, wherein E comprises a radical of oxadiazole, N-substituted triazole, N-substituted imidazole, benzoimidazole, N-substituted pyrazole, oxazole, isoxazole, thiazole, thiadiazole, benzothiadiazole, isothiazole, pyridine, pyridazine, pyrimidine, pyrazine, triazine, tetrazine, benzoxazole, benzothiazole, quinoline, isoquinoline, cinnoline, quinazoline, quinoxaline, phthalazine, benzotriazine, phenazine, phenanthridine, or acridine.

11. The compound of claim 1, wherein E comprises a radical of benzoimidazole, oxadiazole, thiadiazole, or triazole.

12. The compound of claim 1, wherein B comprises a radical of oxadiazole.

13. The compound of claim 1, wherein G comprises a monovalent radical of

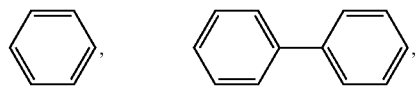

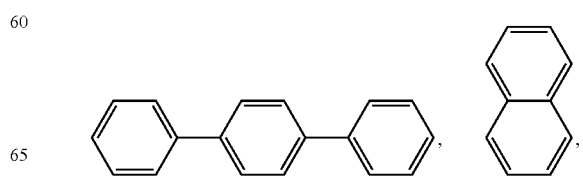

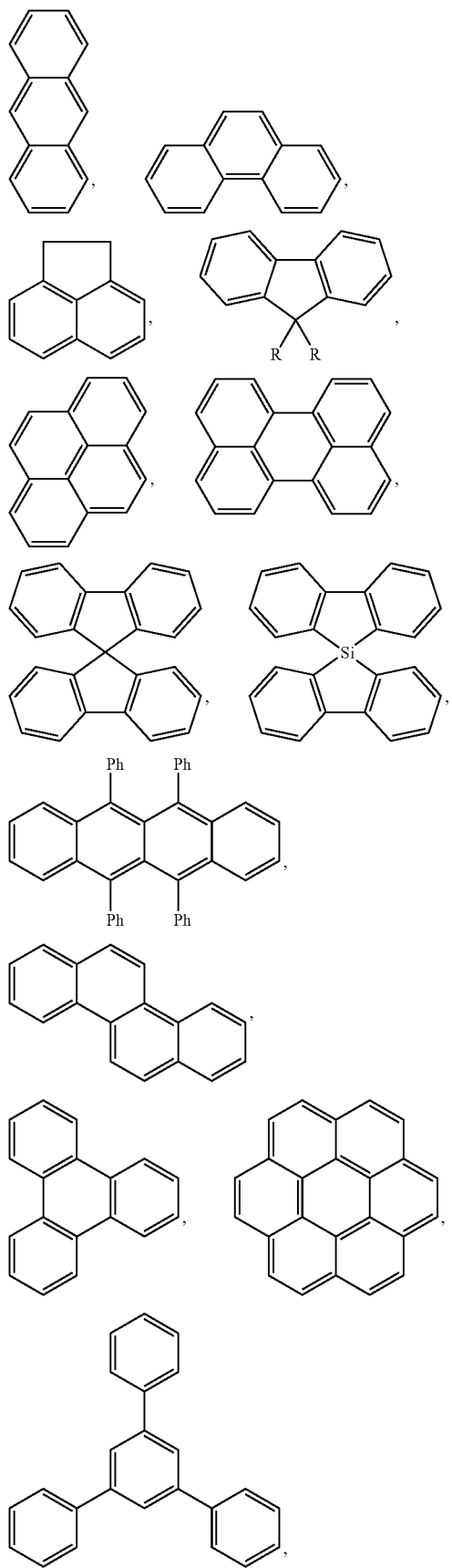
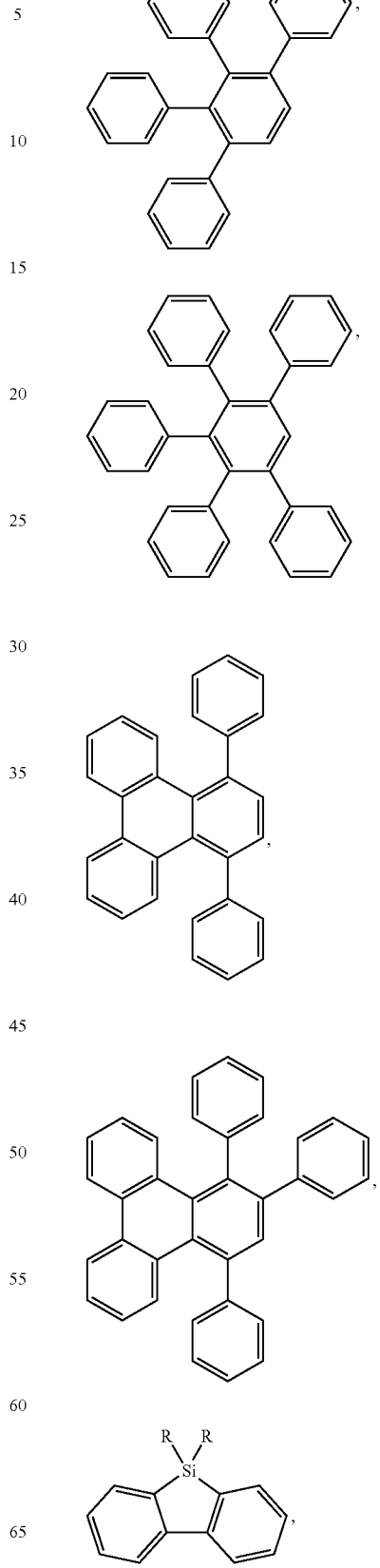

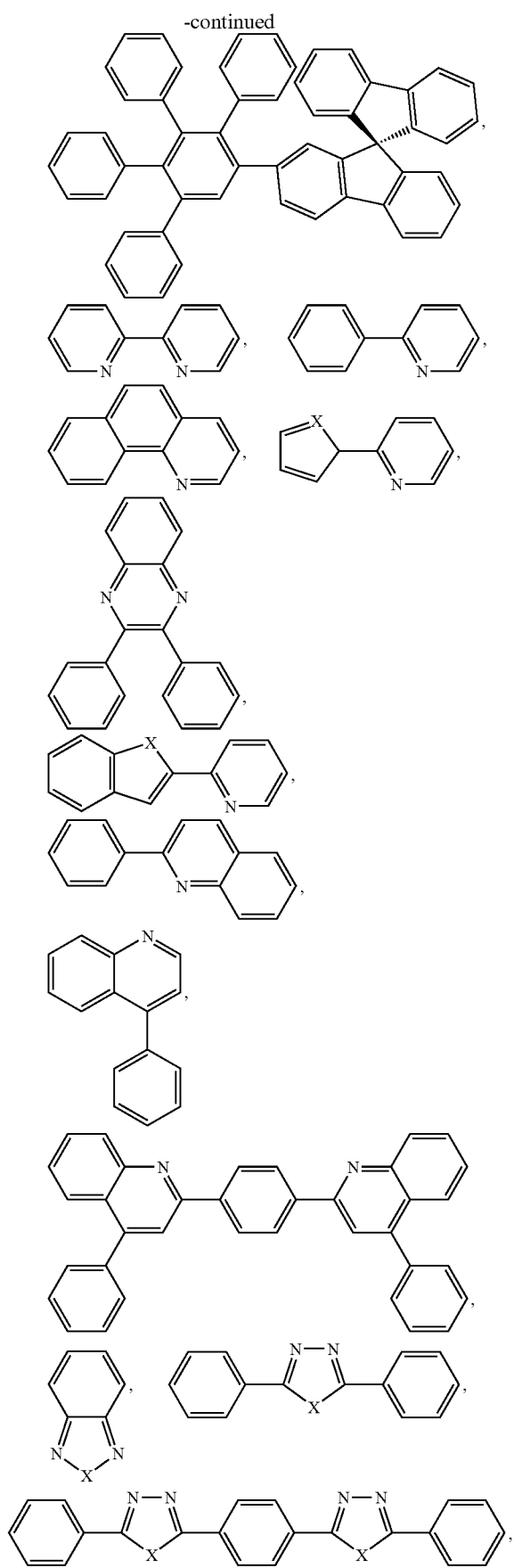
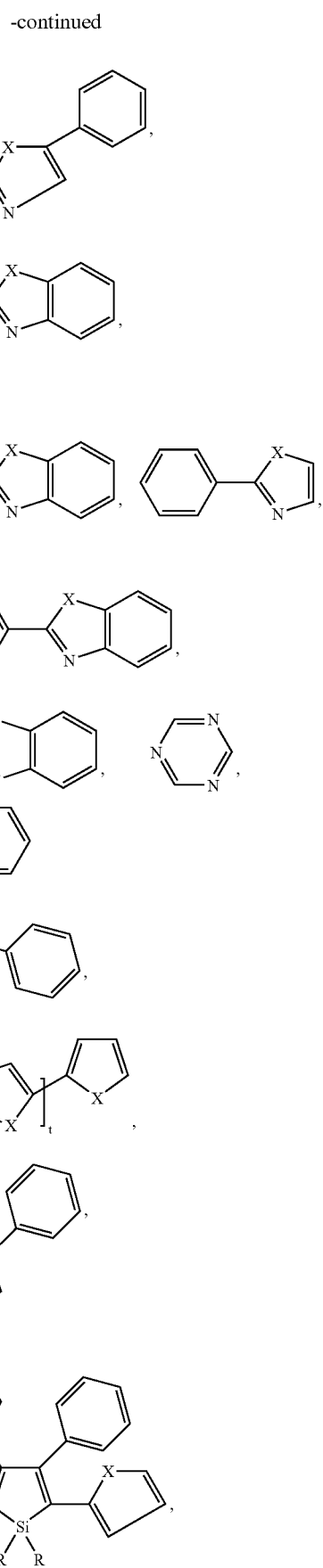

-continued

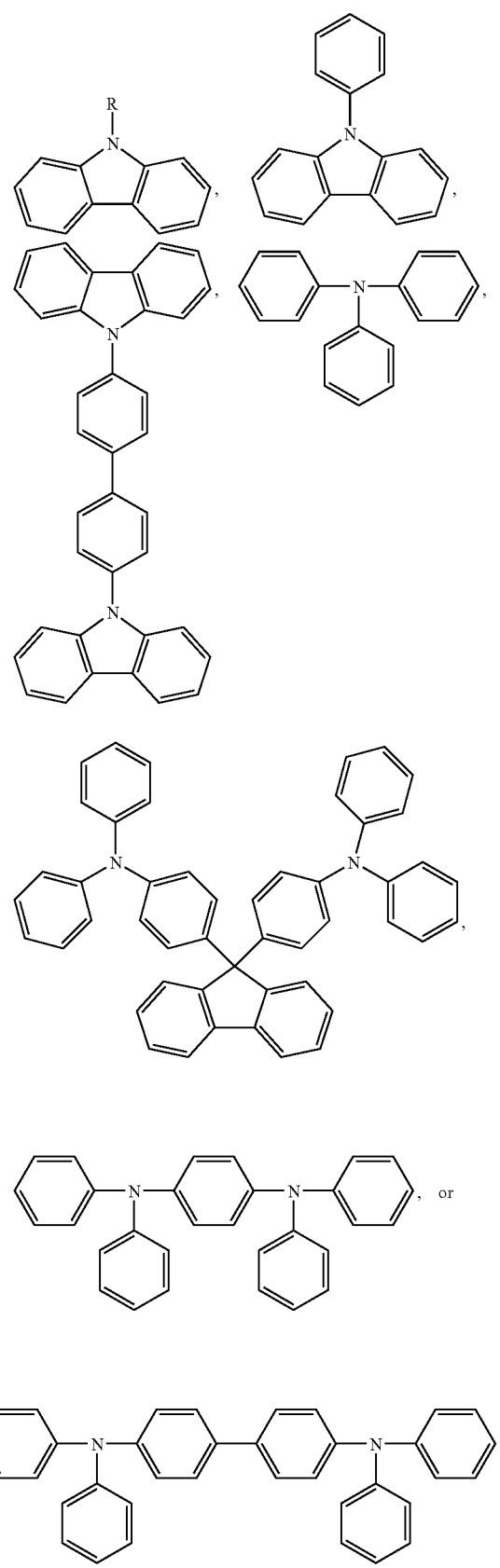

wherein G is unsubstituted or substituted with one or more substituents selected from $C_{1-20}$ alkyl, $C_{2-20}$ alkenyl, $C_{1-20}$ alkoxy, $C_{6-20}$ aryl, $C_{6-20}$ aryloxy, fluoro, $C_{1-20}$ fluoroalkyl, $C_{1-20}$ perfluoroalkyl, $C_{1-20}$ heteroalkyl, $C_{3-20}$ heteroaryl, and combinations thereof, wherein each R is independently an $C_{1-30}$ alkyl, $C_{2-30}$ alkenyl, $C_{1-30}$ alkoxy, $C_{6-30}$ aryl, $C_{6-30}$ aryloxy, fluoro, $C_{1-30}$ fluoroalkyl, $C_{1-30}$ perfluoroalkyl, $C_{1-30}$ heteroalkyl, $C_{3-30}$ heteroaryl, or combinations thereof;

X is O, S, or $NR^2$ where $R^2$ is a $C_{1-30}$ alkyl, a $C_{1-30}$ heteroalkyl, a $C_{6-20}$ aryl, a $C_{3-20}$ heteroaryl, or a combination thereof; and t is an integer of 0 to 4.

14. The compound of claim 1, wherein the compound is

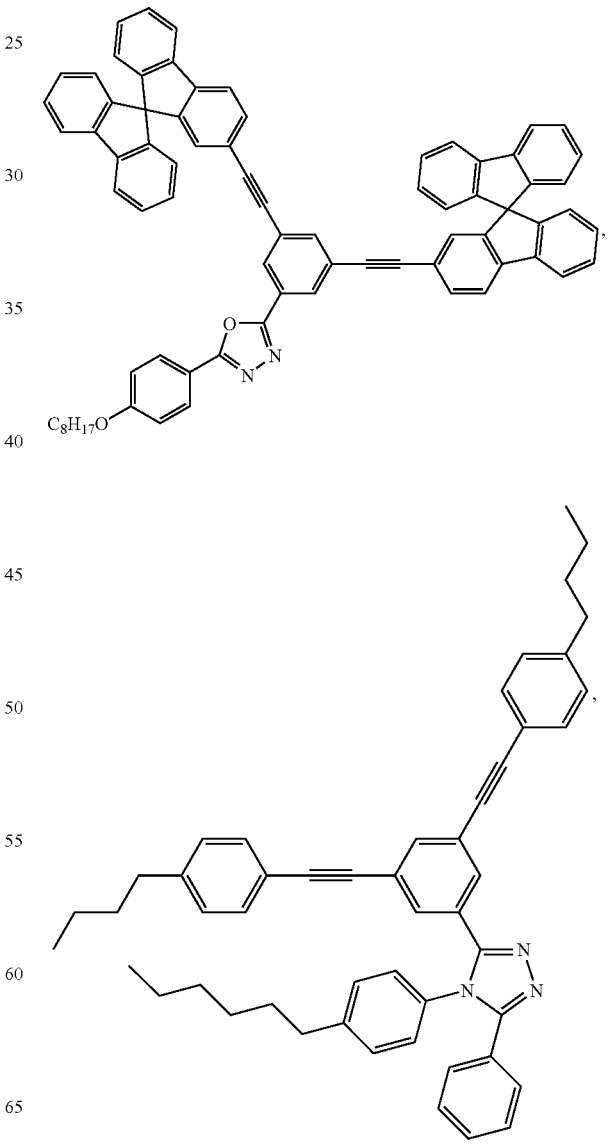

111
-continued
112
-continued
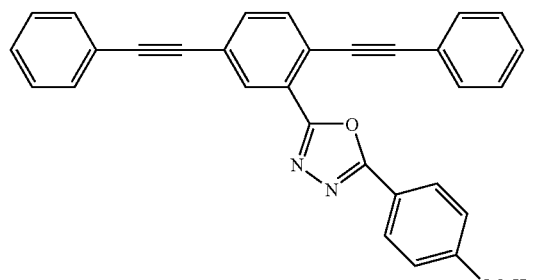
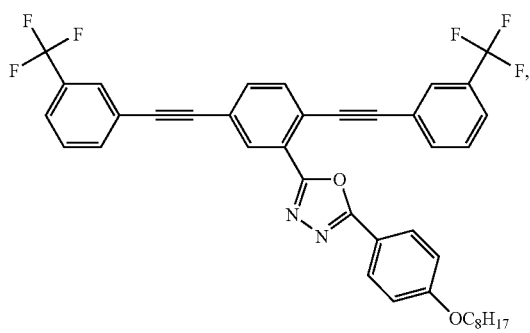
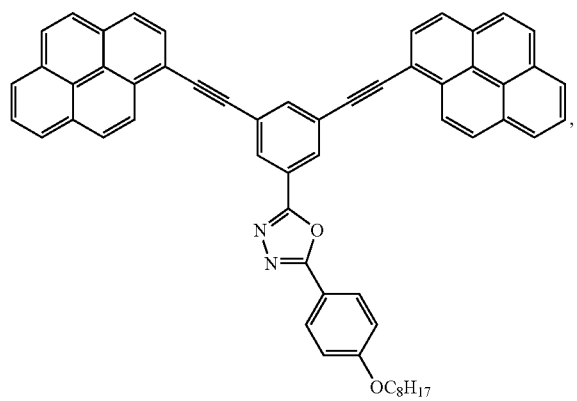
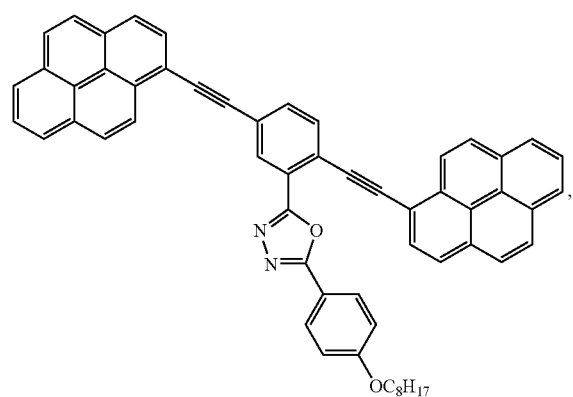
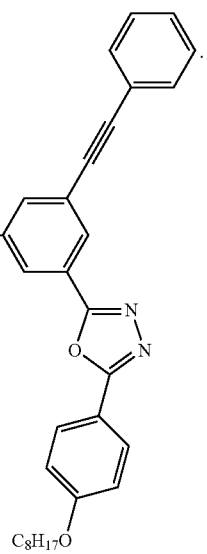

15. The compound of claim 1, wherein the compound is
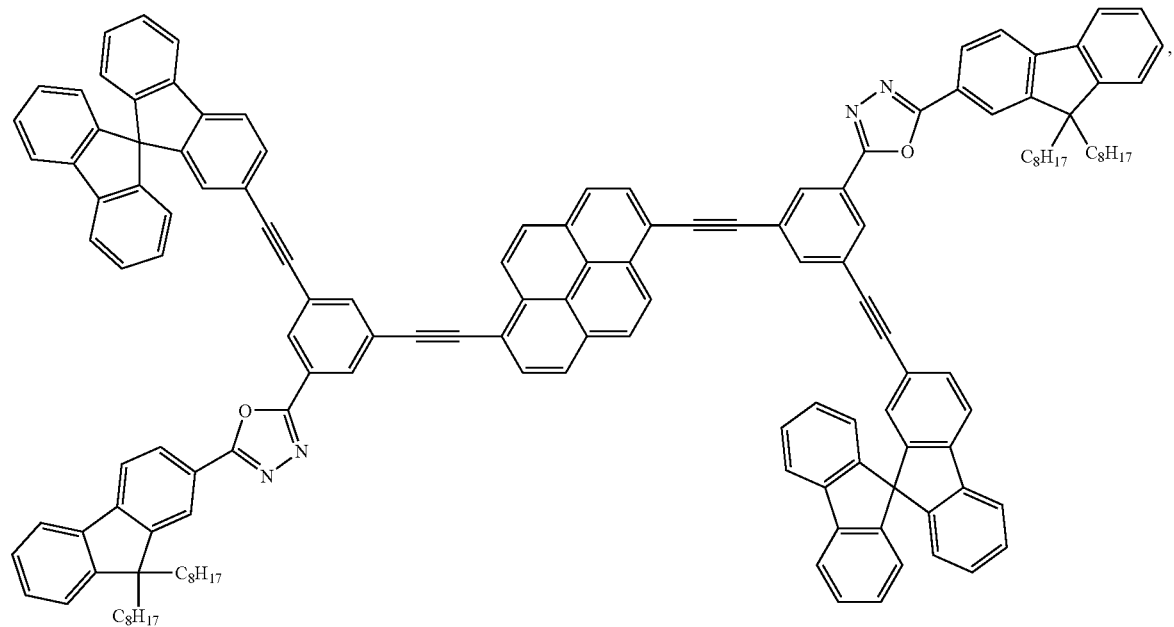
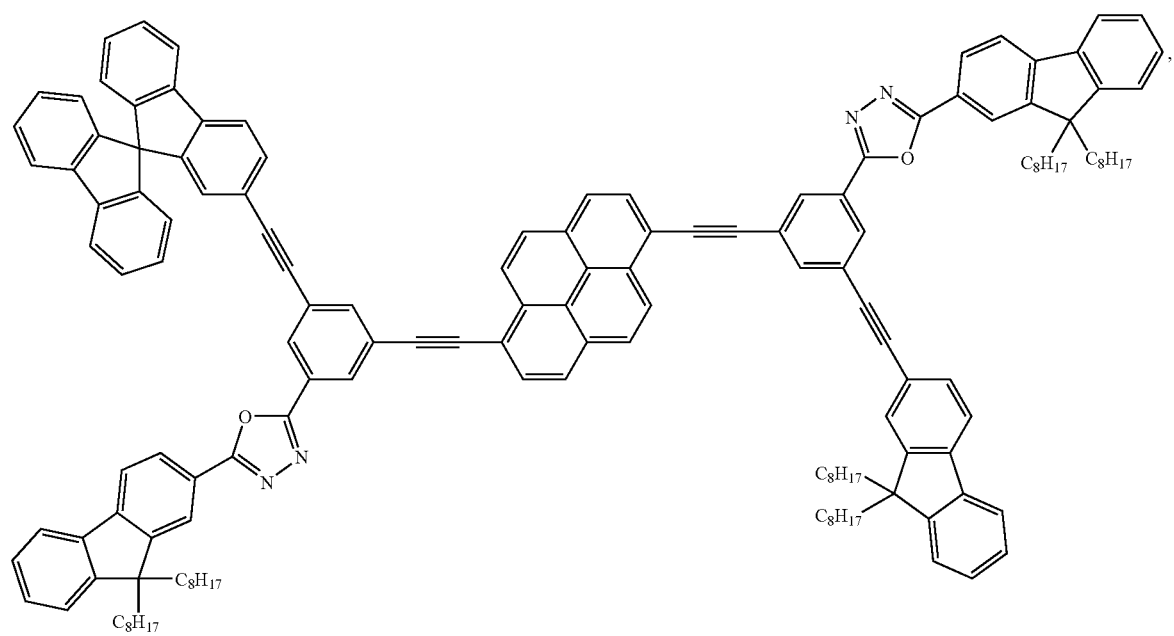

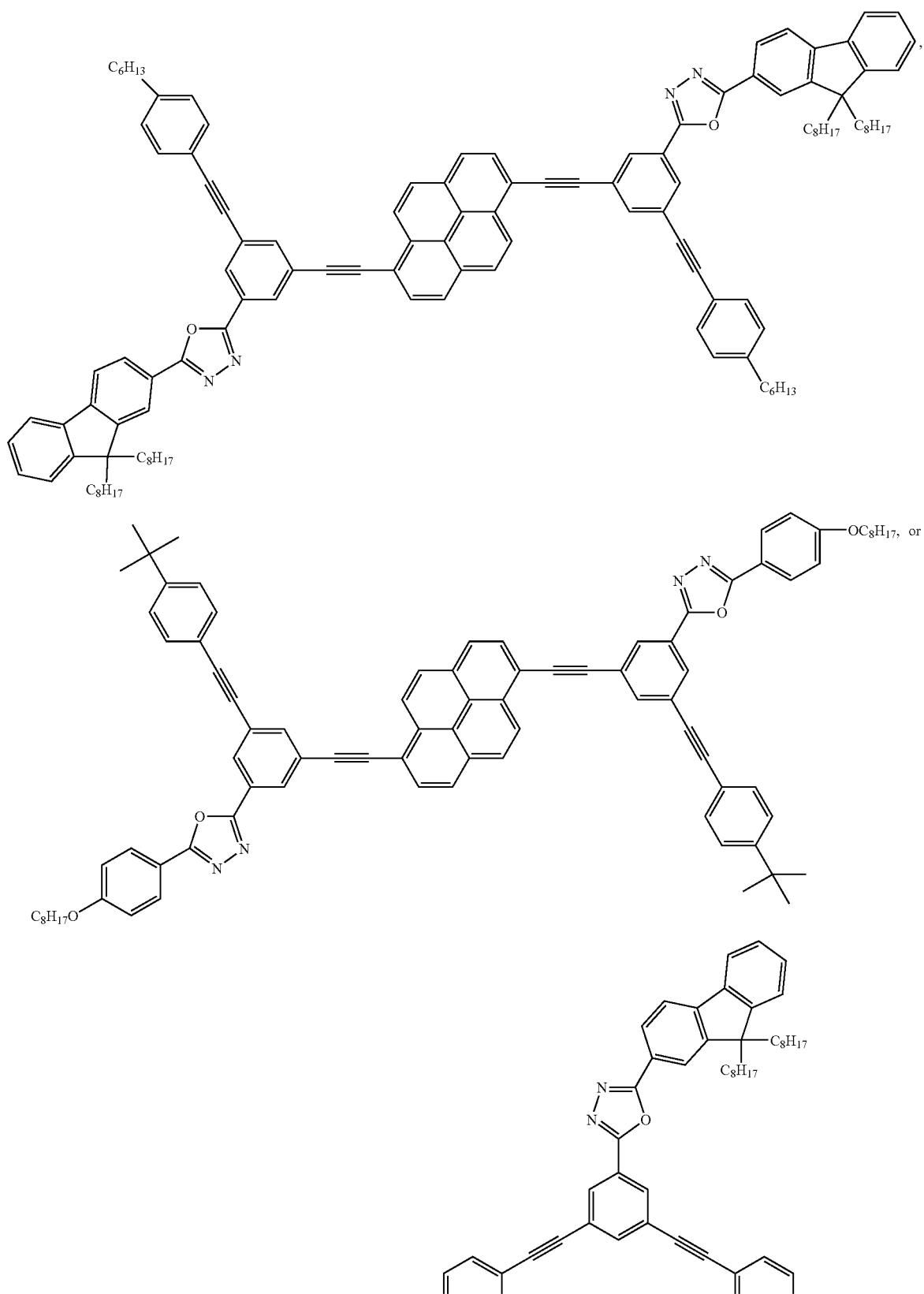

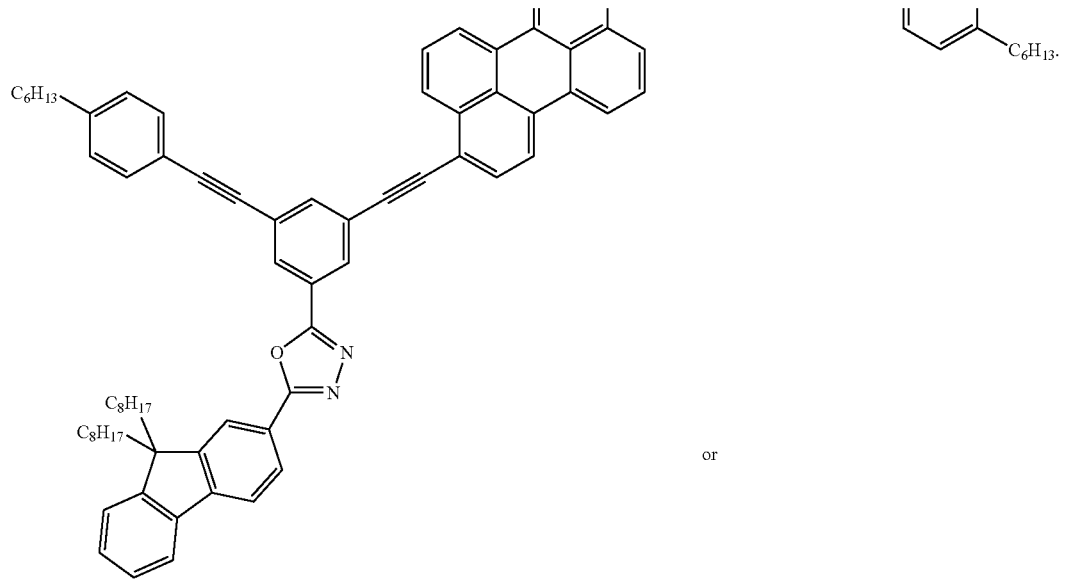
or
16. The compound of claim 1, wherein the compound is
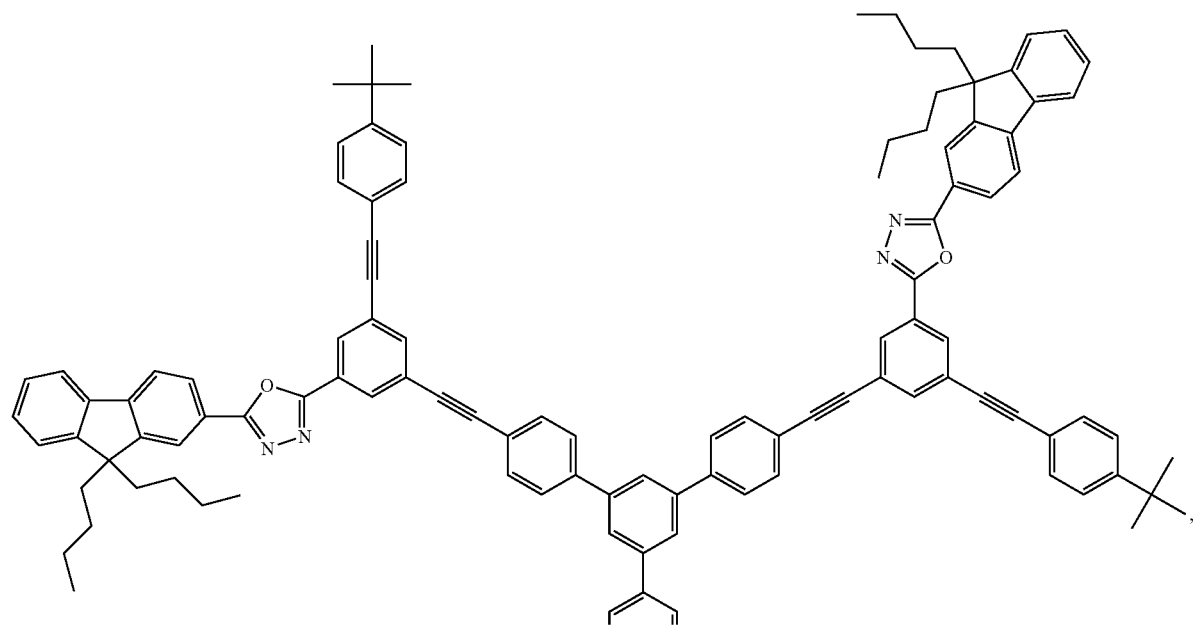

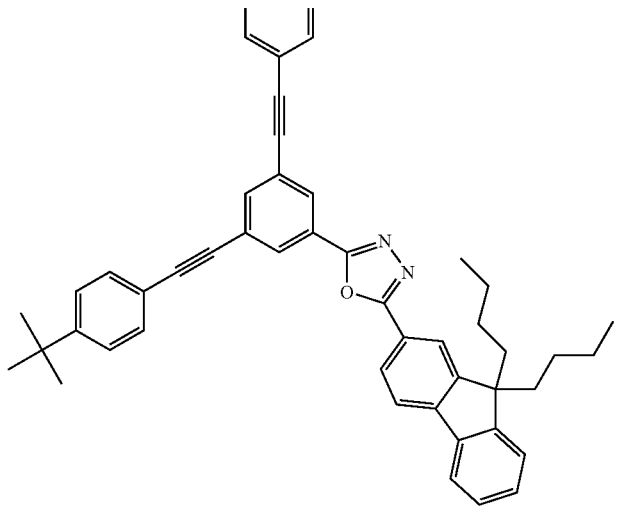
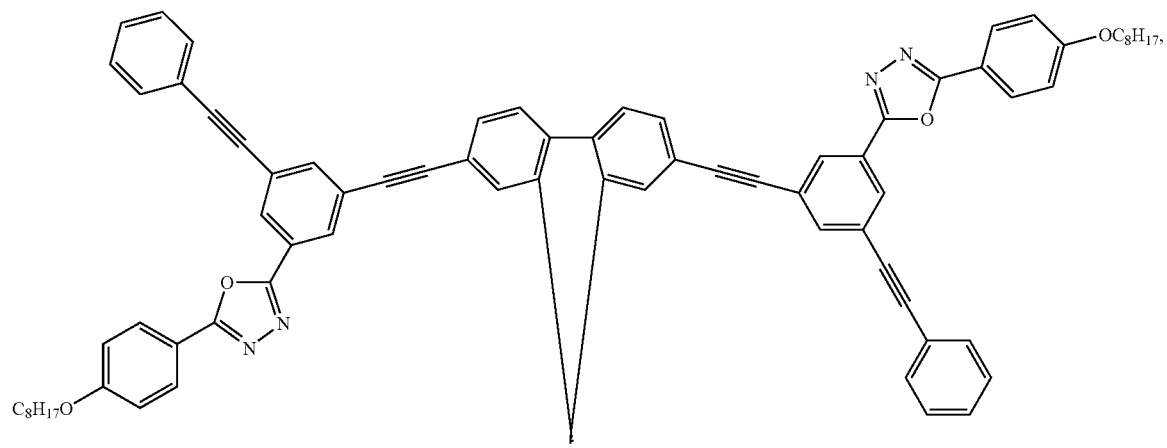
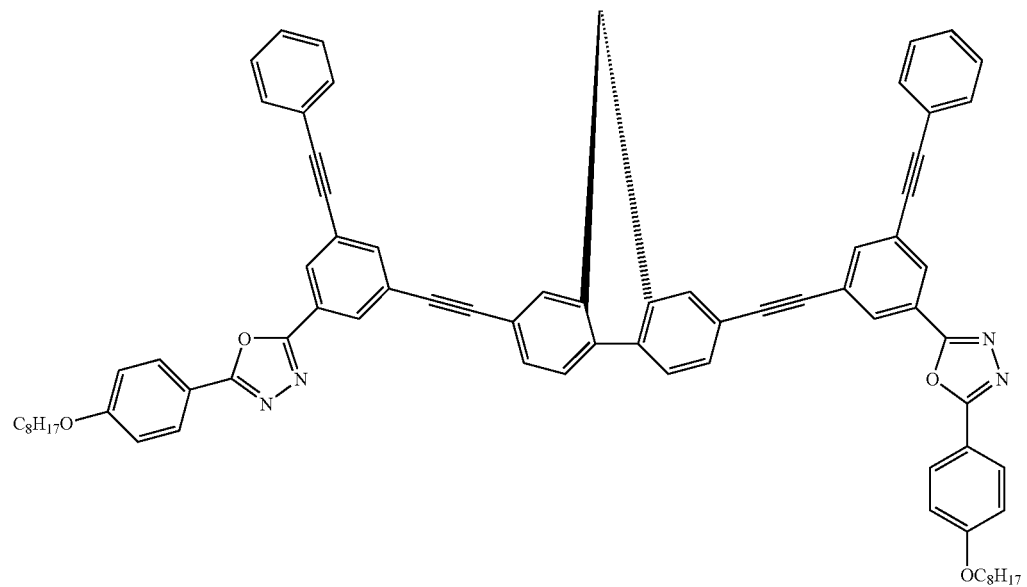

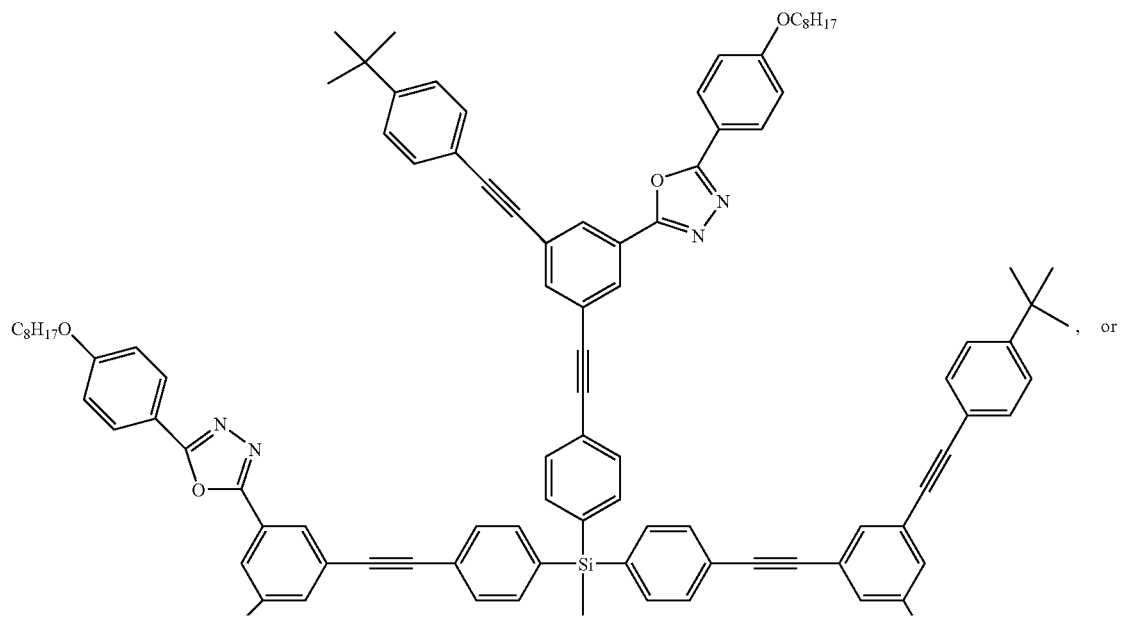
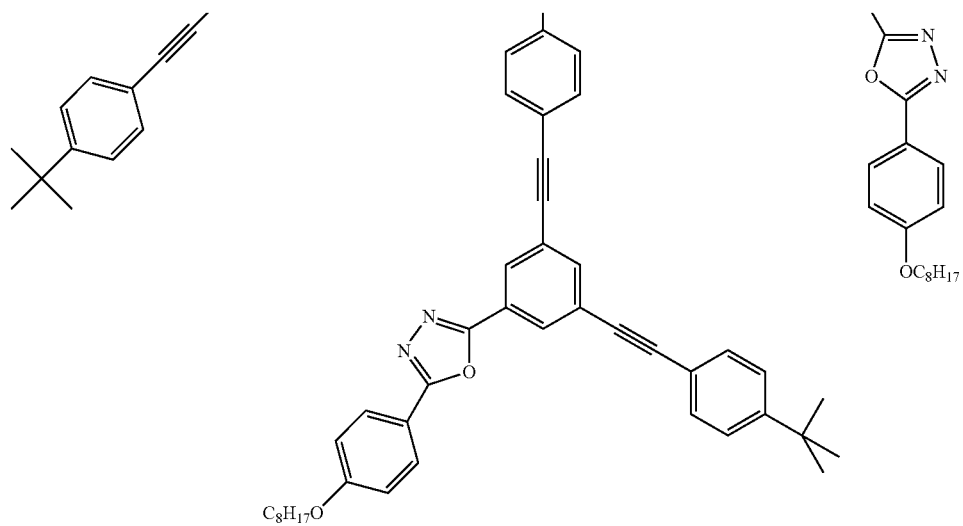

-continued

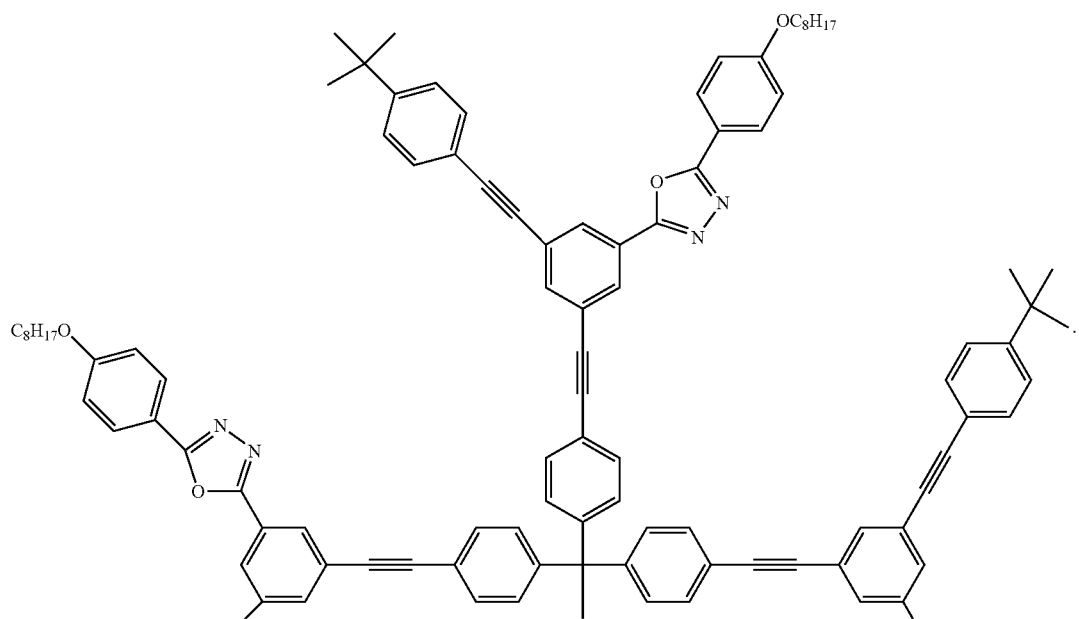

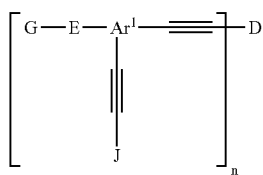
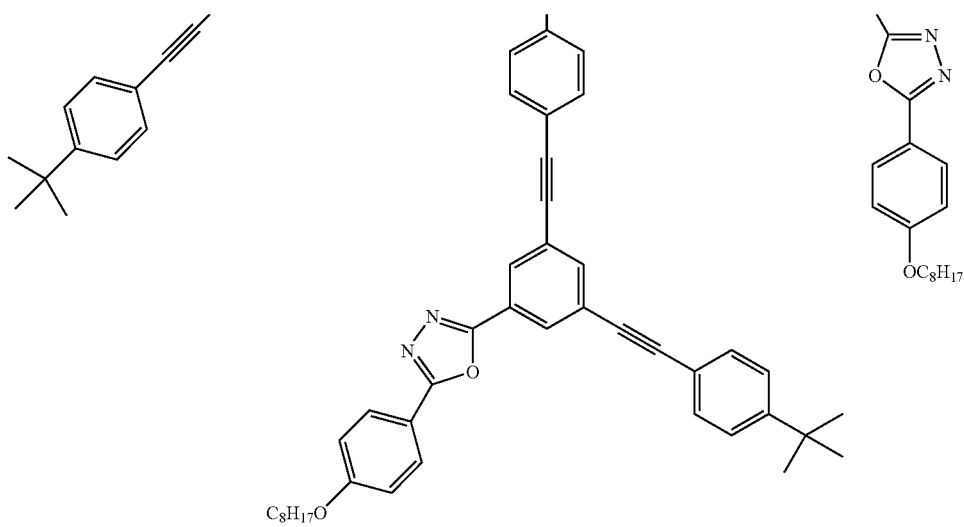
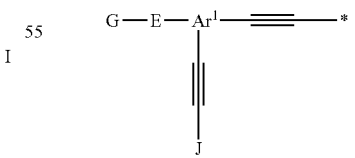

17. A composition comprising:
(a) a first compound of formula I $$\left[ G-E-Ar^1-\!\!\equiv\!\!\underset{\underset{J}{\overset{\|}{\underset{\|}{\phantom{-}}}}}{\phantom{-}}\right]_n\!\!\!-D \quad \text{I}$$

wherein
said compound comprises a first core D attached to first end capping groups of formula IV $$G-E-Ar^1-\!\!\equiv\!\!\underset{\underset{J}{\overset{\|}{\underset{\|}{\phantom{-}}}}}{\phantom{-}}\!\!-* \quad \text{IV}$$

D is a monovalent, divalent, trivalent, or tetravalent radical of a $C_{3-30}$ alkane, $C_{3-30}$ heteroalkane, conjugated or unconjugated $C_{6-60}$ carbocyclic aromatic compound, $C_{3-60}$ heteroaromatic compound, $C_{18-60}$ tertiary aromatic amino compound, or a compound of Formula II or Formula III

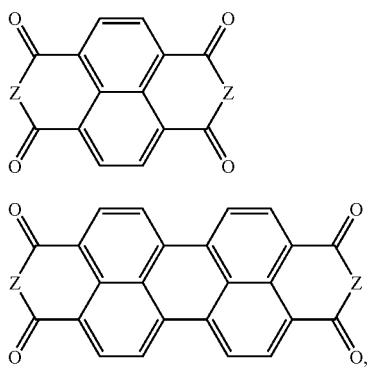

wherein D is unsubstituted or substituted with one or more alkyl, alkenyl, alkoxy, aryl, aryloxy, fluoro, fluoroalkyl, perfluoroalkyl, heteroalkyl, heteroaryl, or combinations thereof, wherein $Ar^1$ is trivalent radical of a conjugated $C_{6-30}$ carbocyclic aromatic compound that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

E is a $C_{3-60}$ heteroarylene having at least one —C=N— unit, said heteroarylene being unsubstituted or substituted with one or more alkyl, alkenyl, alkoxy, aryl, aryloxy, fluoro, fluoroalkyl, perfluoroalkyl, heteroalkyl, heteroaryl, or combinations thereof;

G is a monovalent radical selected from hydrogen, $C_{1-30}$ alkyl, $C_{1-30}$ heteroalkyl, $C_{3-60}$ heteroaryl, $C_{6-60}$ aryl, or $C_{18-60}$ tertiary aromatic amino aryl that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

J is a monovalent radical selected from $C_{1-30}$ alkyl, $C_{1-30}$ heteroalkyl, $C_{6-60}$ aryl, or $C_{18-60}$ tertiary aromatic amino aryl wherein J is unsubstituted or substituted with one or more alkyl, alkenyl, alkoxy, aryl, aryloxy, fluoro, fluoroalkyl, perfluoroalkyl, heteroalkyl, or combinations thereof;

Z is NH or $CH_2$;

n is an integer of 1 to 4, wherein no more than one of D and J is an unsubstituted phenyl when n is equal to 1; and (b) a second compound selected from a charge transporting material, a charge blocking material, a light emitting material, a color conversion material, a polymeric binder, or a combination thereof.

18. The composition of claim 17, wherein the composition comprises a hole transporting material and an electron transporting material.

19. The composition of claim 17, wherein the composition comprises a hole transporting material, an electron transporting material, and a light emitting material.

20. The composition of claim 17, wherein the second compound is selected from a charge transporting material, a charge blocking material, a light emitting material, a color conversion material, and a combination thereof, said second compound having a radical that comprises the first core of the first compound, wherein the radical of the second compound can be unsubstituted, substituted with a substituent of a same type that is present on the first core of the first compound, or substituted with a substituent that is absent on the first core of the first compound;

a second end capping group that comprises the first end capping group of the first compound, wherein the second end capping group can be unsubstituted, substituted with a substituent of a same type that is present on the first end capping group, or substituted with a substituent that is absent on the first end capping group;

a divalent radical that comprises a divalent radical of the first end capping group of the first compound, wherein the divalent radical in the second compound can be unsubstituted, substituted with a substituent of a same type that is present on the first end capping group, or substituted with a substituent that is absent on the first end capping group; or a combination thereof.

21. The composition of claim 20, wherein the second compound is non-polymeric, said second compound comprising a second core and at least one second end capping group.

22. The composition of claim 21, wherein the second end capping group of the second compound comprises the first end capping group of the first compound.

23. The composition of claim 22, further comprising a light emitting polymer.

24. The composition of claim 22, further comprising an electroactive polymer.

25. The composition of claim 22, further comprising an inactive polymer.

26. The composition of claim 22, wherein the second core of the second compound is different than the first core of the first compound and the composition further comprises a polymer that is the reaction product of a monomer mixture comprising a first monomer comprising the first core and a second monomer comprising the second core.

27. The composition of claim 21, wherein the second core of the second compound comprises the first core of the first compound.

28. The composition of claim 27, further comprising a light emitting polymer.

29. The composition of claim 27, further comprising an electroactive polymer.

30. The composition of claim 27, further comprising an inactive polymer.

31. The composition of claim 27, wherein the second compound has a second end capping group that is different than the first end capping group of the first compound and the composition further comprises a polymer that is the reaction product of a monomer mixture comprising a first monomer comprising the first end capping group or a divalent radical of the first end capping group and a second monomer comprising the second end capping group or a divalent radical of the second end capping group.

32. The composition of claim 20, wherein the second compound is a polymer comprising the reaction product of a monomer mixture comprising a first monomer comprising the first core of the first compound.

33. The composition of claim 20, wherein the second compound is a polymer that is the reaction product of a monomer mixture comprising a first monomer comprising the first end capping group or a radical of the first end capping group.

34. The composition of claim 17, wherein composition is amorphous.

35. The composition of claim 17, wherein the composition is solution processable.

36. An organic electronic device comprising a compound of Formula I:

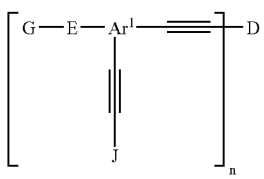

wherein

D is a monovalent, divalent, trivalent, or tetravalent radical of a $C_{3-30}$ alkane, $C_{3-30}$ heteroalkane, conjugated or unconjugated $C_{6-60}$ carbocyclic aromatic compound, $C_{3-60}$ heteroaromatic compound, $C_{18-60}$ tertiary aromatic amino compound, or a compound of Formula II or Formula III

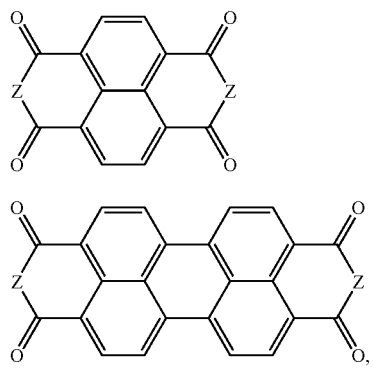

wherein D is unsubstituted or substituted with one or more alkyl, alkenyl, alkoxy, aryl, aryloxy, fluoro, fluoroalkyl, perfluoroalkyl, heteroalkyl, heteroaryl, or combinations thereof, wherein $Ar^1$ is trivalent radical of a conjugated $C_{6-30}$ carbocyclic aromatic compound that is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

E is a $C_{3-60}$ heteroarylene having at least one —C=N— unit, said heteroarylene being unsubstituted or substituted with one or more alkyl, alkenyl, alkoxy, aryl, aryloxy, fluoro, fluoroalkyl, perfluoroalkyl, heteroalkyl, heteroaryl, or combinations thereof;

G is a monovalent radical selected from hydrogen, $C_{1-30}$ alkyl, $C_{1-30}$ heteroalkyl, $C_{3-60}$ heroroaryl, $C_{6-60}$ aryl or $C_{18-60}$ tertiary aromatic amino aryl wherein G is unsubstituted or substituted with one or more alkyl, alkenyl, alkoxy, aryl, aryloxy, fluoro, fluoroalkyl, perfluoroalkyl, heteroalkyl, heteroaryl, or combinations thereof;

J is a monovalent radical selected from $C_{1-30}$ alkyl, $C_{1-30}$ heteroalkyl, $C_{6-60}$ aryl, or $C_{18-60}$ tertiary aromatic amino aryl wherein J is unsubstituted or substituted with one or more alkyl, alkenyl, alkoxy, aryl, aryloxy, fluoro, fluoroalkyl, perfluoroalkyl, heteroalkyl, or combinations thereof;

Z is NH or $CH_2$ and n is an integer of 1 to 4, wherein no more than one of D and J is an unsubstituted phenyl when n is equal to 1.

37. The organic electronic device of claim 36, wherein the device is an organic electroluminescent device.

38. The organic electronic device of claim 37, wherein the organic electroluminescent device comprises an organic emissive element comprising the compound of Formula I.

39. The organic electronic device of claim 38, wherein the organic emissive element further comprises a charge transporting material, a charge blocking material, a polymeric material, a light emitting material, a color conversion layer, or a combination thereof.

40. The organic electronic device of claim 38, wherein the organic emissive element has multiple layers and the compound of Formula I is in a light emitting layer.

41. The organic electronic device of claim 38, wherein the organic emissive element has multiple layers and the compound of Formula I is in a charge transporting layer.

42. The organic electronic device of claim 38, wherein the compound of Formula I is a light emitting material.

* * * * *

UNITED STATES PATENT AND TRADEMARK OFFICE
CERTIFICATE OF CORRECTION

PATENT NO. : 7,192,657 B2
APPLICATION NO. : 10/414073
DATED : March 20, 2007
INVENTOR(S) : Ralph R. Roberts It is certified that error appears in the above-identified patent and that said Letters Patent is hereby corrected as shown below:

On Page 1 of the Title Pages, Col. 1, under (U.S. Patent Documents)
Line 5, insert -- 5,281,489     01/1994     Mori et al. -- after the "5,256,506" entity.

On Page 1 of the Title Pages, Col. 2, under (Foreign Patent Documents)
Line 7, insert -- JP     2002-308855     10/2002 -- after the "EP 0891121" entity.
Line 8, insert -- GB     2 348 316     9/2000 --.

On Page 2 of the Title Pages, Col. 2, under (Other Publications)
Line 11, delete "Anthracene" and insert -- Anthracence --, therefor.

On Page 3 of the Title Pages, Col. 1, under (Other Publications)
Line 10, delete "37,2082-2084" and insert -- 37, 2082-2084 --, therefor. (Consider space)
Line 17, delete "Schidio et al.," and insert -- Schidlo et al., --, therefor.

Col. 7
Line 67, before "aryl" delete "alkyl carbazole;".

Col. 8
Line 27, delete "Tanaka et al.," and insert -- Tamake et al., --, therefor.

Col. 10
Line 65, After "*–[Si($C_wH_{2w+1}$)$_2$O]–$_y$*" insert -- , --.

Col. 31
Line 57, delete "Of" and insert -- of --, therefor.

Col. 54
Line 34, delete "Transl.)." and insert -- Transl.), --, therefor.

Col. 56
Line 19, delete "Ar1," and insert -- $Ar^1$, --, therefor.
Line 63-64, delete "$Ar_1$" and insert -- $Ar^1$ --, therefor.

Col. 57
Lines 2-3, delete "$Ar_1$" and insert -- $Ar^1$ --, therefor.
Lines 10-11, delete "$Ar_1$" and insert -- $Ar^1$ --, therefor.
Lines 10-11, delete "$Ar_1$" and insert -- $Ar^1$ --, therefor.
Lines 17-18, delete "$Ar_1$" and insert -- $Ar^1$ --, therefor.

UNITED STATES PATENT AND TRADEMARK OFFICE
CERTIFICATE OF CORRECTION

PATENT NO. : 7,192,657 B2
APPLICATION NO. : 10/414073
DATED : March 20, 2007
INVENTOR(S) : Ralph R. Roberts It is certified that error appears in the above-identified patent and that said Letters Patent is hereby corrected as shown below:

Col. 59
Line 28, after "alkyl" insert -- , --.

Col. 61
Line 51, delete "benzoxazolate)zinc(II)," and insert -- benzoxazolate) zinc(II), --, therefor (Consider space).

Col. 73
Line 41, delete "hydroxyquinolato)aluminum" and insert -- hydroxyquinolato) aluminum --, therefor (Consider space).

Col. 75
Line 45, delete "5,693,446[," and insert -- 5,693,446; --, therefor.

Col. 76
Line 10, delete "1990," and insert -- 1990; --, therefor.

Col. 81
Line 58, delete "octylxoy" and insert -- octyloxy --, therefor.

Col. 82
Line 48, delete "pyerene)," and insert -- pyrene), --, therefor.

Col. 84
Line 25, delete "Pd(PPh$_3$)$_{4(}$(70" and insert -- Pd(PPh$_3$)$_4$ (70 --, therefor.
Line 39, after "yield" insert -- . --.

Col. 88
Line 15, delete "ylethvnyl)" and insert -- ylethynyl) --, therefor.

Col. 89
Line 22, delete "(10$^{-6-10-5}$" and insert -- (10$^{-6}$-10$^{-5}$ --, therefor.

Col. 90
Line 12, delete "(10$^{-6-10-5}$" and insert -- (10$^{-6}$-10$^{-5}$ --, therefor.

Col. 91
Line 29, in Claim 1, delete "or" and insert -- of --, therefor.
Line 65, in Claim 1, delete "fluru alkyl," and insert -- fluoroalkyl, --, therefor.

UNITED STATES PATENT AND TRADEMARK OFFICE
CERTIFICATE OF CORRECTION

PATENT NO. : 7,192,657 B2
APPLICATION NO. : 10/414073
DATED : March 20, 2007
INVENTOR(S) : Ralph R. Roberts It is certified that error appears in the above-identified patent and that said Letters Patent is hereby corrected as shown below:

<u>Col. 92</u>
Line 2, in Claim 1, after "heteroalkyl," insert -- carbocyclic --.

<u>Col. 98</u>
Line 47, in Claim 4, delete "thereof," and insert -- thereof; --, therefor.

<u>Col. 104</u>
Line 48, in Claim 11, delete "compriscs" and insert -- comprises --, therefor.
Line 51, in Claim 12, delete "B" and insert -- E --, therefor.

<u>Col. 125</u>
Line 35, in Claim 17, after "aryl" delete "that" and insert
 -- wherein G --, therefor.
Line 41, in Claim 17, after "heteroalkyl," insert -- carbocyclic --.

<u>Col. 128</u>
Line 8, in Claim 36, delete "heroroaryl," and insert -- heteroaryl, --, therefor.
Line 8, in Claim 36, delete "aryl" and insert -- aryl, --, therefor.

Signed and Sealed this

Twenty-first Day of August, 2007

JON W. DUDAS
*Director of the United States Patent and Trademark Office*